(12) United States Patent
Aissaoui et al.

(10) Patent No.: US 7,435,815 B2
(45) Date of Patent: Oct. 14, 2008

(54) SULFONYLAMINO-ACETIC ACID DERIVATIVES

(75) Inventors: Hamed Aissaoui, Pulversheim (FR); Martine Clozel, Binningen (CH); Walter Fischli, Allschwil (CH); Ralf Koberstein, Lörrach (DE); Thierry Sifferlen, Guewenheim (FR); Thomas Weller, Binningen (CH)

(73) Assignee: Actelion Pharmaceuticals Ltd. (CH)

( * ) Notice: Subject to any disclaimer, the term of this patent is extended or adjusted under 35 U.S.C. 154(b) by 0 days.

(21) Appl. No.: 11/756,008

(22) Filed: May 31, 2007

(65) Prior Publication Data

US 2007/0244156 A1    Oct. 18, 2007

Related U.S. Application Data

(62) Division of application No. 10/529,637, filed as application No. PCT/EP03/11021 on Oct. 6, 2003, now Pat. No. 7,279,578.

(30) Foreign Application Priority Data

Oct. 11, 2002    (WO) .................. PCT/EP02/11409

(51) Int. Cl.
*C07C 311/13*    (2006.01)
*C07C 311/20*    (2006.01)
*C07D 213/76*    (2006.01)
*C07D 213/75*    (2006.01)
*C07D 215/38*    (2006.01)

(52) U.S. Cl. .................. 546/1; 546/268.1; 546/304; 546/305; 546/309; 564/84; 564/90; 564/92

(58) Field of Classification Search .................. None
See application file for complete search history.

(56) References Cited

U.S. PATENT DOCUMENTS

2004/0072816 A1    4/2004   Quattropani et al.

FOREIGN PATENT DOCUMENTS

| WO | WO 99/09024 | 2/1999 |
|---|---|---|
| WO | WO 99/58533 | 11/1999 |
| WO | WO 00/47576 | 8/2000 |
| WO | WO 00/47577 | 8/2000 |
| WO | WO 00/47580 | 8/2000 |
| WO | WO 00/50391 | 8/2000 |
| WO | WO 01/68609 A1 | 9/2001 |
| WO | WO 01/85693 A1 | 11/2001 |
| WO | WO 01/96302 A1 | 12/2001 |
| WO | WO 02/32864 A1 | 4/2002 |
| WO | WO 02/44172 A1 | 6/2002 |
| WO | WO 02/051838 A1 | 7/2002 |
| WO | WO 02/089800 A2 | 11/2002 |
| WO | WO 02/090355 A1 | 11/2002 |
| WO | WO 03/002559 A2 | 1/2003 |
| WO | WO 03/002561 A1 | 1/2003 |
| WO | WO 03/032991 A1 | 4/2003 |
| WO | WO 03/037847 A1 | 5/2003 |
| WO | WO 03/041711 A1 | 5/2003 |
| WO | WO 03/051368 A1 | 6/2003 |
| WO | WO 03/051871 A1 | 6/2003 |
| WO | WO 03/051872 A1 | 6/2003 |
| WO | WO 03/051873 A1 | 6/2003 |

OTHER PUBLICATIONS

Chemelli et al., Cell, vol. 98, pp. 437-451 (1999).
Sakurai et al., Cell, vol. 92, pp. 573-585 (1998).
Malinovskii, M.S., et al.; "Sulfanilides. I. N-Sulfonylarylglycine dialkylamides" retrieved from STN Database accession No. 1963:33088; Abstract; and Zhurnal Obshchei Khimii (1962), 32, 726-8.

*Primary Examiner*—Yvonne Eyler
*Assistant Examiner*—Yevegeny Valenrod
(74) *Attorney, Agent, or Firm*—Dickstein, Shapiro, LLP.

(57)    ABSTRACT

The invention relates to novel sulfonylamino-acetic acid derivatives and their use as active ingredients in the preparation of pharmaceutical compositions. The invention also concerns related aspects including processes for the preparation of such compounds, pharmaceutical compositions containing one or more of those compounds and especially their use as orexin receptor antagonists.

14 Claims, No Drawings

SULFONYLAMINO-ACETIC ACID DERIVATIVES

This application is a division of U.S. patent application Ser. No. 10/529,637, filed Mar. 31, 2005; which is a U.S. national stage patent application of international application, PCT/EP2003/011021, filed Oct. 6, 2003; which claims priority to PCT/EP02/11409, filed Oct. 11, 2002, all of which are incorporated herein by reference in their entireties.

The present invention relates to novel Sulfonylamino-acetic acid derivatives of the general formula (I) and their use as pharmaceuticals. The invention also concerns related aspects including pharmaceutical compositions containing one or more compounds of formula I, and especially their use as orexin receptor antagonists.

The orexins (hypocretins) comprise two neuropeptides produced in the hypothalamus: the orexin A (OX-A) (a 33 aminoacid peptide) and the orexin B (OX-B) (a 28 aminoacid peptide) (Sakurai T. et al., Cell, 1998, 92, 573-585). Orexins are found to stimulate food consumption in rats suggesting a physiological role for these peptides as mediators in the central feedback mechanism that regulates feeding behavior (Sakurai T. et al., Cell, 1998, 92, 573-585). On the other hand, it was also proposed that orexins regulate states of sleep and wakefulness opening potentially novel therapeutic approaches for narcoleptic patients (Chemelli R. M. et al., Cell, 1999, 98, 437-451). Two orexin receptors have been cloned and characterized in mammals which belong to the G-protein coupled receptor superfamily (Sakurai T. et al., Cell, 1998, 92, 573-585), the orexin-1 receptor ($OX_1$) which is selective for OX-A and the orexin-2 receptor ($OX_2$) which is capable to bind OX-A as well as OX-B.

Orexin receptors are found in the mammalian host and may be responsible for many pathologies including, but not limited to, depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; schizophrenia; manic depression; delirium; dementia; severe mental retardation and dyskinesias such as Huntington's disease and Tourette syndrome; feeding disorders such as anorexia, bulimia, cachexia and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; inflammatory bowel disease; gastric diskinesia; gastric ulcus; Froehlich's syndrome; adrenohypophysis disease; hypophysis disease; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischaemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. by HIV; post-chemotherapy pain; post-stroke pain; post-operative pain; neuralgia; conditions associated with visceral pain such as irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; delayed or advanced sleep phase syndrome; sleep related dystonias; and neurodegerative disorders including nosological entities such as disinhibition-dementia-parkinsonism-amyotrophy complex; pallido-ponto-nigral degeneration epilepsy; seizure disorders including febrile seizures and other hyperthermia disorders; and other diseases related to orexin.

Up to now some low molecular weight compounds are known which have a potential to antagonise either specifically $OX_1$ or $OX_2$, or both receptors at the same time. In WO 99/09024, WO 99/58533, WO 00/47576, WO 00/47577 and WO 00/47580 formerly SmithKline Beecham reported phenylurea, phenylthiourea and cinamide derivatives as $OX_1$ selective antagonists. More recently WO 01/85693 from Banyu Pharmaceuticals has been published wherein N-acyltetrahydroisoquinoline derivatives are disclosed. 2-Amino-methylpiperidine derivatives (WO 01/96302), 3-aminomethyl-morpholine derivatives (WO 02/44172) and N-aroyl cyclic amines (WO 02/89800, WO 02/90355, WO 03/51368 and WO 03/51871) have been suggested by formerly SmithKline Beecham as orexin receptor antagonists. Related compounds are disclosed in WO 03/02559, WO 03/02561, WO 03/32991, WO 03/41711, WO 03/51872 and WO 03/51873. In WO 03/37847 formerly SmithKline Beecham reported benzamide derivatives as orexin receptor antagonists. International patent applications WO 01/68609 and WO 02/51838 disclose 1,2,3,4-tetrahydroisoquinoline and novel benzazepine derivatives as orexin receptor antagonists. The novel compounds of the present invention belong to an entirely different class of low molecular weight compounds as compared to all prior art orexin receptor antagonists so far published.

The present invention comprises Sulfonylamino-acetic acid derivatives which are non-peptide antagonists of the human orexin receptors, in particular the human orexin-2 receptor. These compounds, therefore, are of potential use in the treatment of disturbed homeostasis and eating disorders (e.g. bulimia, obesity, food abuse, compulsive eating or irritable bowel syndrome), as well as disturbed sleep/wake schedule, sleep disorders (e.g. insomnias, apneas, dystonias) or stress-related diseases (e.g. anxiety, mood and blood pressure disorders) or any other disease related to orexin dysfunction.

WO 00/50391 discloses certain sulfonamide derivatives as modulators of the production of amyloid β-protein. WO 02/32864 discloses certain sulfanilide derivatives useful in the treatment of diseases mediated by oxytocin and/or vasopressin.

The present invention relates to novel Sulfonylamino-acetic acid derivatives of the general formula (I).

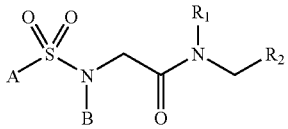

Formula (I)

wherein:
A represents 4-ethylphenyl-, 4-isopropylphenyl, 4-tert.-butylphenyl-, 2-methylphenyl-, 3-methylphenyl-, 4-cyclopropylphenyl, 3-fluorophenyl-, 2-chlorophenyl-, 3-chlorophenyl-, 4-bromophenyl-, 2-trifluoromethylphenyl-, 3-trifluoromethylphenyl-, 4-(1-hydroxy-1-methyl-ethyl)-phenyl-, 3-chloro-4-methylphenyl-, 2-methoxy-4-methylphenyl-, 3,4-difluorophenyl-, 1,2,3,4-tetrahydroisoquinolin-7-yl, 2-methyl-1,2,3,4-tetrahydroisoquinolin-7-yl, 2-formyl-1,2,3,4-tetrahydroisoquinolin-7-yl, phenylethenyl-, 1-naphthyl-, 2-naphthyl-, 3-methyl-pyridin-2-yl, 5-methyl-pyridin-2-yl, 5-isopropyl-pyridin-2-yl, 6-dimethylamino-pyridin-3-yl, 6-bromo-5-chloro-pyridin-3-yl or 8-quinolinyl-;
B represents a phenyl, a 6-membered heteroaryl or a nine- or ten-membered bicyclic heteroaryl group, which groups are unsubstituted or independently mono- or di-substituted with cyano, halogen, hydroxy, lower alkyl, hydroxy lower alkyl, amino lower alkyl, aminocarbonyl lower alkyl, sulfonylamino lower alkyl, lower alkenyl, lower alkoxy, trifluoromethyl, trifluoromethoxy, cycloalkyloxy, aryloxy, aralkyloxy, heterocyclyloxy, heterocyclyl lower alkyloxy, amino, aminocarbonyl or sulfonylamino; or a cyclohexyl, 3-piperidinyl or 4-piperidinyl group, which groups are unsubstituted or mono-substituted with hydroxy, lower alkyl, hydroxy lower alkyl, aminocarbonyl lower alkyl, sulfonylamino lower alkyl, amino, aminocarbonyl or sulfonylamino;

with the proviso that in case A represents 2-methylphenyl- or 4-bromophenyl the phenyl ring as represented by B is substituted;
$R^1$ represents lower alkyl, cycloalkyl, hydroxy lower alkyl or cyano lower alkyl;
$R^2$ represents lower alkyl, lower alkenyl, hydroxy lower alkyl, amino lower alkyl, sulfonylamino lower alkyl, cycloalkyl; an unsubstituted or mono- or disubstituted phenyl group substituted independently with cyano, halogen, hydroxy, lower alkyl, lower alkoxy, cycloalkyloxy, amino, amino lower alkyl, aminocarbonyl or sulfonylamino; an unsubstituted or mono- or di-substituted five- or six-membered heteroaryl group substituted independently with cyano, halogen, hydroxy, lower alkyl, lower alkoxy, cycloalkyloxy, amino, amino lower alkyl, aminocarbonyl or sulfonylamino; an unsubstituted or mono- or di-substituted nine- or ten-membered bicyclic heteroaryl group substituted independently with cyano, halogen, hydroxy, lower alkyl, lower alkoxy, cycloalkyloxy, amino, amino lower alkyl, aminocarbonyl or sulfonylamino;

and pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, and morphological forms, thereof.

In the present description the term "lower alkyl", alone or in combination, means a straight-chain or branched-chain alkyl group with 1-5 carbon atoms as for example methyl, ethyl, propyl, isopropyl, butyl, sec.-butyl, tert-butyl, isobutyl and the isomeric pentyls.

The term "lower alkenyl" means a straight-chain or branched-chain alkenyl group with 2 to 5 carbon atoms, preferably allyl and vinyl.

The term "lower alkoxy", alone or in combination, means a group of the formula lower alkyl-O— in which the term "lower alkyl" has the previously given significance, such as methoxy, ethoxy, n-propoxy, isopropoxy, n-butoxy, isobutoxy, sec-butoxy and tert-butoxy, preferably methoxy and ethoxy.

The term "cycloalkyl", alone or in combination, means a cycloalkyl ring with 3 to 6 carbon atoms. Examples of $C_3$-$C_6$ cycloalkyl are cyclopropyl, cyclobutyl, cyclopentyl, cyclohexyl, preferably cyclopropyl, cyclohexyl and particularly cyclohexyl or lower alkyl substituted cycloalkyl which may preferably be substituted with lower alkyl such as methyl-cyclopropyl, dimethyl-cyclopropyl, methyl-cyclobutyl, methyl-cyclopentyl, methyl-cyclohexyl or dimethyl-cyclohexyl.

The term "aryl" means a phenyl or naphthyl group which optionally carries one or more substituents, preferably one or two substituents, each independently selected from cyano, halogen, hydroxy, lower alkyl, lower alkenyl, lower alkoxy, lower alkenyloxy, trifluoromethyl, trifluoromethoxy, amino, or carboxy.

The term "aralkyl" means a lower alkyl group as previously defined in which one hydrogen atom has been replaced by an aryl group as previously defined.

The term "heterocyclyl" means a 5- to 10-membered monocyclic or bicyclic ring, which may be saturated, partially unsaturated or aromatic containing for example 1, 2 or 3 heteroatoms selected from oxygen, nitrogen and sulphur which may be the same or different. Examples of such heterocyclyl groups are pyrrolidinyl, piperidinyl, piperazinyl, morpholinyl, pyridyl, pyrimidinyl, pyrazinyl, pyridazinyl, quinolyl, isoquinolyl, thienyl, thiazolyl, isothiazolyl, furyl, imidazolyl, pyrazolyl, pyrrolyl, indazolyl, indolyl, isoindolyl, isoxazolyl, oxazolyl, quinoxalinyl, phthalazinyl, cinnolinyl, dihydropyrrolyl, pyrrolidinyl, isobenzofuranyl, tetrahydrofuranyl, dihydropyranyl. The heterocyclyl group may have up to 5, preferably 1, 2 or 3 optional substituents. Examples of suitable substituents include halogen, lower alkyl, amino, nitro, cyano, hydroxy, lower alkoxy, carboxy and lower alkyloxy-carbonyls.

The term "6-membered heteroaryl group" means e.g. a pyridyl, pyrimidinyl, pyrazinyl or a pyridazinyl group.

The term "nine- or ten-membered bicyclic heteroaryl group" means e.g. an indazolyl, indolyl, isoindolyl, benzimidazolyl, benzoxazolyl, benzisoxazolyl, benzothiazolyl, quinolinyl, isoquinolinyl, quinoxalinyl, phthalazinyl, cinnolinyl, quinazolinyl or a naphthyridinyl group.

The term "5-membered heteroaryl group" means e.g. a pyrrolyl, furyl, thienyl, imidazolyl, pyrazolyl, oxazolyl, isoxazolyl, thiazolyl, isothiazolyl or thiadiazolyl group.

The term "amino" in terms like "amino", "amino lower alkyl", "aminocarbonyl" or "aminocarbonyl lower alkyl" represents a $NH_2$—, $NHR^3$— or a $NR^3R^4$— group. $R^3$ and $R^4$ are lower alkyl groups, which might be equal or different.

The term "sulfonylamino" in terms like "sulfonylamino" or "sulfonylaminoalkyl" represents a $R^5S(O)_2NR^3$— group. $R^5$ represents a lower alkyl group, a phenyl group, a 6-membered heteroaryl group or a 5-membered heteroaryl group.

The term "halogen" means fluorine, chlorine, bromine or iodine and preferably chlorine and bromine and particularly chlorine.

A preferred group of compounds of formula (I) are those in which B, R$^1$ and R$^2$ have the meaning given in formula (I) above and A represents a 4-ethylphenyl group;

and pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, and morphological forms, thereof.

Another preferred group of compounds of formula (I) are those in which B, R$^1$ and R$^2$ have the meaning given in formula (I) above and A represents a 4-isopropylphenyl group;

and pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, and morphological forms, thereof.

Another preferred group of compounds of formula (I) are those in which B, R$^1$ and R$^2$ have the meaning given in formula (I) above and A represents a 4-tert.-butylphenyl group;

and pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, and morphological forms, thereof.

Another preferred group of compounds of formula (I) are those in which B, R$^1$ and R$^2$ have the meaning given in formula (I) above and A represents a 2-methylphenyl group;

and pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, and morphological forms, thereof.

Another preferred group of compounds of formula (I) are those in which B, R$^1$ and R$^2$ have the meaning given in formula (I) above and A represents a 3-methylphenyl group;

and pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, and morphological forms, thereof.

Another preferred group of compounds of formula (I) are those in which B, R$^1$ and R$^2$ have the meaning given in formula (I) above and A represents a 4-(1-hydroxy-1-methyl-ethyl)-phenyl group;

and pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, and morphological forms, thereof.

Another preferred group of compounds of formula (I) are those in which B, R$^1$ and R$^2$ have the meaning given in formula (I) above and A represents a 3-chloro-4-methylphenyl group;

and pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, and morphological forms, thereof.

Another preferred group of compounds of formula (I) are those in which B, R$^1$ and R$^2$ have the meaning given in formula (I) above and A represents a 2-formyl-1,2,3,4-tetrahydroisoquinolin-7-yl group;

and pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, and morphological forms, thereof.

Another preferred group of compounds of formula (I) are those in which B, R$^1$ and R$^2$ have the meaning given in formula (I) above and A represents a 2-naphthyl group;

and pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, and morphological forms, thereof.

Another preferred group of compounds of formula (I) are those in which B, R$^1$ and R$^2$ have the meaning given in formula (I) above and A represents a 3-methyl-pyridin-2-yl group;

and pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, and morphological forms, thereof.

Another preferred group of compounds of formula (I) are those in which B, R$^1$ and R$^2$ have the meaning given in formula (I) above and A represents a 5-isopropyl-pyridin-2-yl group;

and pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, and morphological forms, thereof.

Another preferred group of compounds of formula (I) are those in which B, R$^1$ and R$^2$ have the meaning given in formula (I) above and A represents a 6-dimethylamino-pyridin-3-yl group;

and pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, and morphological forms, thereof.

Examples of preferred compounds of formula (I) are:

2-[(4-tert-Butyl-benzenesulfonyl)-p-tolyl-amino]-N,N-diethyl-acetamide;

N,N-Diethyl-2-[(naphthalene-2-sulfonyl)-p-tolyl-amino]-acetamide;

N,N-Diethyl-2-[(toluene-3-sulfonyl)-p-tolyl-amino]-acetamide;

N,N-Diethyl-2-[(4-ethyl-benzenesulfonyl)-p-tolyl-amino]-acetamide;

N,N-Diethyl-2-[(toluene-2-sulfonyl)-p-tolyl-amino]-acetamide;

2-[(4-tert-Butyl-benzenesulfonyl)-phenyl-amino]-N,N-diethyl-acetamide;

2-[(4-tert-Butyl-benzenesulfonyl)-(4-methoxy-phenyl)-amino]-N,N-diethyl-acetamide;

2-[(4-tert-Butyl-benzenesulfonyl)-cyclohexyl-amino]-N,N-diethyl-acetamide;

2-[(4-tert-Butyl-benzenesulfonyl)-(4-methyl-cyclohexyl)-amino]-N,N-diethyl-acetamide;

2-[(4-tert-Butyl-benzenesulfonyl)-(6-chloro-pyridin-3-yl)-amino]-N,N-diethyl-acetamide;

2-[(4-tert-Butyl-benzenesulfonyl)-(3-methoxy-phenyl)-amino]-N,N-diethyl-acetamide;
2-[(4-tert-Butyl-benzenesulfonyl)-m-tolyl-amino]-N,N-diethyl-acetamide;
2-[(4-tert-Butyl-benzenesulfonyl)-o-tolyl-amino]-N,N-diethyl-acetamide;
2-[(4-tert-Butyl-benzenesulfonyl)-(2-methoxy-phenyl)-amino]-N-cyclopropyl-methyl-N-n-propyl-acetamide;
2-[(4-tert-Butyl-benzenesulfonyl)-(6-chloro-pyridin-3-yl)-amino]-N-cyclo-propylmethyl-N-n-propyl-acetamide;
2-[(4-tert-Butyl-benzenesulfonyl)-m-tolyl-amino]-N-cyclopropylmethyl-N-n-propyl-acetamide;
2-[(6-Dimethylamino-pyridine-3-sulfonyl)-p-tolyl-amino]-N-ethyl-N-pyridin-2-ylmethyl-acetamide;
2-[(4-tert-Butyl-benzenesulfonyl)-p-tolyl-amino]-N,N-di-n-propyl-acetamide;
N-Benzyl-2-[(4-tert-butyl-benzenesulfonyl)-p-tolyl-amino]-N-ethyl-acetamide;
2-[(4-tert-Butyl-benzenesulfonyl)-p-tolyl-amino]-N-ethyl-N-pyridin-4-ylmethyl-acetamide;
N-Benzyl-N-ethyl-2-[(toluene-2-sulfonyl)-p-tolyl-amino]-acetamide;
N,N-Diethyl-2-[(2-methoxy-phenyl)-(toluene-2-sulfonyl)-amino]-acetamide;
2-[(4-tert-Butyl-benzenesulfonyl)-(6-methoxy-pyridin-3-yl)-amino]-N,N-diethyl-acetamide;
2-[(4-tert-Butyl-benzenesulfonyl)-(2-methoxy-phenyl)-amino]-N,N-diethyl-acetamide;
N-Benzyl-N-ethyl-2-[(6-methoxy-pyridin-3-yl)-(toluene-2-sulfonyl)-amino]-acetamide;
N-Benzyl-N-ethyl-2-[(2-methoxy-phenyl)-(toluene-2-sulfonyl)-amino]-acetamide;
N-Benzyl-2-[(4-tert-butyl-benzenesulfonyl)-(2-methoxy-phenyl)-amino]-N-ethyl-acetamide;
N-Benzyl-N-ethyl-2-[(6-methoxy-pyridin-3-yl)-(naphthalene-2-sulfonyl)-amino]-acetamide;
N-Benzyl-N-ethyl-2-[(2-methoxy-phenyl)-(naphthalene-2-sulfonyl)-amino]-acetamide;
2-[(4-tert-Butyl-benzenesulfonyl)-p-tolyl-amino]-N-ethyl-N-(2-hydroxy-ethyl)-acetamide;
N,N-Diethyl-2-[(4-isopropyl-benzenesulfonyl)-p-tolyl-amino]-acetamide;
2-[(3-Chloro-4-methyl-benzenesulfonyl)-p-tolyl-amino]-N,N-diethyl-acetamide;
N,N-Diethyl-2-[(5-isopropyl-pyridine-2-sulfonyl)-p-tolyl-amino]-acetamide;
N-Benzyl-2-[(4-tert-butyl-benzenesulfonyl)-p-tolyl-amino]-N-(2-hydroxy-ethyl)-acetamide;
2-[(4-tert-Butyl-benzenesulfonyl)-p-tolyl-amino]-N,N-bis-(2-hydroxy-ethyl)-acetamide;
2-[(4-tert-Butyl-benzenesulfonyl)-p-tolyl-amino]-N-(2-cyano-ethyl)-N-ethyl-acetamide;
2-[(4-tert-Butyl-benzenesulfonyl)-p-tolyl-amino]-N-ethyl-N-pyridin-2-ylmethyl-acetamide;
2-[(4-tert-Butyl-benzenesulfonyl)-p-tolyl-amino]-N-ethyl-N-pyridin-3-ylmethyl-acetamide;
2-[(4-tert-Butyl-benzenesulfonyl)-p-tolyl-amino]-N-ethyl-N-(6-methyl-pyridin-2-ylmethyl)-acetamide;
2-[(4-tert-Butyl-benzenesulfonyl)-p-tolyl-amino]-N-ethyl-N-thiazol-2-ylmethyl-acetamide;
N-Benzyl-2-[(4-tert-butyl-benzenesulfonyl)-quinolin-6-yl-amino]-N-(2-hydroxy-ethyl)-acetamide;
2-[(4-tert-Butyl-benzenesulfonyl)-quinolin-6-yl-amino]-N-ethyl-N-thiazol-2-ylmethyl-acetamide;
N-Benzyl-2-[(4-tert-butyl-benzenesulfonyl)-quinolin-6-yl-amino]-N-ethyl-acetamide;
2-[(4-tert-Butyl-benzenesulfonyl)-quinolin-6-yl-amino]-N-ethyl-N-(6-methyl-pyridin-2-ylmethyl)-acetamide;
2-[(4-tert-Butyl-benzenesulfonyl)-(3-dimethylamino-phenyl)-amino]-N,N-diethyl-acetamide;
2-[(4-tert-Butyl-benzenesulfonyl)-(3-dimethylamino-phenyl)-amino]-N-ethyl-N-pyridin-2-ylmethyl-acetamide;
2-[(4-tert-Butyl-benzenesulfonyl)-(3-dimethylamino-phenyl)-amino]-N-ethyl-N-pyridin-3-ylmethyl-acetamide;
2-[(4-tert-Butyl-benzenesulfonyl)-(3-dimethylamino-phenyl)-amino]-N-ethyl-N-thiazol-2-ylmethyl-acetamide;
2-[(4-tert-Butyl-benzenesulfonyl)-(3-dimethylamino-phenyl)-amino]-N-ethyl-N-(6-methyl-pyridin-2-ylmethyl)-acetamide;
2-[(4-tert-Butyl-benzenesulfonyl)-p-tolyl-amino]-N-(4-dimethylamino-benzyl)-N-ethyl-acetamide;
2-[(4-tert-Butyl-benzenesulfonyl)-p-tolyl-amino]-N-ethyl-N-(3-hydroxy-benzyl)-acetamide;
2-{(4-tert-Butyl-benzenesulfonyl)-[(ethyl-thiazol-2-ylmethyl-carbamoyl)-methyl]-amino}-benzamide;
2-((4-tert-Butyl-benzenesulfonyl)-{[ethyl-(6-methyl-pyridin-2-ylmethyl)-carbamoyl]-methyl}-amino)-benzamide;
2-[[(Benzyl-ethyl-carbamoyl)-methyl]-(4-tert-butyl-benzenesulfonyl)-amino]-benzamide;
2-[(4-tert-Butyl-benzenesulfonyl)-(1H-indazol-6-yl)-amino]-N,N-diethyl-acetamide;
N-Benzyl-2-[(4-tert-butyl-benzenesulfonyl)-(1H-indazol-6-yl)-amino]-N-(2-hydroxy-ethyl)-acetamide;
2-[(4-tert-Butyl-benzenesulfonyl)-(1H-indazol-6-yl)-amino]-N-ethyl-N-thiazol-2-ylmethyl-acetamide;
2-[(4-tert-Butyl-benzenesulfonyl)-(1H-indazol-6-yl)-amino]-N-ethyl-N-(6-methyl-pyridin-2-ylmethyl)-acetamide;
2-[(4-tert-Butyl-benzenesulfonyl)-(1H-indazol-6-yl)-amino]-N-ethyl-N-(2-hydroxy-ethyl)-acetamide;
2-[(4-tert-Butyl-benzenesulfonyl)-(1H-indazol-6-yl)-amino]-N-ethyl-N-pyridin-2-ylmethyl-acetamide;
2-[(4-tert-Butyl-benzenesulfonyl)-(1H-indazol-6-yl)-amino]-N-ethyl-N-pyridin-3-ylmethyl-acetamide;
2-[(4-tert-Butyl-benzenesulfonyl)-p-tolyl-amino]-N-(2-hydroxy-ethyl)-N-pyridin-2-ylmethyl-acetamide;
2-[(4-tert-Butyl-benzenesulfonyl)-p-tolyl-amino]-N-(3-hydroxy-propyl)-N-pyridin-2-ylmethyl-acetamide;
2-[(4-tert-Butyl-benzenesulfonyl)-(3-dimethylamino-phenyl)-amino]-N-(2-hydroxy-ethyl)-N-pyridin-2-ylmethyl-acetamide;
2-[(4-tert-Butyl-benzenesulfonyl)-(3-dimethylamino-phenyl)-amino]-N-(3-hydroxy-propyl)-N-pyridin-2-ylmethyl-acetamide;
2-[(4-tert-Butyl-benzenesulfonyl)-p-tolyl-amino]-N-(6-dimethylamino-pyridin-2-ylmethyl)-N-ethyl-acetamide;
2-[(4-tert-Butyl-benzenesulfonyl)-p-tolyl-amino]-N-cyclopropyl-N-(3-methoxy-benzyl)-acetamide;
2-[(4-tert-Butyl-benzenesulfonyl)-p-tolyl-amino]-N-cyclopropyl-N-(3,4-dimethoxy-benzyl)-acetamide;
2-[(4-tert-Butyl-benzenesulfonyl)-p-tolyl-amino]-N-cyclopropyl-N-(3-methyl-benzyl)-acetamide;
2-[(4-tert-Butyl-benzenesulfonyl)-p-tolyl-amino]-N-cyclopropyl-N-(3,5-dimethoxy-benzyl)-acetamide;
2-[(4-tert-Butyl-benzenesulfonyl)-p-tolyl-amino]-N-methyl-N-pyridin-3-ylmethyl-acetamide;
2-[(4-tert-Butyl-benzenesulfonyl)-quinolin-6-yl-amino]-N-cyclopropyl-N-(3-methoxy-benzyl)-acetamide;
2-[(4-tert-Butyl-benzenesulfonyl)-(3-dimethylamino-phenyl)-amino]-N-cyclopropyl-N-(3-methoxy-benzyl)-acetamide;

2-[(4-tert-Butyl-benzenesulfonyl)-(3-dimethylamino-phenyl)-amino]-N-cyclopropyl-N-(3-methyl-benzyl)-acetamide;
N-Ethyl-2-[(5-isopropyl-pyridine-2-sulfonyl)-p-tolyl-amino]-N-pyridin-2-ylmethyl-acetamide;
N-Ethyl-2-[(5-isopropyl-pyridine-2-sulfonyl)-p-tolyl-amino]-N-(6-methyl-pyridin-2-ylmethyl)-acetamide;
N-Ethyl-2-[(2-methoxy-phenyl)-(toluene-2-sulfonyl)-amino]-N-thiazol-2-ylmethyl-acetamide;
N-Ethyl-2-[(2-methoxy-phenyl)-(toluene-2-sulfonyl)-amino]-N-(6-methyl-pyridin-2-ylmethyl)-acetamide;
N-Benzyl-N-(2-hydroxy-ethyl)-2-[(2-methoxy-phenyl)-(toluene-2-sulfonyl)-amino]-acetamide;
N-Ethyl-2-[(2-methoxy-phenyl)-(toluene-2-sulfonyl)-amino]-N-pyridin-3-ylmethyl-acetamide;
N-Ethyl-2-[(2-methoxy-phenyl)-(toluene-2-sulfonyl)-amino]-N-pyridin-2-ylmethyl-acetamide;
N-(2-Cyano-ethyl)-N-ethyl-2-[(2-methoxy-phenyl)-(toluene-2-sulfonyl)-amino]-acetamide;
N-Ethyl-2-[(2-methoxy-phenyl)-(toluene-2-sulfonyl)-amino]-N-(1-methyl-1H-pyrrol-2-ylmethyl)-acetamide;
N-Ethyl-N-(4-hydroxy-benzyl)-2-[(2-methoxy-phenyl)-(toluene-2-sulfonyl)-amino]-acetamide;
N-Ethyl-N-(3-hydroxy-benzyl)-2-[(2-methoxy-phenyl)-(toluene-2-sulfonyl)-amino]-acetamide;
N-Ethyl-2-[(6-methoxy-pyridin-3-yl)-(toluene-2-sulfonyl)-amino]-N-thiazol-2-ylmethyl-acetamide;
N-Ethyl-2-[(6-methoxy-pyridin-3-yl)-(toluene-2-sulfonyl)-amino]-N-(6-methyl-pyridin-2-ylmethyl)-acetamide;
N-Benzyl-N-(2-hydroxy-ethyl)-2-[(6-methoxy-pyridin-3-yl)-(toluene-2-sulfonyl)-amino]-acetamide;
N-Ethyl-2-[(6-methoxy-pyridin-3-yl)-(toluene-2-sulfonyl)-amino]-N-pyridin-3-ylmethyl-acetamide;
N-Ethyl-2-[(6-methoxy-pyridin-3-yl)-(toluene-2-sulfonyl)-amino]-N-pyridin-2-ylmethyl-acetamide;
N-(2-Cyano-ethyl)-N-ethyl-2-[(6-methoxy-pyridin-3-yl)-(toluene-2-sulfonyl)-amino]-acetamide;
N-Ethyl-2-[(6-methoxy-pyridin-3-yl)-(toluene-2-sulfonyl)-amino]-N-(1-methyl-1H-pyrrol-2-ylmethyl)-acetamide;
N-Benzyl-N-(2-hydroxy-ethyl)-2-[(toluene-2-sulfonyl)-p-tolyl-amino]-acetamide;
N-Ethyl-N-pyridin-3-ylmethyl-2-[(toluene-2-sulfonyl)-p-tolyl-amino]-acetamide;
N-Ethyl-N-thiazol-2-ylmethyl-2-[(toluene-2-sulfonyl)-p-tolyl-amino]-acetamide;
N-Ethyl-N-(6-methyl-pyridin-2-ylmethyl)-2-[(toluene-2-sulfonyl)-p-tolyl-amino]-acetamide;
N-(2-Hydroxy-ethyl)-N-pyridin-2-ylmethyl-2-[(toluene-2-sulfonyl)-p-tolyl-amino]-acetamide;
N-Ethyl-2-[(3-methyl-pyridine-2-sulfonyl)-p-tolyl-amino]-N-pyridin-2-ylmethyl-acetamide;
N-Ethyl-2-[(3-methyl-pyridine-2-sulfonyl)-m-tolyl-amino]-N-(6-methyl-pyridin-2-ylmethyl)-acetamide;
N-Ethyl-2-[(2-methoxy-phenyl)-(3-methyl-pyridine-2-sulfonyl)-amino]-N-(6-methyl-pyridin-2-ylmethyl)-acetamide;
N-Benzyl-N-ethyl-2-[(2-methoxy-phenyl)-(3-methyl-pyridine-2-sulfonyl)-amino]-acetamide;
N-Ethyl-N-pyridin-2-ylmethyl-2-[(1,2,3,4-tetrahydro-isoquinoline-7-sulfonyl)-p-tolyl-amino]-acetamide;
N-Ethyl-2-[(5-isopropyl-pyridine-2-sulfonyl)-m-tolyl-amino]-N-(6-methyl-pyridin-2-ylmethyl)-acetamide;
N-Ethyl-2-[(5-isopropyl-pyridine-2-sulfonyl)-(2-methoxy-phenyl)-amino]-N-(6-methyl-pyridin-2-ylmethyl)-acetamide;
N-Benzyl-N-ethyl-2-[(5-isopropyl-pyridine-2-sulfonyl)-(2-methoxy-phenyl)-amino]-acetamide;
N-Ethyl-2-[(5-isopropyl-pyridine-2-sulfonyl)-(6-methoxy-pyridin-3-yl)-amino]-N-pyridin-2-ylmethyl-acetamide;
N-Ethyl-2-[(5-isopropyl-pyridine-2-sulfonyl)-(6-methoxy-pyridin-3-yl)-amino]-N-(6-methyl-pyridin-2-ylmethyl)-acetamide;
N-Benzyl-N-ethyl-2-[(5-isopropyl-pyridine-2-sulfonyl)-(6-methoxy-pyridin-3-yl)-amino]-acetamide;
2-[(4-tert-Butyl-benzenesulfonyl)-(6-methyl-pyridin-3-yl)-amino]-N-ethyl-N-pyridin-2-ylmethyl-acetamide;
N-Benzyl-2-[(4-tert-butyl-benzenesulfonyl)-(6-methyl-pyridin-3-yl)-amino]-N-ethyl-acetamide;
N-Ethyl-2-[(6-methoxy-pyridin-3-yl)-(3-methyl-pyridine-2-sulfonyl)-amino]-N-pyridin-2-ylmethyl-acetamide;
N-Ethyl-2-[(6-methoxy-pyridin-3-yl)-(3-methyl-pyridine-2-sulfonyl)-amino]-N-(6-methyl-pyridin-2-ylmethyl)-acetamide;
N-Benzyl-N-ethyl-2-[(6-methoxy-pyridin-3-yl)-(3-methyl-pyridine-2-sulfonyl)-amino]-acetamide;
2-{(3-Dimethylamino-phenyl)-[4-(1-hydroxy-1-methyl-ethyl)-benzenesulfonyl]-amino}-N-ethyl-N-pyridin-2-ylmethyl-acetamide;

Examples of particularly preferred compounds of formula (I) are:
2-[(4-tert-Butyl-benzenesulfonyl)-p-tolyl-amino]-N,N-diethyl-acetamide;
2-[(4-tert-Butyl-benzenesulfonyl)-(4-methoxy-phenyl)-amino]-N,N-diethyl-acetamide;
2-[(4-tert-Butyl-benzenesulfonyl)-(3-methoxy-phenyl)-amino]-N,N-diethyl-acetamide;
2-[(4-tert-Butyl-benzenesulfonyl)-m-tolyl-amino]-N,N-diethyl-acetamide;
2-[(6-Dimethylamino-pyridine-3-sulfonyl)-p-tolyl-amino]-N-ethyl-N-pyridin-2-ylmethyl-acetamide;
N-Benzyl-2-[(4-tert-butyl-benzenesulfonyl)-p-tolyl-amino]-N-ethyl-acetamide;
2-[(4-tert-Butyl-benzenesulfonyl)-p-tolyl-amino]-N-ethyl-N-pyridin-4-ylmethyl-acetamide;
N,N-Diethyl-2-[(2-methoxy-phenyl)-(toluene-2-sulfonyl)-amino]-acetamide;
N-Benzyl-N-ethyl-2-[(6-methoxy-pyridin-3-yl)-(toluene-2-sulfonyl)-amino]-acetamide;
N-Benzyl-N-ethyl-2-[(2-methoxy-phenyl)-(toluene-2-sulfonyl)-amino]-acetamide;
N-Benzyl-2-[(4-tert-butyl-benzenesulfonyl)-(2-methoxy-phenyl)-amino]-N-ethyl-acetamide;
N-Benzyl-N-ethyl-2-[(6-methoxy-pyridin-3-yl)-(naphthalene-2-sulfonyl)-amino]-acetamide;
2-[(4-tert-Butyl-benzenesulfonyl)-p-tolyl-amino]-N-ethyl-N-(2-hydroxy-ethyl)-acetamide;
2-[(3-Chloro-4-methyl-benzenesulfonyl)-p-tolyl-amino]-N,N-diethyl-acetamide;
N-Benzyl-2-[(4-tert-butyl-benzenesulfonyl)-p-tolyl-amino]-N-(2-hydroxy-ethyl)-acetamide;
2-[(4-tert-Butyl-benzenesulfonyl)-p-tolyl-amino]-N-(2-cyano-ethyl)-N-ethyl-acetamide;
2-[(4-tert-Butyl-benzenesulfonyl)-p-tolyl-amino]-N-ethyl-N-pyridin-2-ylmethyl-acetamide;
2-[(4-tert-Butyl-benzenesulfonyl)-p-tolyl-amino]-N-ethyl-N-pyridin-3-ylmethyl-acetamide;
2-[(4-tert-Butyl-benzenesulfonyl)-p-tolyl-amino]-N-ethyl-N-(6-methyl-pyridin-2-ylmethyl)-acetamide;
2-[(4-tert-Butyl-benzenesulfonyl)-p-tolyl-amino]-N-ethyl-N-thiazol-2-ylmethyl-acetamide;
2-[(4-tert-Butyl-benzenesulfonyl)-(3-dimethylamino-phenyl)-amino]-N,N-diethyl-acetamide;
2-[(4-tert-Butyl-benzenesulfonyl)-(3-dimethylamino-phenyl)-amino]-N-ethyl-N-pyridin-2-ylmethyl-acetamide;

2-[(4-tert-Butyl-benzenesulfonyl)-(3-dimethylamino-phenyl)-amino]-N-ethyl-N-(6-methyl-pyridin-2-ylmethyl)-acetamide;
2-[(4-tert-Butyl-benzenesulfonyl)-p-tolyl-amino]-N-ethyl-N-(3-hydroxy-benzyl)-acetamide;
2-[(4-tert-Butyl-benzenesulfonyl)-(1H-indazol-6-yl)-amino]-N-ethyl-N-(6-methyl-pyridin-2-ylmethyl)-acetamide;
2-[(4-tert-Butyl-benzenesulfonyl)-(1H-indazol-6-yl)-amino]-N-ethyl-N-pyridin-2-ylmethyl-acetamide;
2-[(4-tert-Butyl-benzenesulfonyl)-p-tolyl-amino]-N-(2-hydroxy-ethyl)-N-pyridin-2-ylmethyl-acetamide;
2-[(4-tert-Butyl-benzenesulfonyl)-(3-dimethylamino-phenyl)-amino]-N-(2-hydroxy-ethyl)-N-pyridin-2-ylmethyl-acetamide;
2-[(4-tert-Butyl-benzenesulfonyl)-p-tolyl-amino]-N-cyclopropyl-N-(3-methoxy-benzyl)-acetamide;
2-[(4-tert-Butyl-benzenesulfonyl)-(3-dimethylamino-phenyl)-amino]-N-cyclopropyl-N-(3-methoxy-benzyl)-acetamide;
N-Ethyl-2-[(2-methoxy-phenyl)-(toluene-2-sulfonyl)-amino]-N-thiazol-2-ylmethyl-acetamide;
N-Benzyl-N-(2-hydroxy-ethyl)-2-[(2-methoxy-phenyl)-(toluene-2-sulfonyl)-amino]-acetamide;
N-Ethyl-2-[(2-methoxy-phenyl)-(toluene-2-sulfonyl)-amino]-N-pyridin-2-ylmethyl-acetamide;
N-Ethyl-N-(3-hydroxy-benzyl)-2-[(2-methoxy-phenyl)-(toluene-2-sulfonyl)-amino]-acetamide;
N-Ethyl-2-[(6-methoxy-pyridin-3-yl)-(toluene-2-sulfonyl)-amino]-N-(6-methyl-pyridin-2-ylmethyl)-acetamide;
N-Benzyl-N-(2-hydroxy-ethyl)-2-[(6-methoxy-pyridin-3-yl)-(toluene-2-sulfonyl)-amino]-acetamide;
N-Ethyl-2-[(6-methoxy-pyridin-3-yl)-(toluene-2-sulfonyl)-amino]-N-pyridin-3-ylmethyl-acetamide;
N-Ethyl-2-[(6-methoxy-pyridin-3-yl)-(toluene-2-sulfonyl)-amino]-N-pyridin-2-ylmethyl-acetamide;
N-Ethyl-2-[(2-methoxy-phenyl)-(3-methyl-pyridine-2-sulfonyl)-amino]-N-(6-methyl-pyridin-2-ylmethyl)-acetamide;
N-Benzyl-N-ethyl-2-[(2-methoxy-phenyl)-(3-methyl-pyridine-2-sulfonyl)-amino]-acetamide;
2-[(4-tert-Butyl-benzenesulfonyl)-(6-methyl-pyridin-3-yl)-amino]-N-ethyl-N-pyridin-2-ylmethyl-acetamide;
N-Benzyl-2-[(4-tert-butyl-benzenesulfonyl)-(6-methyl-pyridin-3-yl)-amino]-N-ethyl-acetamide;
N-Ethyl-2-[(6-methoxy-pyridin-3-yl)-(3-methyl-pyridine-2-sulfonyl)-amino]-N-(6-methyl-pyridin-2-ylmethyl)-acetamide;
N-Benzyl-N-ethyl-2-[(6-methoxy-pyridin-3-yl)-(3-methyl-pyridine-2-sulfonyl)-amino]-acetamide;

The present invention encompasses physiologically usable or pharmaceutically acceptable salts of compounds of formula (I). This encompasses salts with physiologically compatible mineral acids such as hydrochloric acid, sulphuric or phosphoric acid; or with organic acids such as formic acid, methanesulphonic acid, acetic acid, trifluoroacetic acid, citric acid, fumaric acid, maleic acid, tartaric acid, succinic acid or salicylic acid and the like. The compounds of formula (I) which are acidic can also form salts with physiologically compatible bases.

Examples of such salts are alkali metal, alkali earth metal, ammonium and alkylammoniumsalts such as Na, K, Ca or tetraalkylammonium salt. The compounds of formula (I) can also be present in the form of a zwitterion.

The present invention encompasses also solvation complexes of compounds of general formula (I). The solvation can be effected in the course of the manufacturing process or can take place separately, e.g. as a consequence of hygroscopic properties of an initially anhydrous compound of general formula (I).

The present invention further encompasses different morphological forms, e.g. crystalline forms, of compounds of general formula (I) and their salts and solvation complexes. Particular heteromorphs may exhibit different dissolution properties, stability profiles, and the like, and are all included in the scope of the present invention.

The compounds of formula (I) might have one or several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates and the meso-forms.

Preferred compounds as described above have $IC_{50}$ values below 100 nM, particularly preferred compounds have $IC_{50}$ values below 20 nM which have been determined with the FLIPR (Fluorometric Imaging Plates Reader) method described in the beginning of the experimental section.

The compounds of formula (I) and their pharmaceutically usable salts can be used for the treatment of diseases or disorders where an antagonist of a human orexin receptor is required such as obesity, diabetes, prolactinoma, narcolepsy, insomnia, sleep apnea, parasomnia, depression, anxiety, addictions, schizophrenia and dementia or any other disease related to orexin dysfunction.

The compounds of formula (I) and their pharmaceutically usable salts are particularly useful for the treatment of disturbed homeostasis and eating disorders (e.g. bulimia, obesity, food abuse, compulsive eating or irritable bowel syndrome), as well as disturbed sleep/wake schedule, sleep disorders (e.g. insomnias, apneas, dystonias), stress-related diseases (e.g. anxiety, mood and blood pressure disorders), or any other disease related to orexin dysfunction.

The compounds of formula (I) and their pharmaceutically usable salts can be used as medicament (e.g. in the form of pharmaceutical preparations). The pharmaceutical preparations can be administered enterally, such as orally (e.g. in the form of tablets, coated tablets, dragées, hard and soft gelatine capsules, solutions, emulsions or suspensions), nasally (e.g. in the form of nasal sprays) or rectally (e.g. in the form of suppositories). However, the administration can also be effected parenterally, such as intramuscularly or intravenously (e.g. in the form of injection solutions), or topically, e.g. in the form of ointments, creams or oils.

The compounds of formula (I) and their pharmaceutically usable salts can be processed with pharmaceutically inert, inorganic or organic adjuvants for the production of tablets, coated tablets, dragées, and hard gelatine capsules. Lactose, corn starch or derivatives thereof, talc, stearic acid or its salts etc. can be used, for example, as such adjuvants for tablets, dragées, and hard gelatine capsules. Suitable adjuvants for soft gelatine capsules, are, for example, vegetable oils, waxes, fats, semi-solid substances and liquid polyols, etc. Suitable adjuvants for the production of solutions and syrups are, for example, water, polyols, saccharose, invert sugar, glucose, etc. Suitable adjuvants for injection solutions are, for example, water, alcohols, polyols, glycerol, vegetable oils, etc. Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. The compounds of formula (I) may also be used in combination with one or more other therapeutically useful substances. Examples are anorectic drugs like fenfluramine and related substances; lipase inhibitors like orlistat and related substances; antidepressants like fluoxetine and related substances; anxiolytics like alprazolam and related substances; sleep-inducers like zopiclone and related substances; or any other therapeutically useful substance.

The dosage of compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to 1000 mg, especially about 50 mg to about 500 mg, comes into consideration.

The pharmaceutical preparations conveniently contain about 1-500 mg, preferably 5-200 mg of a compound of formula (I).

The compounds of general formula (I) of the present invention are prepared according to the general sequence of reactions outlined in the schemes below, wherein A, B, $R^1$, $R^2$ are as defined in formula (I) above. As the case may be any compound obtained with one or more optically active carbon atom may be resolved into pure enantiomers or diastereomers, mixtures of enantiomers or diastereomers, diastereomeric racemates and the meso-forms in a manner known per se.

The compounds obtained may also be converted into a pharmaceutically acceptable salt thereof in a manner known per se.

The compounds of formula (I) may be prepared as single compounds or as libraries of compounds comprising at least 2, typically 5 to 200 compounds of formula (I).

Compound libraries are prepared by multiple parallel synthesis using solution phase chemistry.

The compounds of formula (I) have been prepared by following one out of three possible synthetic pathways. The first pathway starts with the reaction of an amine B—$NH_2$ with an α-bromoacetamide, which might be synthesised starting from bromoacetyl bromide and an amine $NHR^1(CH_2R^2)$ either in situ or separately. In a second step the respective aminoacetamide was reacted with a sulfonyl chloride A-$SO_2$Cl (Scheme 1).

Scheme 1

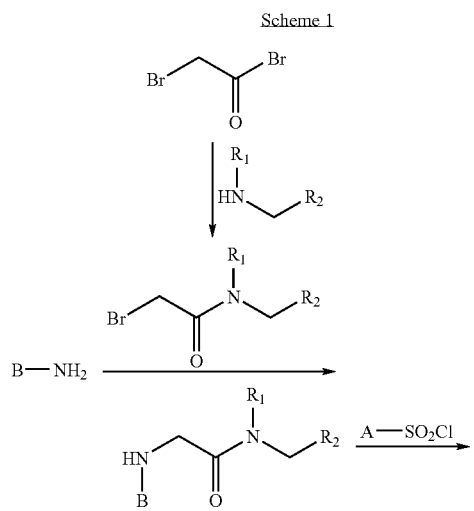

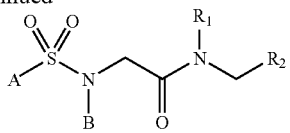

The second synthetic route starts with the reaction of an amine B—$NH_2$ with a sulfonyl chloride A-$SO_2$Cl. From the intermediate sulfonamides the target molecules can be obtained by reaction with the respective α-bromoacetamide (Scheme 2).

Scheme 2

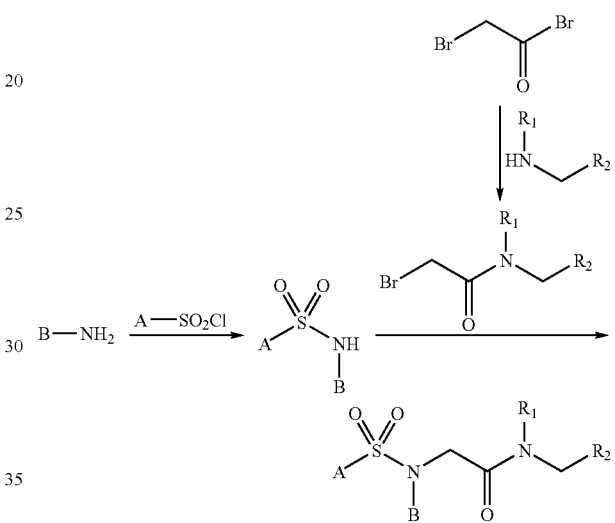

In a third pathway a sulfonamide is synthesized starting from an amine B—$NH_2$ and a sulfonyl chloride A-$SO_2$Cl. The obtained sulfonamide is transformed to a t-butyl- or methyl acetate derivative by reaction with either tert-butyl bromoacetate or methyl bromoacetate. The ester is hydrolyzed and the obtained acid is coupled with an amine $NHR^1(CH_2R^2)$ to give the desired amide (Scheme 3).

Scheme 3

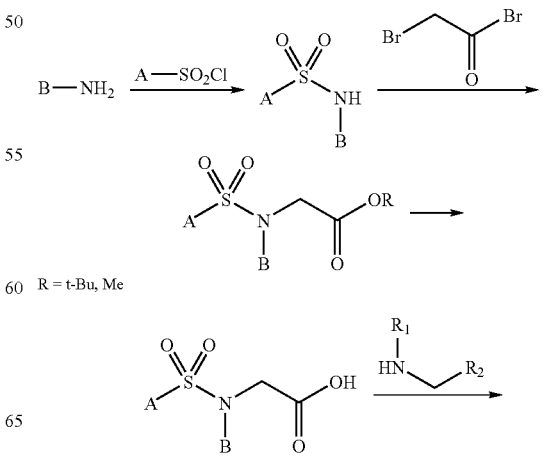

R = t-Bu, Me

-continued

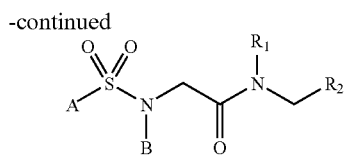

EXPERIMENTAL SECTION

| Abbreviations: | |
|---|---|
| bp | Boiling point |
| BSA | Bovine serum albumine |
| CHO | Chinese hamster ovary |
| d | Day(s) |
| DCM | Dichloromethane |
| DMSO | Dimethylsulfoxide |
| DIPEA | N,N-Diisopropylethylamine |
| EDC | 1-(3-Dimethylaminopropyl)-3-ethylcarbodiimide |
| ES | Electron spray |
| ether | Diethylether |
| FCS | Foetal calf serum |
| FLIPR | Fluorescent imaging plate reader |
| h | Hour(s) |
| HBSS | Hank's balanced salt solution |
| HEPES | 4-(2-Hydroxyethyl)-piperazine-1-ethanesulfonic acid |
| HPLC | High pressure/performance liquid chromatography |
| MS | Mass spectroscopy |
| LC | Liquid chromatography |
| min | Minute(s) |
| $R_t$ | retention time |
| RT | Room temperature |
| TBTU | O-Benzotriazol-1-yl-N,N,N',N'-tetramethyluronium tetrafluoroborate |
| TFA | Trifluoroacetic acid |
| THF | Tetrahydrofuran |

I. Biology

Determination of Orexin Receptor Antagonistic Activity

The Orexin receptor antagonistic activity of the compounds of formula (I) was determined in accordance with the following experimental method.

Experimental Method

Intracellular Calcium Measurements

Chinese hamster ovary (CHO) cells expressing the human orexin-1 receptor and the human orexin-2 receptor, respectively, were grown in culture medium (Ham F-12 with L-Glutamine) containing 300 µg/ml G418, 100 U/ml penicillin, 100 µg/ml streptomycin and 10% inactivated foetal calf serum (FCS).

The cells were seeded at 80,000 cells/well into 96-well black clear bottom sterile plates (Costar) which had been precoated with 1% gelatine in Hanks' Balanced Salt Solution (HBSS). All reagents were from Gibco BRL.

The seeded plates were incubated overnight at 37° C. in 5% $CO_2$.

Human orexin-A as an agonist was prepared as 1 mM stock solution in methanol:water (1:1), diluted in HBSS containing 0.1% bovine serum albumin (BSA) and 2 mM HEPES for use in the assay at a final concentration of 10 nM.

Antagonists were prepared as 10 mM stock solution in DMSO, then diluted in 96-well plates, first in DMSO, then in HBSS containing 0.1% bovine serum albumin (BSA) and 2 mM HEPES.

On the day of the assay, 100 µl of loading medium (HBSS containing 1% FCS, 2 mM HEPES, 5 mM probenecid (Sigma) and 3 µM of the fluorescent calcium indicator fluo-3 AM (1 mM stock solution in DMSO with 10% pluronic acid) (Molecular Probes) was added to each well.

The 96-well plates were incubated for 60 min at 37° C. in 5% $CO_2$. The loading solution was then aspirated and cells were washed 3 times with 200 µl HBSS containing 2.5 mM probenecid, 0.1% BSA, 2 mM HEPES. 100 µl of that same buffer was left in each well. Within the Fluorescent Imaging Plate Reader (FLIPR, Molecular Devices), antagonists were added to the plate in a volume of 50 µl, incubated for 20 min and finally 100 µl of agonist was added. Fluorescence was measured for each well at 1 second intervals, and the height of each fluorescence peak was compared to the height of the fluorescence peak induced by 10 nM orexin-A with buffer in place of antagonist. For each antagonist, $IC_{50}$ value (the concentration of compound needed to inhibit 50% of the agonistic response) was determined. Selected compounds are displayed in Table 1.

TABLE 1

| | $OX_1$: $IC_{50}$ [nM] | $OX_2$: $IC_{50}$ [nM] |
|---|---|---|
| Example 46 | 898 | 5 |
| Example 47 | 354 | 4 |
| Example 63 | >10000 | 3 |
| Example 66 | 1026 | 4 |
| Example 71 | 417 | 5 |
| Example 87 | 56 | 8 |
| Example 111 | 331 | 5 |
| Example 158 | 840 | 5 |
| Example 160 | 8636 | 2 |
| Example 162 | >10000 | 2 |
| Example 163 | >10000 | 4 |
| Example 185 | 4269 | 4 |
| Example 207 | 5368 | 4 |

II. Chemistry

The following examples illustrate the preparation of pharmacologically active compounds of the invention but do not at all limit the scope thereof.

All temperatures are stated in ° C.

All analytical and preparative HPLC investigations were performed using RP-C18 based columns.

A Synthesis of Starting Materials

A.1 Synthesis of Amines

A1.1 Synthesis of Amines via Reductive Amination (General Procedure)

A solution of the respective amine in THF (2.0 mol/L, 5.0 mL) was added to a solution of the respective aldehyde (10.0 mmol) in methanol (20 mL). Activated molecular sieves (4 Å) were added and the reaction mixture was stirred for 16 h. After addition of sodium borohydride (12 mmol) the solution was stirred for 3 h, treated with water (10 mL), stirred for 1 h and purified by ion-exchange chromatography [amberlyst 15, methanol/ammonium hydroxide solution (10 mol/L) 1:1]. After removal of methanol in vacuo the aqueous layer was extracted with ethyl acetate (3×100 mL). The solvents were removed in vacuo, the residue was dissolved in ethanol and the product was precipitated by addition of a solution of hydrogen chloride in ether (2.0 mol/L). The following amines were obtained:

3-Ethylaminomethyl-phenol

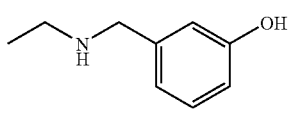

prepared by reaction of ethylamine with 3-hydroxy-benzaldehyde

LC-MS: rt=0.55 min, 152 (M+1, ES+).

Ethyl-quinolin-3-ylmethyl-amine

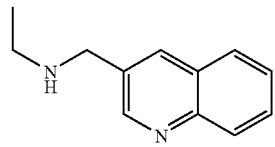

prepared by reaction of ethylamine with quinoline-3-carbaldehyde

LC-MS: rt=0.58 min, 187 (M+1, ES+).

Ethyl-quinolin-4-ylmethyl-amine

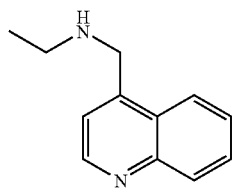

prepared by reaction of ethylamine with quinoline-4-carbaldehyde

LC-MS: rt=0.50 min, 187 (M+1, ES+).

(4-Ethylaminomethyl-phenyl)-dimethyl-amine

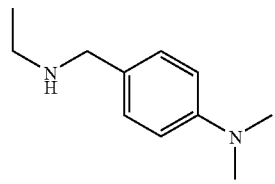

prepared by reaction of ethylamine with 4-dimethylamino-benzaldehyde

LC-MS: rt=0.49 min, 179 (M+1, ES+).

4-Ethylaminomethyl-phenol

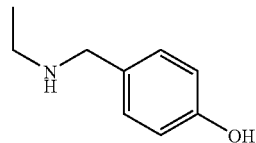

prepared by reaction of ethylamine with 4-hydroxy-benzaldehyde

LC-MS: rt=0.54 min, 152 (M+1, ES+).

Ethyl-(1H-imidazol-2-ylmethyl)-amine

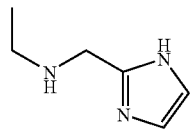

prepared by reaction of ethylamine with 1H-imidazole-2-carbaldehyde

LC-MS: rt=0.16 min, 126 (M+1, ES+).

Ethyl-(6-methyl-pyridin-2-ylmethyl)-amine

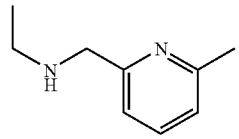

prepared by reaction of ethylamine with 6-methyl-pyridine-2-carbaldehyde

LC-MS: rt=0.48 min, 151 (M+1, ES+).

Ethyl-(3H-imidazol-4-ylmethyl)-amine

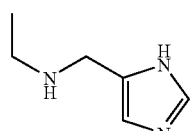

prepared by reaction of ethylamine with 3H-imidazole-4-carbaldehyde

LC-MS: rt=0.16 min, 126 (M+1, ES+).

Ethyl-thiazol-2-ylmethyl-amine

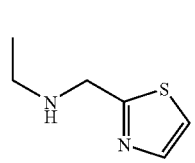

prepared by reaction of ethylamine with thiazole-2-carbaldehyde

LC-MS: rt=0.17 min, 143 (M+1, ES+).

Ethyl-(1H-indol-3-ylmethyl)-amine

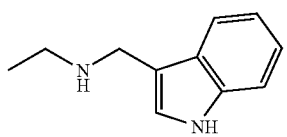

prepared by reaction of ethylamine with 1H-indole-3-carbaldehyde

LC-MS: rt=0.75 min, 175 (M+1, ES+).

Ethyl-pyridin-2-ylmethyl-amine

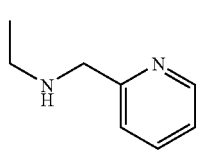

prepared by reaction of ethylamine with pyridine-2-carbaldehyde

LC-MS: rt=0.47 min, 137 (M+1, ES+).

Ethyl-pyridin-3-ylmethyl-amine

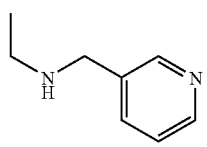

prepared by reaction of ethylamine with pyridine-3-carbaldehyde

LC-MS: rt=0.16 min, 137 (M+1, ES+).

4-Ethylaminomethyl-benzonitrile

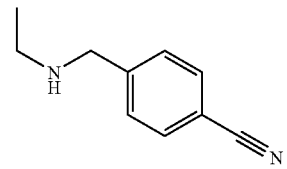

prepared by reaction of ethylamine with 4-formyl-benzonitrile

LC-MS: rt=0.62 min, 161 (M+1, ES+).

Ethyl-(1-methyl-1H-pyrrol-2-ylmethyl)-amine

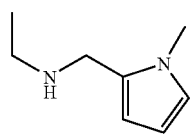

prepared by reaction of ethylamine with 1-methyl-1H-pyrrole-2-carbaldehyde

LC-MS: rt=0.56 min, 139 (M+1, ES+).

2-[(Pyridin-2-ylmethyl)-amino]-ethanol

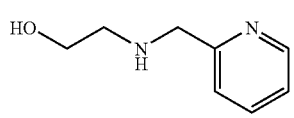

prepared by reaction of 2-amino-ethanol with pyridine-2-carbaldehyde

LC-MS: rt=0.16 min, 153 (M+1, ES+).

3-[(Pyridin-2-ylmethyl)-amino]-propan-1-ol

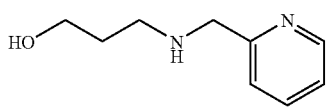

prepared by reaction of 3-amino-propan-1-ol with pyridine-2-carbaldehyde

LC-MS: rt=0.16 min, 167 (M+1, ES+).

2-[(Quinolin-2-ylmethyl)-amino]-ethanol

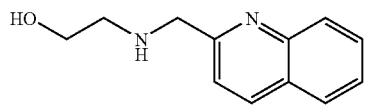

prepared by reaction of 2-amino-ethanol with quinoline-2-carbaldehyde

LC-MS: rt=0.53 min, 203 (M+1, ES+).

3-[(Quinolin-2-ylmethyl)-amino]-propan-1-ol

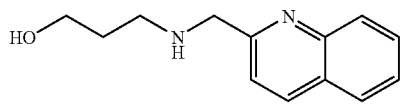

prepared by reaction of 3-amino-propan-1-ol with quinoline-2-carbaldehyde

LC-MS: rt=0.56 min, 217 (M+1, ES+).

Ethyl-quinolin-2-ylmethyl-amine

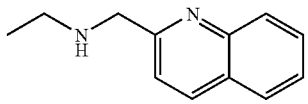

prepared by reaction of ethylamine with quinoline-2-carbaldehyde

LC-MS: rt=0.58 min, 187 (M+1, ES+).

A1.2 Synthesis of 6-Ethylaminomethyl-pyridin-2-ylamines

A1.2.1 Synthesis of 6-Bromo-pyridine-2-carboxylic acid ethylamide

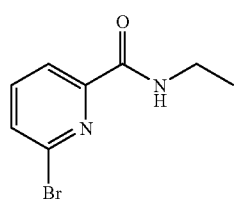

TBTU (6.5 mmol) was added to a solution of 6-bromo-pyridine-2-carboxylic acid (5.0 mmol) in DMF (30 mL). A solution of ethylamine in THF (1.0 mol/L, 5.0 mL) and DIPEA (15.0 mmol) were added and the reaction mixture was stirred for 16 h. Water (100 mL) and ethyl acetate (100 mL) were added, the layers were separated, and the aqueous layer was extracted with ethyl acetate (2×100 mL). The combined organic layers were washed with brine (100 mL), dried over Na$_2$SO$_4$, and concentrated in vacuo to give 1.1 g (4.8 mmol, 96%) of the desired amide as a yellow oil which was used without further purification.

LC-MS: rt=0.85 min, 229 (M+1, ES+).

A1.2.2 Synthesis of 6-Amino-pyridine-2-carboxylic acid ethylamides (General Procedure)

A solution of the respective amine in methanol (2.0 mol/L, 5.0 mL) was added to 6-bromo-pyridine-2-carboxylic acid ethylamide (4.38 mmol). The reaction mixture was heated for 5 min in a microwave oven at 150 W and purified by preparative HPLC chromatography to give the following aminopyridines:

6-(Ethyl-methyl-amino)-pyridine-2-carboxylic acid ethylamide

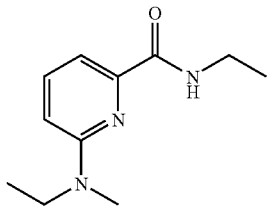

prepared by reaction of ethyl-methyl-amine with 6-bromo-pyridine-2-carboxylic acid ethylamide LC-MS: rt=0.82 min, 208 (M+1, ES+).

6-Dimethylamino-pyridine-2-carboxylic acid ethylamide

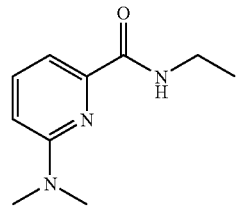

prepared by reaction of dimethyl-amine with 6-bromo-pyridine-2-carboxylic acid ethylamide LC-MS: rt=0.72 min, 194 (M+1, ES+).

6-Ethylamino-pyridine-2-carboxylic acid ethylamide

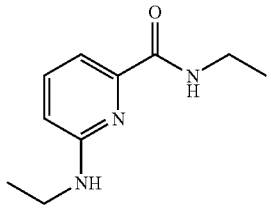

prepared by reaction of ethylamine with 6-bromo-pyridine-2-carboxylic acid ethylamide; in contrast to the general procedure the reaction was carried out by heating a solution of the starting materials in ethanol/water for 72 h at 100° C. in an autoclave LC-MS: rt=0.55 min, 194 (M+1, ES+).

A1.2.3 Synthesis of 6-Ethylaminomethyl-pyridin-2-ylamines (General Procedure)

Lithium aluminum hydride (7.6 mmol) was added to a solution of the respective 6-amino-pyridine-2-carboxylic acid ethylamide (3.8 mmol) in THF (10 mL). The reaction mixture was stirred for 2 h at RT and for 7 h at reflux, allowed to reach RT, treated with water (0.50 mL), NaOH solution (2.0 mol/L, 0.50 mL) and water (1.50 mL) and filtered. The residue washed with ethyl acetate (3×20 mL) and the filtrate was dried over $Na_2SO_4$ and concentrated in vacuo to give the following pyridine derivatives:

Ethyl-(6-ethylaminomethyl-pyridin-2-yl)-methyl-amine

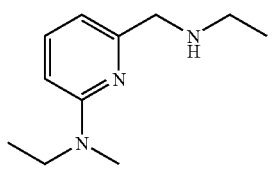

prepared by reduction of 6-(ethyl-methyl-amino)-pyridine-2-carboxylic acid ethylamide
LC-MS: rt=0.50 min, 194 (M+1, ES+).

(6-Ethylaminomethyl-pyridin-2-yl)-dimethyl-amine

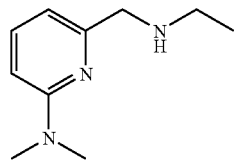

prepared by reduction of 6-dimethylamino-pyridine-2-carboxylic acid ethylamide
LC-MS: rt=0.42 min, 180 (M+1, ES+).

Ethyl-(6-ethylaminomethyl-pyridin-2-yl)-amine

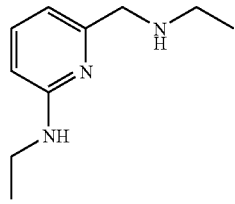

prepared by reduction of 6-ethylamino-pyridine-2-carboxylic acid ethylamide
LC-MS: rt=0.46 min, 180 (M+1, ES+).

A1.3 Synthesis of Benzyl-cyclopropyl-amines (General Procedure)

Cyclopropylamine (30.0 mmol) was added to a solution of the respective benzaldehyde (30.0 mmol) in methanol (30 mL). After 2 h sodium borohydride (30.0 mmol) was added. The reaction mixture was stirred for 2 h, treated with an aqueous NaOH-solution (1.0 mol/L, 2.0 mL), and concentrated in vacuo. Ethyl acetate (100 mL) and an aqueous NaOH-solution (1.0 mol/L, 50 mL) were added, and the layers were separated. The organic layer washed with an aqueous NaOH-solution (1.0 mol/L, 30 mL) and brine (30 mL), dried over $Na_2SO_4$, and concentrated in vacuo to give the following amines which were used without further purification:

Cyclopropyl-(3,4-dimethoxy-benzyl)-amine

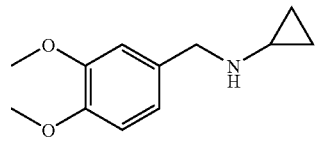

prepared by reaction of cyclopropylamine with 3,4-dimethoxy-benzaldehyde
LC-MS: rt=0.67 min, 208 (M+1, ES+).

Cyclopropyl-(3-methyl-benzyl)-amine

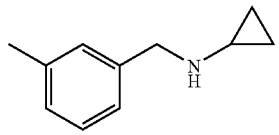

prepared by reaction of cyclopropylamine with 3-methyl-benzaldehyde
LC-MS: rt=0.53 min, 162 (M+1, ES+).

Cyclopropyl-(2,5-dichloro-benzyl)-amine

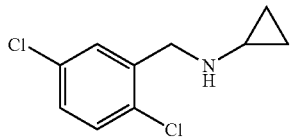

prepared by reaction of cyclopropylamine with 2,5-dichloro-benzaldehyde.

Cyclopropyl-(3-methoxy-benzyl)-amine

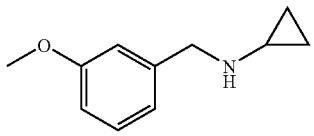

prepared by reaction of cyclopropylamine with 3-methoxy-benzaldehyde

LC-MS: rt=0.52 min, 178 (M+1, ES+).

A.2 Synthesis of Sulfonyl Chlorides

A.2.1 Synthesis of 6-Dimethylamino-pyridine-3-sulfonyl chloride

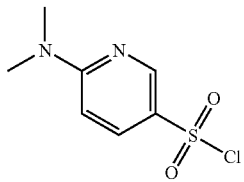

(5-Bromo-pyridin-2-yl)-dimethyl-amine

N-Bromosuccinimide (190 mmol) was added portionwise to a solution of 2-(dimethylamino)-pyridine (200 mmol) in DCM (1.0 L). After 10 min a HPLC-MS indicated complete conversion. The solvent was removed in vacuo and the residue was purified by flash-chromatography (ethyl acetate/heptane 1:19) to give 25.7 g (128 mmol, 64%) of the desired arylbromide as a white solid.

LC-MS: rt=0.46 min, 201 (M+1, ES+).

6-Dimethylamino-pyridine-3-thiol

At –78° C. a solution of (5-bromo-pyridin-2-yl)-dimethyl-amine (15.0 mmol) in THF (50 mL) was added dropwise to a solution of n-BuLi in Hexane (1.6 mol/L, 10.0 mL). The reaction mixture was stirred for 15 min and sulfur (20.0 mmol) was added. After 1 min a solution of n-BuLi in Hexane (1.6 mol/L, 20.0 ml) was added. The reaction mixture was stirred for 10 min at –78° C. and purified immediately by flash-chromatography (ethyl acetate/heptane 1:3) without previous work-up. A second flash-chromatography (gradient: ethyl acetate/heptane 1:19 to 1:9) yielded 0.50 g (3.24 mmol, 21%) of 6-dimethylamino-pyridine-3-thiol as a yellow oil.

LC-MS: rt=0.46 min, 155 (M+1, ES+).

6-Dimethylamino-pyridine-3-sulfonyl chloride

Hydrochloric acid (25%, 1.13 mL) was added to a solution of 6-dimethylamino-pyridine-3-thiol (0.50 mmol) in DCM (10 mL) at –78° C. A solution of sodium hypochlorite in water (6-14%, 5.2 mL) was added at –78° C. and the reaction mixture was stirred for additional 2 min. The layers were separated and the aqueous layer was extracted with DCM (3×20 mL). The solvents were removed in vacuo and the obtained 6-dimethylamino-pyridine-3-sulfonyl chloride was used immediately in the next synthetic step.

A.2.2 Synthesis of 5-Isopropyl-pyridine-2-sulfonyl chloride

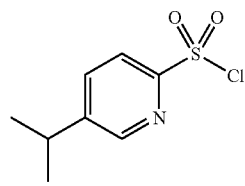

Hydrochloric acid (25%, 63 mL) was added to a suspension of 5-isopropyl-pyridine-2-thiol (90 mmol) in DCM (150 mL) at RT. The reaction mixture was cooled to –15° C., a solution of sodium hypochlorite in water (6-14%, 240 mL) was added dropwise and the reaction mixture was stirred for additional 15 min. After separation of the layers DCM (150 mL) was added to the aqueous layer. Another portion of a solution of sodium hypochlorite in water (6-14%, 90 mL) was added at –15° C. The layers were separated and the aqueous layer was extracted with DCM (2×150 mL). All organic layers were combined and dried with $Na_2SO_4$. The solvents were removed in vacuo and the obtained 5-isopropyl-pyridine-2-sulfonyl chloride was used immediately in the next synthetic step.

A.2.3 Synthesis of 5-Methyl-pyridine-2-sulfonyl chloride

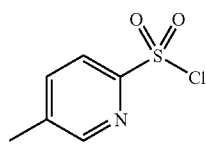

Hydrochloric acid (25%, 21 mL) was added to a suspension of 5-methyl-pyridine-2-thiol (30 mmol) in DCM (50 mL) at RT. The reaction mixture was cooled to –15° C., a solution of sodium hypochlorite in water (6-14%, 80 mL) was added dropwise and the reaction mixture was stirred for additional 15 min. After separation of the layers DCM (150 mL) was added to the aqueous layer. Another portion of a solution of sodium hypochlorite in water (6-14%, 30 mL) was added at –15° C. The layers were separated and the aqueous layer was extracted with DCM (3×100 mL). All organic layers were combined and dried with $Na_2SO_4$. The solvents were removed in vacuo and the obtained 5-methyl-pyridine-2-sulfonyl chloride was used immediately in the next synthetic step.

A.2.4 Synthesis of 3-Methyl-pyridine-2-sulfonyl chloride

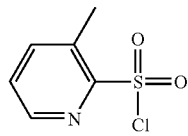

3-Methyl-pyridine-2-thiol

Thiourea (174 mmol) was added to a solution of 2-bromo-3-methylpyridine (87 mmol) in ethanol (500 mL). The reaction mixture was refluxed for 5 h, cooled to RT, treated with an aqueous solution of sodium hydroxide (25%, 1.0 mL) and refluxed for additional 60 min. The mixture was concentrated in vacuo to 50 mL, water (300 mL) and ethyl acetate (300 mL) were added, the layers were separated and the aqueous layer was extracted with ethyl acetate (3×100 mL). Brine (50 mL) was added to the combined organic layers, the layers were separated and the solvents were removed in vacuo. The crude oil was crystallized from ether to give 7.1 g (56.7 mmol, 65%) of the thiol as pale yellow crystals.

LC-MS: rt=0.48 min, 126 (M+1, ES+).

3-Methyl-pyridine-2-sulfonyl chloride

Hydrochloric acid (25%, 9.0 mL) was added to a solution of 3-methyl-pyridine-2-thiol (16 mmol) in DCM (60 mL) at RT. The reaction mixture was cooled to −15° C., a solution of sodium hypochlorite in water (6-14%, 42 mL) was added dropwise and the reaction mixture was stirred for additional 10 min. After separation of the layers the aqueous layer was extracted with DCM (3×50 mL). The organic layers were combined and dried with Na$_2$SO$_4$. The solution of the obtained 3-methyl-pyridine-2-sulfonyl chloride was used immediately in the next synthetic step.

A.3 Synthesis of Other Intermediates

A.3.1 Synthesis of N-Ethyl-N-pyridin-2-ylmethyl-2-p-tolylamino-acetamide

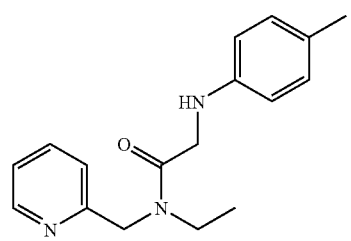

p-Tolylamino-acetic acid tert-butyl ester

A solution of p-toluidine (200 mmol) in THF (500 mL) was treated with tert-butyl bromoacetate (220 mmol) and DIPEA (440 mmol) at RT. The reaction mixture was heated to reflux for 16 h and cooled to RT. Water (200 mL) and EE (500 mL) were added, the layers were separated and the aqueous layer was extracted twice with ethyl acetate (100 mL). The combined organic layers were washed with water and brine. The solvents were removed in vacuo and the residue (44 g) was used without further purification.

LC-MS: rt=0.96 min, 222 (M+1, ES+).

p-Tolylamino-acetic acid

A solution of crude p-tolylamino-acetic acid tert-butyl ester (200 mmol) in DCM (600 mL) was cooled to 0° C. and treated with TFA (150 mL). The reaction mixture was allowed to reach RT and stirred for 4 d. Water (200 mL) was added, the layers were separated and the aqueous layer was extracted with DCM (4×200 mL). The aqueous layer was adjusted to pH 8 by addition of saturated NaHCO$_3$ solution and extracted with ethyl acetate (4×200 mL). The combined organic layers were dried with Na$_2$SO$_4$ and the solvents were removed in vacuo to give the crude acid (18 g) which was used in the next step without further purification.

LC-MS: rt=0.54 min, 166 (M+1, ES+).

N-Ethyl-N-pyridin-2-ylmethyl-2-p-tolylamino-acetamide

A suspension of ethyl-pyridin-2-ylmethyl-amine (29.0 mmol) and DIPEA (78.0 mmol) in DMF (50 mL) was cooled to −20° C. and added to a cold (−20° C.) solution of p-tolylamino-acetic acid (26.0 mmol) and TBTU (34.0 mmol) in DMF (100 mL). The reaction mixture was stirred for 15 min at −20° C. Water (300 mL) and ethyl acetate (400 mL) were added, the layers were separated and the organic layer washed with water (4×100 mL). The combined aqueous layers were extracted with ethyl acetate (200 mL). The combined organic layers were washed with NaOH solution (1.0 mol/L, 100 mL) and brine (100 mL) and dried with Na$_2$SO$_4$. The solvents were removed in vacuo and the obtained solid was dissolved in ethanol. By addition of a solution of hydrogen chloride in ether a byproduct precipitated which was filtered off. Dilution of the remaining solution with ether led to precipitation of the desired acetamide, which was obtained as a white solid (5.3 g).

LC-MS: rt=0.64 min, 284 (M+1, ES+).

A.3.2 Synthesis of 6-Methyl-pyridin-3-ylamine

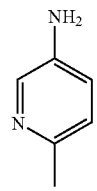

(6-Methyl-pyridin-3-yl)-carbamic acid benzyl ester

To a suspension of 6-methylnicotinic acid (36.4 mmol) in toluene (100 mL) was added DIPEA (120 mmol) and Diphenylphosphoryl azide (91.1 mmol). The reaction mixture was heated to reflux for 1 h, cooled to RT and treated with benzyl alcohol (120 mmol). After 30 min ethyl acetate (200 mL) and water (200 mL) were added, the layers were separated and the organic layer washed with water (3×100 mL). The solvents were removed in vacuo and the residue was purified by preparative HPLC chromatography to give (6-methyl-pyridin-3-yl)-carbamic acid benzyl ester (5.2 g, 21.5 mmol, 59%) as a colourless oil.

LC-MS: rt=0.68 min, 243 (M+1, ES+).

6-Methyl-pyridin-3-ylamine

To a solution of (6-methyl-pyridin-3-yl)-carbamic acid benzyl ester (21.5 mmol) in methanol (100 mL) was added ammonium formate (107 mmol) and palladium on activated carbon (10%, wet, 1.0 g). The reaction mixture was stirred under nitrogen for 1 h and filtered over Celite. The solvents were removed in vacuo and the residue was dissolved in ethyl acetate. The organic layer washed with water (2×100 mL) and the combined aqueous layers were extracted with ethyl acetate (3×100 mL). The organic layers were combined and dried with $Na_2SO_4$. The solvents were removed in vacuo and the crude 6-methyl-pyridin-3-ylamine (0.80 g, 7.40 mmol, 34%) was used without further purification.

LC-MS: rt=0.16 min, 109 (M+1, ES+).

B Synthesis of Sulfonylamino-acetic Acid Derivatives via α-aminoacetamide Intermediates (One-pot Procedure)

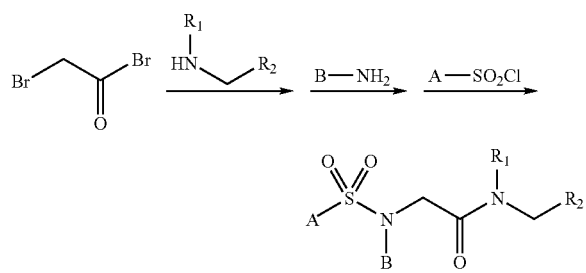

General Procedure

A solution of 2-bromoacetyl bromide (0.30 mmol) in THF (0.50 mL) was cooled to 0° C. and treated dropwise with the respective dialkylamine (0.30 mmol). After addition of ethyldiisopropylamine (1.80 mmol) the reaction mixture was allowed to reach RT and was stirred for 60 min. A solution of the primary amine B—$NH_2$ (0.30 mmol) in THF (0.50 mL) was added. The suspension was stirred at 60° C. for 16 h, cooled to RT and treated with a solution of the respective sulfonyl chloride (0.30 mmol) in THF (0.50 mL). After 60 min the solvent was removed in vacuo and the residue was purified by preparative HPLC chromatography to give the following sulfonamides:

EXAMPLE 1

N,N-Diethyl-2-[(quinoline-8-sulfonyl)-p-tolyl-amino]-acetamide

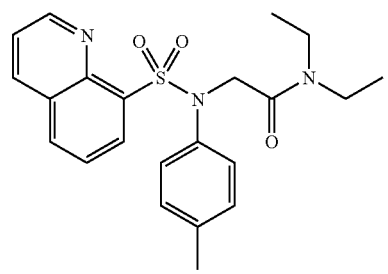

prepared by reaction of 2-bromoacetyl bromide with diethylamine, p-toluidine and 8-quinolinesulfonyl chloride
LC-MS: rt=0.92 min, 412 (M+1, ES+).

EXAMPLE 2

2-[(4-tert-Butyl-benzenesulfonyl)-p-tolyl-amino]-N,N-diethyl-acetamide

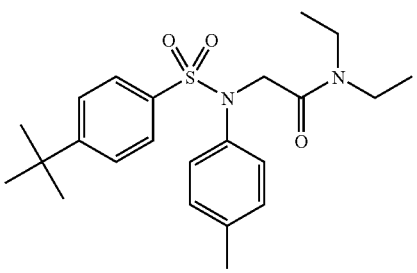

prepared by reaction of 2-bromoacetyl bromide with diethylamine, p-toluidine and 4-tert-butyl-benzenesulfonyl chloride
LC-MS: rt=1.10 min, 417 (M+1, ES+).

EXAMPLE 3

2-[(4-Bromo-benzenesulfonyl)-p-tolyl-amino]-N,N-diethyl-acetamide

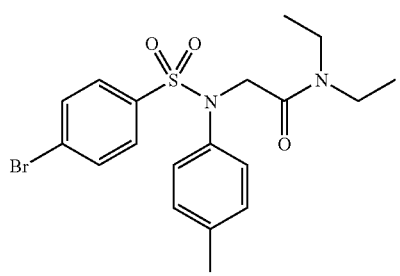

prepared by reaction of 2-bromoacetyl bromide with diethylamine, p-toluidine and 4-bromo-benzenesulfonyl chloride
LC-MS: rt=1.04 min, 439 (M+1, ES+).

EXAMPLE 4

N,N-Diethyl-2-[(naphthalene-2-sulfonyl)-p-tolyl-amino]-acetamide

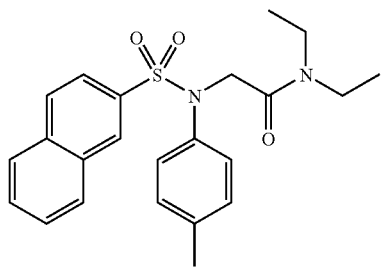

prepared by reaction of 2-bromoacetyl bromide with diethylamine, p-toluidine and 2-naphthalenesulfonyl chloride
LC-MS: rt=1.04 min, 411 (M+1, ES+).

EXAMPLE 5

2-[(3-Chloro-benzenesulfonyl)-p-tolyl-amino]-N,N-diethyl-acetamide

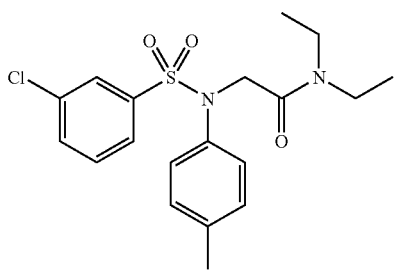

prepared by reaction of 2-bromoacetyl bromide with diethylamine, p-toluidine and 3-chloro-benzenesulfonyl chloride
LC-MS: rt=1.02 min, 395 (M+1, ES+).

EXAMPLE 6

N,N-Diethyl-2-[(3-fluoro-benzenesulfonyl)-p-tolyl-amino]-acetamide

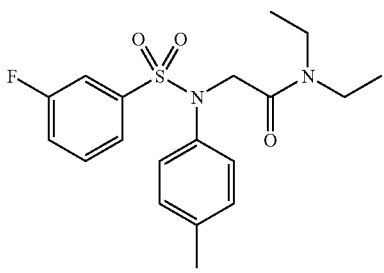

prepared by reaction of 2-bromoacetyl bromide with diethylamine, p-toluidine and 3-fluoro-benzenesulfonyl chloride
LC-MS: rt=0.97 min, 379 (M+1, ES+).

EXAMPLE 7

2-[(2-Chloro-benzenesulfonyl)-p-tolyl-amino]-N,N-diethyl-acetamide

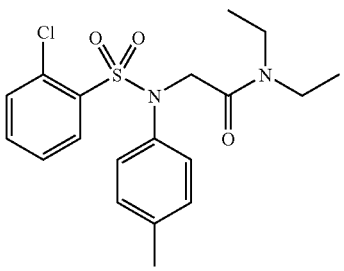

prepared by reaction of 2-bromoacetyl bromide with diethylamine, p-toluidine and 2-chloro-benzenesulfonyl chloride
LC-MS: rt=0.98 min, 395 (M+1, ES+).

EXAMPLE 8

N,N-Diethyl-2-[(toluene-3-sulfonyl)-p-tolyl-amino]-acetamide

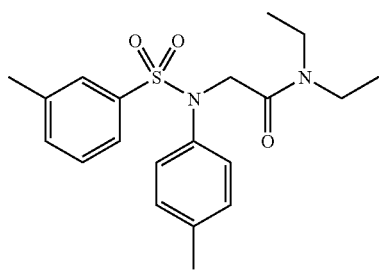

prepared by reaction of 2-bromoacetyl bromide with diethylamine, p-toluidine and toluene-3-sulfonyl chloride
LC-MS: rt=0.99 min, 375 (M+1, ES+).

EXAMPLE 9

N,N-Diethyl-2-[(4-ethyl-benzenesulfonyl)-p-tolyl-amino]-acetamide

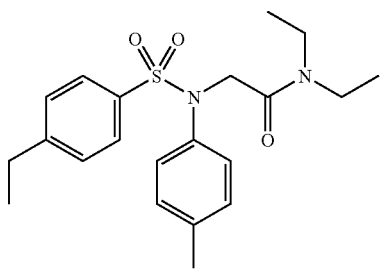

prepared by reaction of 2-bromoacetyl bromide with diethylamine, p-toluidine and 4-ethyl-benzenesulfonyl chloride
LC-MS: rt=1.03 min, 389 (M+1, ES+).

EXAMPLE 10

N,N-Diethyl-2-[(toluene-2-sulfonyl)-p-tolyl-amino]-acetamide

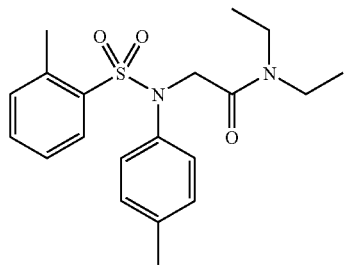

prepared by reaction of 2-bromoacetyl bromide with diethylamine, p-toluidine and toluene-2-sulfonyl chloride
LC-MS: rt=0.98 min, 375 (M+1, ES+).

EXAMPLE 11

N,N-Diethyl-2-[p-tolyl-(2-trifluoromethyl-benzenesulfonyl)-amino]-acetamide

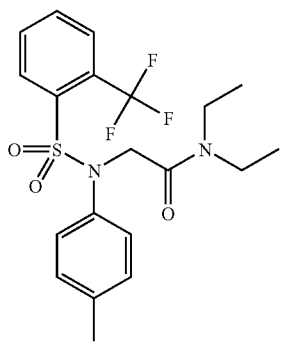

prepared by reaction of 2-bromoacetyl bromide with diethylamine, p-toluidine and 2-trifluoromethyl-benzenesulfonyl chloride
LC-MS: rt=1.00 min, 429 (M+1, ES+).

EXAMPLE 12

2-[(3,4-Difluoro-benzenesulfonyl)-p-tolyl-amino]-N,N-diethyl-acetamide

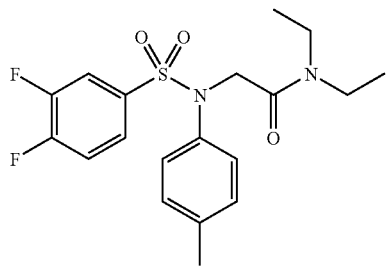

prepared by reaction of 2-bromoacetyl bromide with diethylamine, p-toluidine and 3,4-difluoro-benzenesulfonyl chloride
LC-MS: rt=1.00 min, 397 (M+1, ES+).

EXAMPLE 13

2-[(4-tert-Butyl-benzenesulfonyl)-phenyl-amino]-N,N-diethyl-acetamide

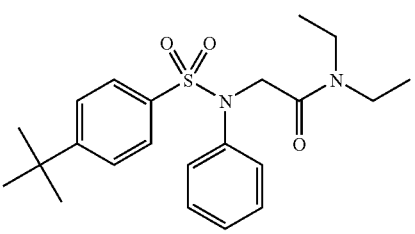

prepared by reaction of 2-bromoacetyl bromide with diethylamine, aniline and 4-tert-butyl-benzenesulfonyl chloride
LC-MS: rt=1.07 min, 403 (M+1, ES+).

EXAMPLE 14

N,N-Diethyl-2-[(naphthalene-2-sulfonyl)-phenyl-amino]-acetamide

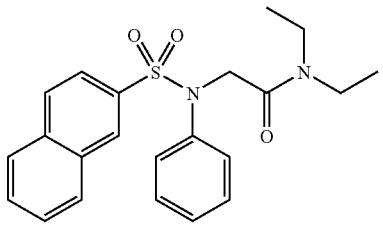

prepared by reaction of 2-bromoacetyl bromide with diethylamine, aniline and naphthalene-2-sulfonyl chloride
LC-MS: rt=1.00 min, 397 (M+1, ES+).

EXAMPLE 15

N,N-Diethyl-2-[phenyl-(toluene-3-sulfonyl)-amino]-acetamide

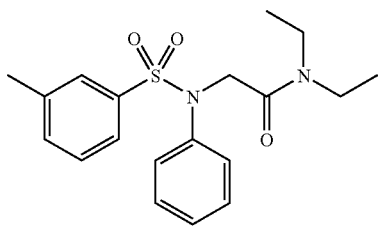

prepared by reaction of 2-bromoacetyl bromide with diethylamine, aniline and toluene-3-sulfonyl chloride
LC-MS: rt=0.94 min, 361 (M+1, ES+).

EXAMPLE 16

N,N-Diethyl-2-[(4-ethyl-benzenesulfonyl)-phenyl-amino]-acetamide

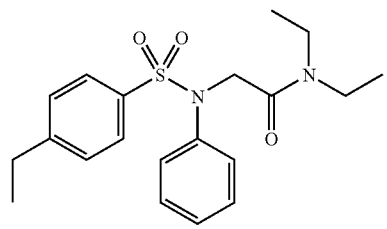

prepared by reaction of 2-bromoacetyl bromide with diethylamine, aniline and 4-ethyl-benzenesulfonyl chloride LC-MS: rt=0.99 min, 375 (M+1, ES+).

EXAMPLE 17

2-[(4-tert-Butyl-benzenesulfonyl)-p-tolyl-amino]-N-ethyl-N-methyl-acetamide

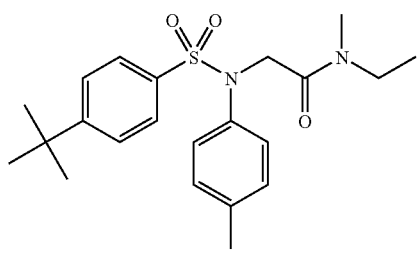

prepared by reaction of 2-bromoacetyl bromide with ethylmethylamine, p-toluidine and 4-tert-butyl-benzenesulfonyl chloride LC-MS: rt=1.06 min, 403 (M+1, ES+).

EXAMPLE 18

2-[(4-tert-Butyl-benzenesulfonyl)-phenyl-amino]-N-ethyl-N-methyl-acetamide

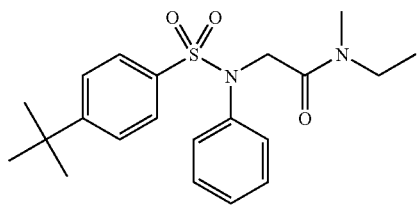

prepared by reaction of 2-bromoacetyl bromide with ethylmethylamine, aniline and 4-tert-butyl-benzenesulfonyl chloride LC-MS: rt=1.02 min, 389 (M+1, ES+).

EXAMPLE 19

2-[(4-tert-Butyl-benzenesulfonyl)-(4-methoxy-phenyl)-amino]-N,N-diethyl-acetamide

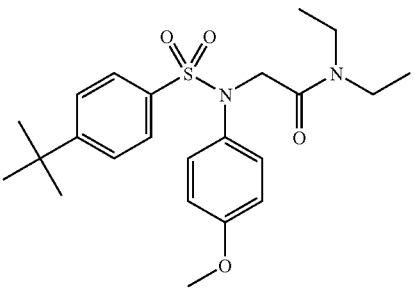

prepared by reaction of 2-bromoacetyl bromide with diethylamine, p-anisidine and 4-tert-butyl-benzenesulfonyl chloride LC-MS: rt=1.07 min, 433 (M+1, ES+).

EXAMPLE 20

2-[(4-tert-Butyl-benzenesulfonyl)-cyclohexyl-amino]-N,N-diethyl-acetamide

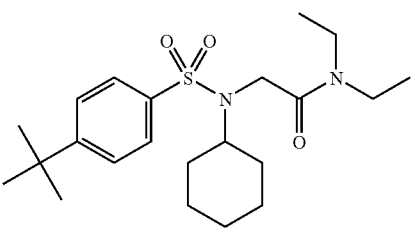

prepared by reaction of 2-bromoacetyl bromide with diethylamine, cyclohexyl-amine and 4-tert-butyl-benzenesulfonyl chloride LC-MS: rt=1.16 min, 409 (M+1, ES+).

EXAMPLE 21

2-[(4-tert-Butyl-benzenesulfonyl)-(4-methyl-cyclohexyl)-amino]-N,N-diethyl-acetamide

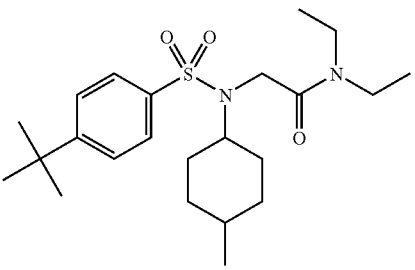

prepared by reaction of 2-bromoacetyl bromide with diethylamine, 4-methyl-cyclohexylamine and 4-tert-butyl-benzenesulfonyl chloride LC-MS: rt=1.20 min, 423 (M+1, ES+).

EXAMPLE 22

2-[(4-tert-Butyl-benzenesulfonyl)-(6-chloro-pyridin-3-yl)-amino]-N,N-diethyl-acetamide

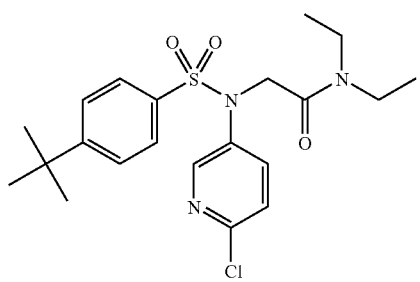

prepared by reaction of 2-bromoacetyl bromide with diethylamine, 5-amino-2-chloropyridine and 4-tert-butyl-benzenesulfonyl chloride LC-MS: rt=1.08 min, 438 (M+1, ES+).

EXAMPLE 23

2-[(4-tert-Butyl-benzenesulfonyl)-(3-methoxy-phenyl)-amino]-N,N-diethyl-acetamide

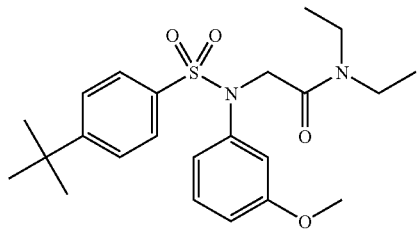

prepared by reaction of 2-bromoacetyl bromide with diethylamine, m-anisidine and 4-tert-butyl-benzenesulfonyl chloride LC-MS: rt=1.08 min, 433 (M+1, ES+).

EXAMPLE 24

2-[(4-tert-Butyl-benzenesulfonyl)-(4-ethyl-phenyl)-amino]-N,N-diethyl-acetamide

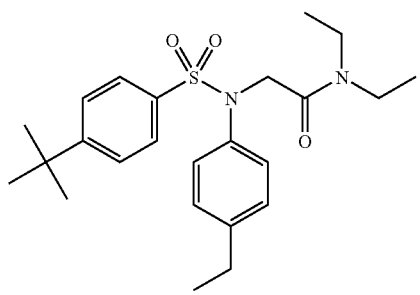

prepared by reaction of 2-bromoacetyl bromide with diethylamine, 4-ethylaniline and 4-tert-butyl-benzenesulfonyl chloride LC-MS: rt=1.15 min, 431 (M+1, ES+).

EXAMPLE 25

2-[(4-tert-Butyl-benzenesulfonyl)-m-tolyl-amino]-N,N-diethyl-acetamide

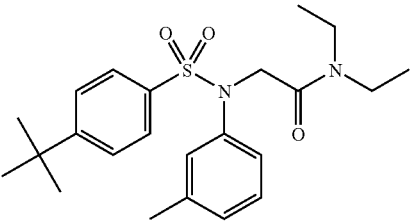

prepared by reaction of 2-bromoacetyl bromide with diethylamine, m-toluidine and 4-tert-butyl-benzenesulfonyl chloride LC-MS: rt=1.12 min, 417 (M+1, ES+).

EXAMPLE 26

2-[(4-tert-Butyl-benzenesulfonyl)-o-tolyl-amino]-N,N-diethyl-acetamide

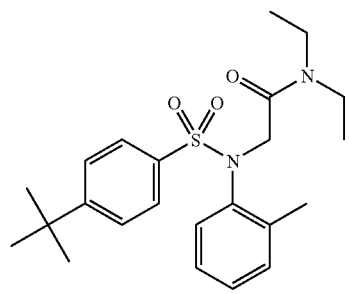

prepared by reaction of 2-bromoacetyl bromide with diethylamine, o-toluidine and 4-tert-butyl-benzenesulfonyl chloride LC-MS: rt=1.12 min, 417 (M+1, ES+).

EXAMPLE 27

2-[(4-tert-Butyl-benzenesulfonyl)-(4-trifluoromethyl-phenyl)-amino]-N,N-diethyl-acetamide

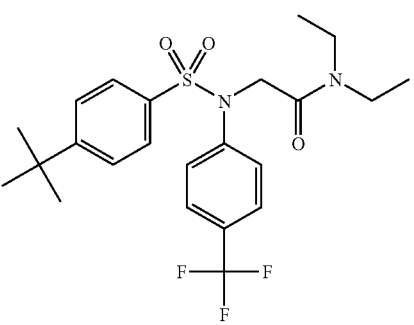

prepared by reaction of 2-bromoacetyl bromide with diethylamine, 4-trifluoro-methyl-aniline and 4-tert-butyl-benzenesulfonyl chloride LC-MS: rt=1.14 min, 471 (M+1, ES+).

EXAMPLE 28

2-[(4-tert-Butyl-benzenesulfonyl)-(2-methoxy-phenyl)-amino]-N-cyclopropyl-methyl-N-n-propyl-acetamide

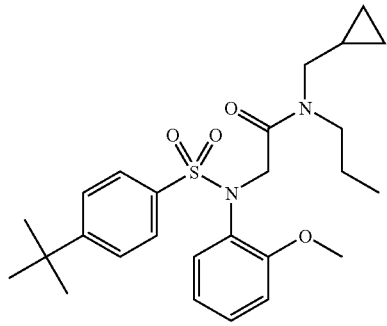

prepared by reaction of 2-bromoacetyl bromide with N-cyclopropylmethyl-N-propylamine, o-anisidine and 4-tert-butyl-benzenesulfonyl chloride
LC-MS: rt=1.17 min, 473 (M+1, ES+).

EXAMPLE 29

2-[(4-tert-Butyl-benzenesulfonyl)-(4-methoxy-phenyl)-amino]-N-cyclopropyl-methyl-N-n-propyl-acetamide

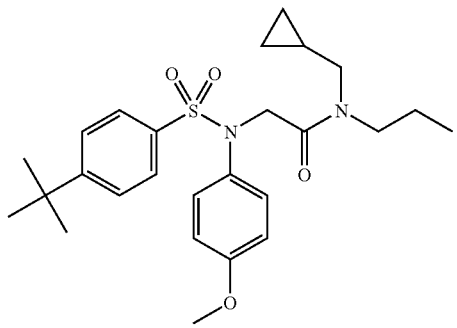

prepared by reaction of 2-bromoacetyl bromide with N-cyclopropylmethyl-N-propylamine, p-anisidine and 4-tert-butyl-benzenesulfonyl chloride
LC-MS: rt=1.16 min, 473 (M+1, ES+).

EXAMPLE 30

2-[(4-tert-Butyl-benzenesulfonyl)-cyclohexyl-amino]-N-cyclopropylmethyl-N-n-propyl-acetamide

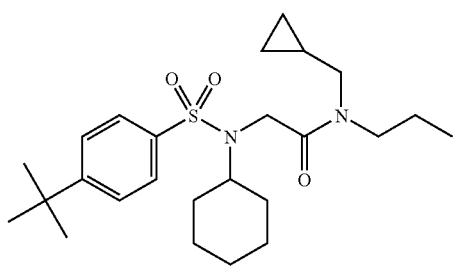

prepared by reaction of 2-bromoacetyl bromide with N-cyclopropylmethyl-N-propylamine, cyclohexylamine and 4-tert-butyl-benzenesulfonyl chloride
LC-MS: rt=1.24 min, 449 (M+1, ES+).

EXAMPLE 31

2-[(4-tert-Butyl-benzenesulfonyl)-(6-chloro-pyridin-3-yl)-amino]-N-cyclo-propylmethyl-N-n-propyl-acetamide

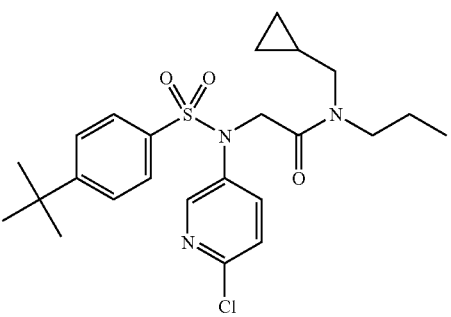

prepared by reaction of 2-bromoacetyl bromide with N-cyclopropylmethyl-N-propylamine, 5-amino-2-chloropyridine and 4-tert-butyl-benzenesulfonyl chloride
LC-MS: rt=1.16 min, 478 (M+1, ES+).

EXAMPLE 32

2-[(4-tert-Butyl-benzenesulfonyl)-(3-methoxy-phenyl)-amino]-N-cyclopropyl-methyl-N-n-propyl-acetamide

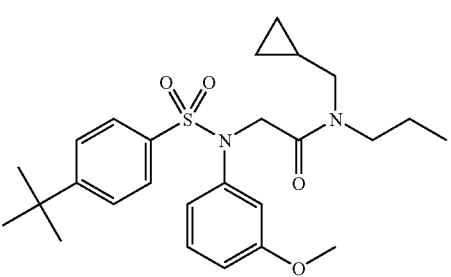

prepared by reaction of 2-bromoacetyl bromide with N-cyclopropylmethyl-N-propylamine, m-anisidine and 4-tert-butyl-benzenesulfonyl chloride
LC-MS: rt=1.17 min, 473 (M+1, ES+).

EXAMPLE 33

2-[(4-tert-Butyl-benzenesulfonyl)-(2-chloro-phenyl)-amino]-N-cyclopropyl-methyl-N-n-propyl-acetamide

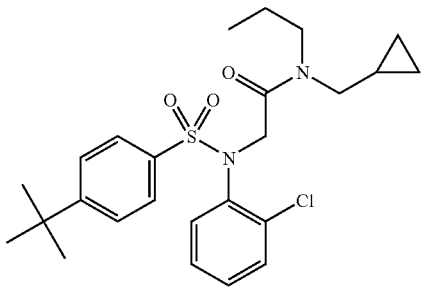

prepared by reaction of 2-bromoacetyl bromide with N-cyclopropylmethyl-N-propylamine, 2-chloroaniline and 4-tert-butyl-benzenesulfonyl chloride
LC-MS: rt=1.21 min, 477 (M+1, ES+).

EXAMPLE 34

2-[(4-tert-Butyl-benzenesulfonyl)-m-tolyl-amino]-N-cyclopropylmethyl-N-n-propyl-acetamide

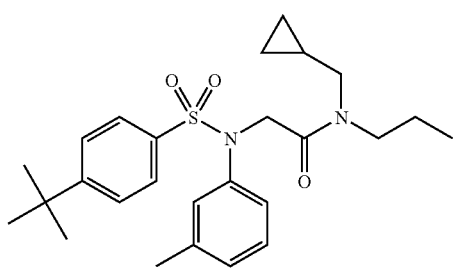

prepared by reaction of 2-bromoacetyl bromide with N-cyclopropylmethyl-N-propylamine, m-toluidine and 4-tert-butyl-benzenesulfonyl chloride
LC-MS: rt=1.20 min, 457 (M+1, ES+).

EXAMPLE 35

2-[(6-Dimethylamino-pyridine-3-sulfonyl)-p-tolyl-amino]-N,N-diethyl-acetamide

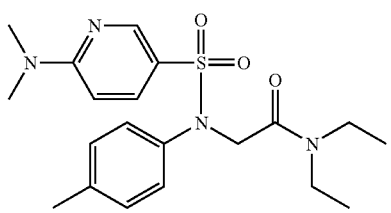

prepared by reaction of 2-bromoacetyl bromide with N,N-diethylamine, p-toluidine 6-dimethylamino-pyridine-3-sulfonyl chloride; in contrast to the general procedure the intermediate N,N-diethyl-2-p-tolylamino-acetamide was isolated LC-MS: rt=0.87 min, 405 (M+1, ES+).

EXAMPLE 36

2-[(6-Dimethylamino-pyridine-3-sulfonyl)-p-tolyl-amino]-N-ethyl-N-pyridin-2-ylmethyl-acetamide

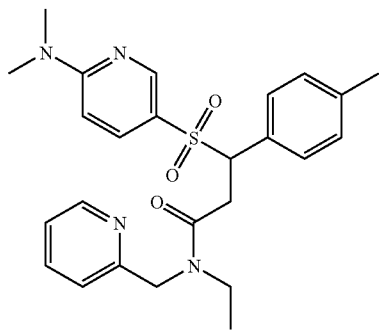

prepared by reaction of 6-dimethylamino-pyridine-3-sulfonyl chloride with N-ethyl-N-pyridin-2-ylmethyl-2-p-tolylamino-acetamide
LC-MS: rt=0.75 min, 468 (M+1, ES+).

C Synthesis of Sulfonylamino-acetic Acid Derivatives via Isolated Sulfanilide-intermediates (Two Step Procedure)

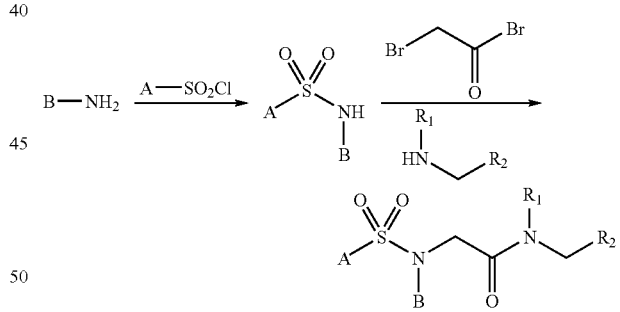

C.1 Synthesis of Sulfanilide-intermediates (General Procedure)

The respective sulfonyl chloride (100 mmol) was added portionwise to a solution of the respective aromatic amine (100 mmol) and ethyldiisopropylamine (120 mmol) in THF (100 mL) at RT. The suspension was stirred for 16 h, the solvent was removed in vacuo and the residue was redissolved in ethyl acetate. After washing the organic phase with water and brine the solvent was removed in vacuo. The residue was purified either by crystallization from diethylether or methanol/water or by preparative HPLC chromatography to give the following sulfonamides:

4-tert-Butyl-N-p-tolyl-benzenesulfonamide

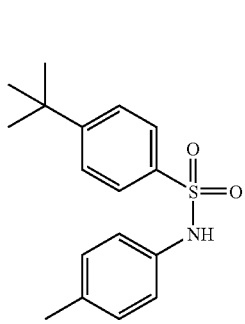

prepared by reaction of p-toluidine with 4-tert-butyl-benzenesulfonyl chloride
LC-MS: rt=1.18 min, 304 (M+1, ES+).

2-Methyl-N-p-tolyl-benzenesulfonamide

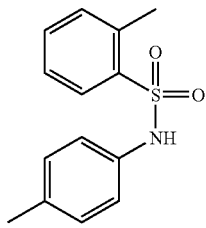

prepared by reaction of p-toluidine with 2-methyl-benzenesulfonyl chloride
LC-MS: rt=1.06 min, 523 (2M+1, ES+).

N-(6-Methoxy-pyridin-3-yl)-2-methyl-benzenesulfonamide

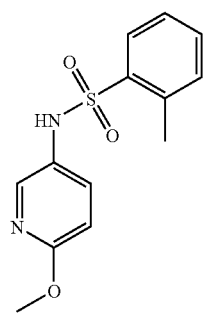

prepared by reaction of 6-methoxy-pyridin-3-ylamine with 2-methyl-benzenesulfonyl chloride
LC-MS: rt=0.85 min, 279 (M+1, ES+).

N-(2-Methoxy-phenyl)-2-methyl-benzenesulfonamide

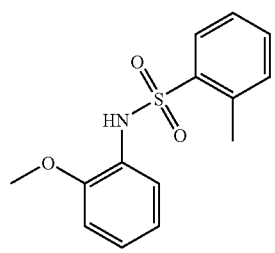

prepared by reaction of o-anisidine with 2-methyl-benzenesulfonyl chloride
LC-MS: rt=0.93 min, 278 (M+1, ES+).

4-tert-Butyl-N-(6-methoxy-pyridin-3-yl)-benzenesulfonamide

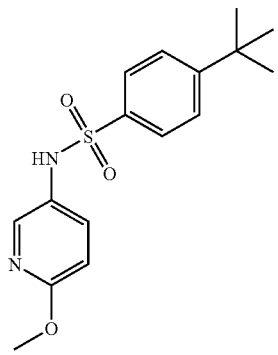

prepared by reaction of 6-methoxy-pyridin-3-ylamine with 4-tert-butyl-benzenesulfonyl chloride
LC-MS: rt=0.96 min, 321 (M+1, ES+).

4-tert-Butyl-N-(2-methoxy-phenyl)-benzenesulfonamide

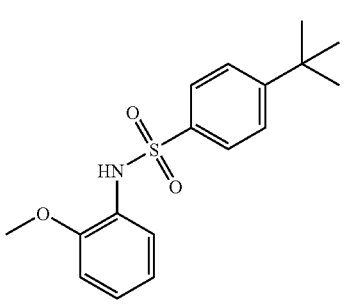

prepared by reaction of o-anisidine with 4-tert-butyl-benzenesulfonyl chloride
LC-MS: rt=1.02 min, 320 (M+1, ES+).

Naphthalene-2-sulfonic acid (6-methoxy-pyridin-3-yl)-amide

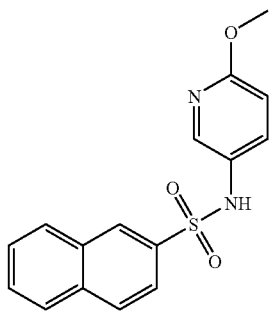

prepared by reaction of 6-methoxy-pyridin-3-ylamine with naphthalene-2-sulfonyl chloride
LC-MS: rt=0.91 min, 315 (M+1, ES+).

Naphthalene-2-sulfonic acid (2-methoxy-phenyl)-amide

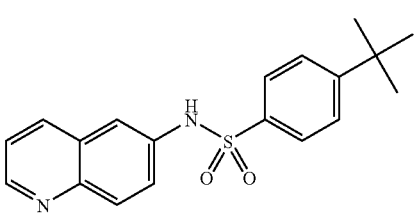

prepared by reaction of o-anisidine with naphthalene-2-sulfonyl chloride
LC-MS: rt=0.97 min, 314 (M+1, ES+).

4-tert-Butyl-N-quinolin-6-yl-benzenesulfonamide prepared by reaction of quinolin-6-ylamine with 4-tert-butyl-benzenesulfonyl chloride
LC-MS: rt=0.82 min, 341 (M+1, ES+).

4-tert-Butyl-N-(3-dimethylamino-phenyl)-benzene-sulfonamide

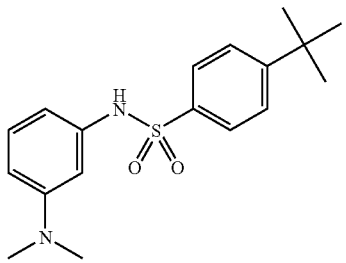

prepared by reaction of N,N-dimethyl-benzene-1,3-diamine with 4-tert-butyl-benzenesulfonyl chloride
LC-MS: rt=0.89 min, 333 (M+1, ES+).

4-tert-Butyl-N-isoquinolin-5-yl-benzenesulfonamide

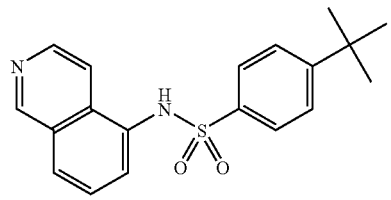

prepared by reaction of isoquinolin-5-ylamine with 4-tert-butyl-benzenesulfonyl chloride
LC-MS: rt=0.80 min, 341 (M+1, ES+).

2-(4-tert-Butyl-benzenesulfonylamino)-benzamide

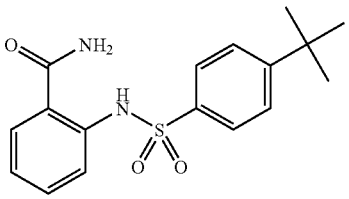

prepared by reaction of 2-amino-benzamide with 4-tert-butyl-benzenesulfonyl chloride
LC-MS: rt=0.96 min, 333 (M+1, ES+).

47

4-tert-Butyl-N-(1H-indazol-6-yl)-benzenesulfonamide

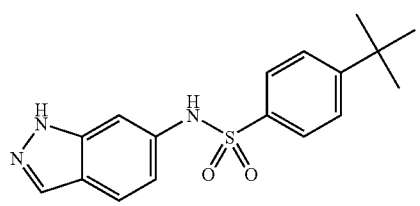

prepared by reaction of 1H-indazol-6-ylamine with 4-tert-butyl-benzenesulfonyl chloride LC-MS: rt=0.93 min, 330 (M+1, ES+).

5-Isopropyl-pyridine-2-sulfonic acid m-tolylamide

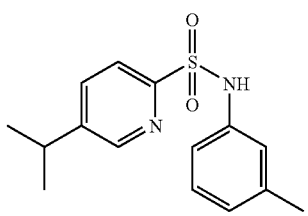

prepared by reaction of m-tolylamine with 5-isopropyl-pyridine-2-sulfonyl chloride LC-MS: rt=0.96 min, 291 (M+1, ES+).

5-Isopropyl-pyridine-2-sulfonic acid (2-methoxy-phenyl)-amide

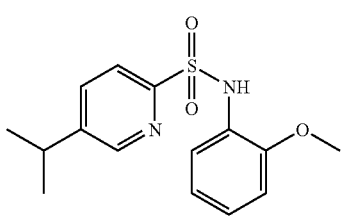

prepared by reaction of 2-methoxy-phenylamine with 5-isopropyl-pyridine-2-sulfonyl chloride LC-MS: rt=0.94 min, 307 (M+1, ES+).

48

5-Isopropyl-pyridine-2-sulfonic acid (6-methoxy-pyridin-3-yl)-amide

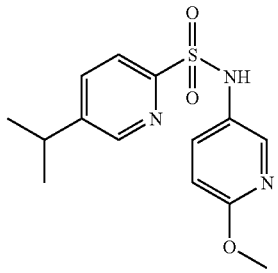

prepared by reaction of 6-methoxy-pyridin-3-ylamine with 5-isopropyl-pyridine-2-sulfonyl chloride LC-MS: rt=0.89 min, 308 (M+1, ES+).

5-Isopropyl-pyridine-2-sulfonic acid p-tolylamide

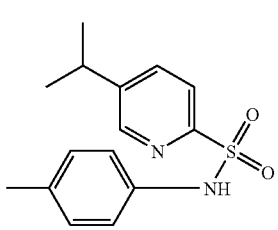

prepared by reaction of p-tolylamine with 5-isopropyl-pyridine-2-sulfonyl chloride LC-MS: rt=0.97 min, 291 (M+1, ES+).

5-Methyl-pyridine-2-sulfonic acid p-tolylamide

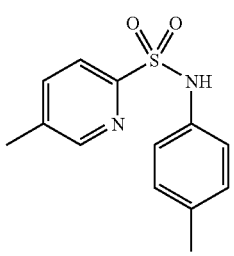

prepared by reaction of p-tolylamine with 5-methyl-pyridine-2-sulfonyl chloride

LC-MS: rt=0.88 min, 263 (M+1, ES+).

4-tert-Butyl-N-(6-methyl-pyridin-3-yl)-benzene-sulfonamide

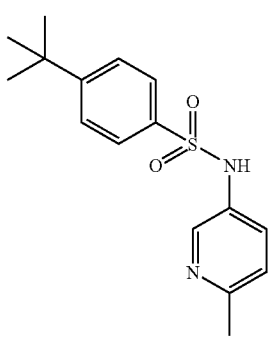

prepared by reaction of 6-methyl-pyridin-3-ylamine with 4-tert-butyl-benzene-sulfonyl chloride
LC-MS: rt=0.78 min, 305 (M+1, ES+).

N-[5-(4-tert-Butyl-benzenesulfonylamino)-pyridin-2-yl]-acetamide

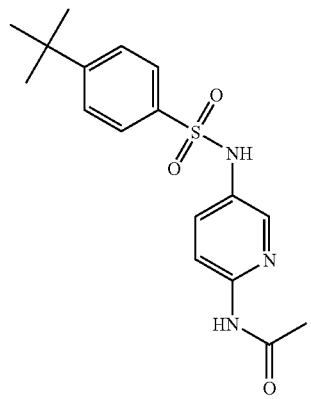

prepared by reaction of N-(5-amino-pyridin-2-yl)-acetamide with 4-tert-butyl-benzene-sulfonyl chloride
LC-MS: rt=0.90 min, 348 (M+1, ES+).

3-Methyl-pyridine-2-sulfonic acid p-tolylamide

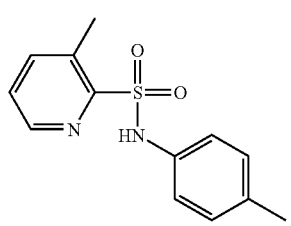

prepared by reaction of p-tolylamine with 3-methyl-pyridine-2-sulfonyl chloride
LC-MS: rt=0.89 min, 263 (M+1, ES+).

3-Methyl-pyridine-2-sulfonic acid m-tolylamide

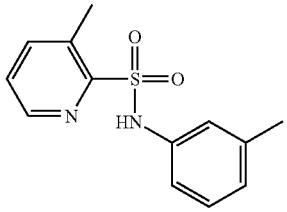

prepared by reaction of m-tolylamine with 3-methyl-pyridine-2-sulfonyl chloride
LC-MS: rt=0.89 min, 263 (M+1, ES+).

3-Methyl-pyridine-2-sulfonic acid (2-methoxy-phenyl)-amide

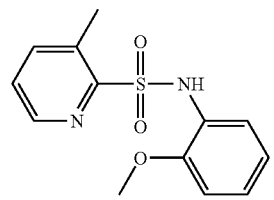

prepared by reaction of 2-methoxy-phenylamine with 3-methyl-pyridine-2-sulfonyl chloride
LC-MS: rt=0.85 min, 279 (M+1, ES+).

3-Methyl-pyridine-2-sulfonic acid (6-methoxy-pyridin-3-yl)-amide

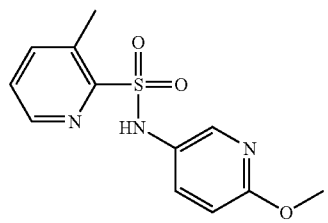

prepared by reaction of 6-methoxy-pyridin-3-ylamine with 3-methyl-pyridine-2-sulfonyl chloride
LC-MS: rt=0.79 min, 280 (M+1, ES+).

2-(2,2,2-Trifluoro-acetyl)-1,2,3,4-tetrahydro-iso-
quinoline-7-sulfonic acid p-tolylamide

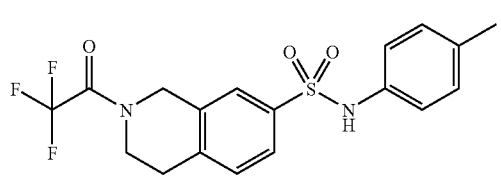

prepared by reaction of p-tolylamine with 2-(2,2,2-trifluoro-acetyl)-1,2,3,4-tetrahydro-isoquinoline-7-sulfonyl chloride
LC-MS: rt=0.98 min, 399 (M+1, ES+).

C.2 Synthesis of Sulfonylamino-acetic Acid
Derivatives (General Procedure)

To a solution of 2-bromoacetyl bromide (0.20 mmol) in THF (1.0 mL) was added a solution of the respective amine (0.20 mmol) in THF (0.50 mL) at RT. A solution of potassium tert-butoxide (0.20 mmol) in THF (0.50 mL) was added and the reaction mixture was stirred for 2 h. To this suspension a solution of the respective potassium N-tolylsulfonamide was added, which was obtained by adding potassium tert-butoxide (0.20 mmol) to a solution of the respective sulfonamide (0.20 mmol) in THF (2.5 mL) and diluting with DMSO (0.50 mL). The obtained suspension was stirred at 60° C. for 1 h, the solvent was removed in vacuo and the residue was purified by preparative HPLC chromatography to give the following sulfonamides:

EXAMPLE 37

2-[(4-tert-Butyl-benzenesulfonyl)-p-tolyl-amino]-N,
N-di-n-propyl-acetamide

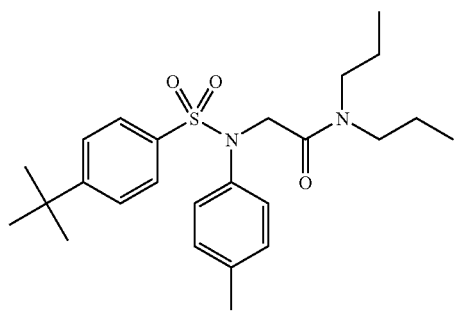

prepared by reaction of 2-bromoacetyl bromide with di-n-propylamine and 4-tert-butyl-N-p-tolyl-benzenesulfonamide
LC-MS: rt=1.20 min, 445 (M+1, ES+).

EXAMPLE 38

N-Benzyl-2-[(4-tert-butyl-benzenesulfonyl)-p-tolyl-
amino]-N-ethyl-acetamide

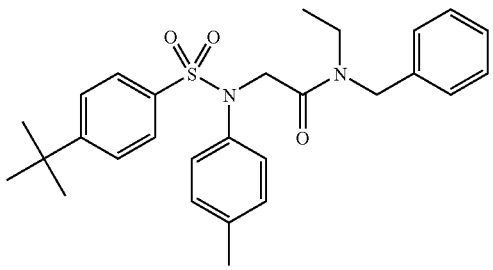

prepared by reaction of 2-bromoacetyl bromide with N-benzyl-N-ethylamine and 4-tert-butyl-N-p-tolyl-benzenesulfonamide
LC-MS: rt=1.19 min, 479 (M+1, ES+).

EXAMPLE 39

2-[(4-tert-Butyl-benzenesulfonyl)-p-tolyl-amino]-N-
ethyl-N-pyridin-4-ylmethyl-acetamide

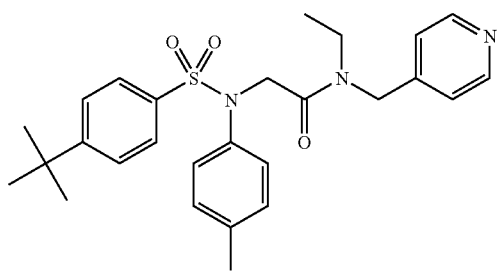

prepared by reaction of 2-bromoacetyl bromide with N-ethyl-N-pyridin-4-ylmethylamine and 4-tert-butyl-N-p-tolyl-benzenesulfonamide
LC-MS: rt=0.83 min, 480 (M+1, ES+).

EXAMPLE 40

N,N-Di-n-propyl-2-[(toluene-2-sulfonyl)-p-tolyl-
amino]-acetamide

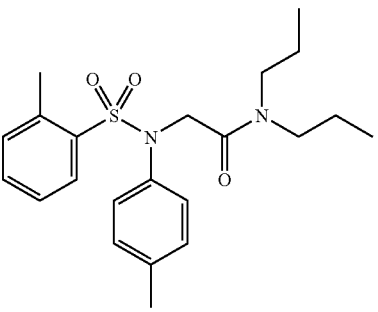

prepared by reaction of 2-bromoacetyl bromide with di-n-propylamine and 2-methyl-N-p-tolyl-benzenesulfonamide
LC-MS: rt=1.20 min, 403 (M+1, ES+).

EXAMPLE 41

N-Benzyl-N-ethyl-2-[(toluene-2-sulfonyl)-p-tolyl-amino]-acetamide

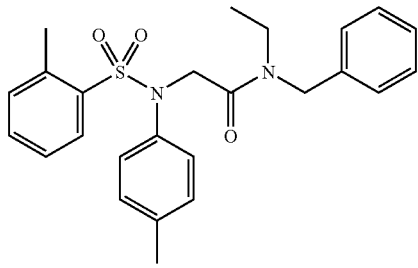

prepared by reaction of 2-bromoacetyl bromide with N-benzyl-N-ethylamine and 2-methyl-N-p-tolyl-benzenesulfonamide LC-MS: rt=1.20 min, 437 (M+1, ES+).

EXAMPLE 42

N,N-Diethyl-2-[(6-methoxy-pyridin-3-yl)-(toluene-2-sulfonyl)-amino]-acetamide

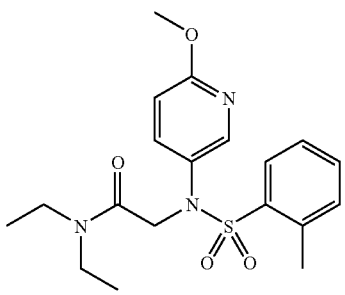

prepared by reaction of 2-bromoacetyl bromide with diethylamine and N-(6-methoxy-pyridin-3-yl)-2-methyl-benzenesulfonamide LC-MS: rt=0.93 min, 392 (M+1, ES+).

EXAMPLE 43

N,N-Diethyl-2-[(2-methoxy-phenyl)-(toluene-2-sulfonyl)-amino]-acetamide

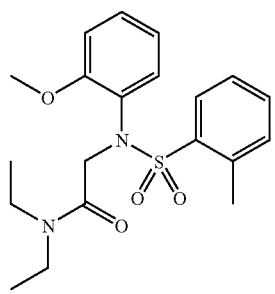

prepared by reaction of 2-bromoacetyl bromide with diethylamine and N-(2-methoxy-phenyl)-2-methyl-benzenesulfonamide LC-MS: rt=0.96 min, 391 (M+1, ES+).

EXAMPLE 44

2-[(4-tert-Butyl-benzenesulfonyl)-(6-methoxy-pyridin-3-yl)-amino]-N,N-diethyl-acetamide

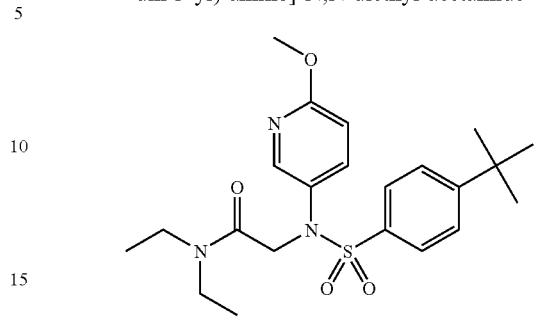

prepared by reaction of 2-bromoacetyl bromide with diethylamine and 4-tert-butyl-N-(6-methoxy-pyridin-3-yl)-benzenesulfonamide LC-MS: rt=1.02 min, 434 (M+1, ES+).

EXAMPLE 45

2-[(4-tert-Butyl-benzenesulfonyl)-(2-methoxy-phenyl)-amino]-N,N-diethyl-acetamide

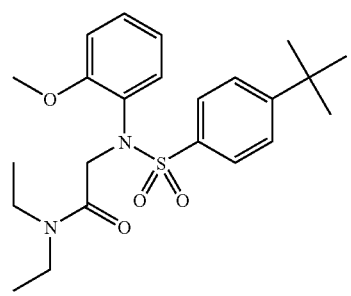

prepared by reaction of 2-bromoacetyl bromide with diethylamine and 4-tert-butyl-N-(2-methoxy-phenyl)-benzenesulfonamide LC-MS: rt=1.04 min, 433 (M+1, ES+).

EXAMPLE 46

N-Benzyl-N-ethyl-2-[(6-methoxy-pyridin-3-yl)-(toluene-2-sulfonyl)-amino]-acetamide

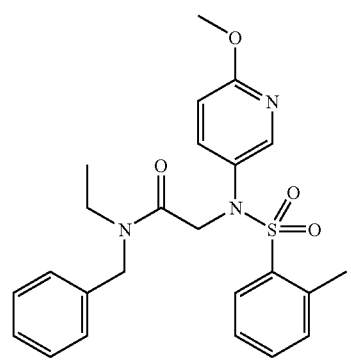

prepared by reaction of 2-bromoacetyl bromide with N-benzyl-N-ethylamine and N-(6-methoxy-pyridin-3-yl)-2-methyl-benzenesulfonamide LC-MS: rt=1.01 min, 454 (M+1, ES+).

EXAMPLE 47

N-Benzyl-N-ethyl-2-[(2-methoxy-phenyl)-(toluene-2-sulfonyl)-amino]-acetamide

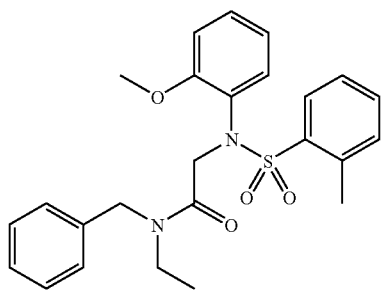

prepared by reaction of 2-bromoacetyl bromide with N-benzyl-N-ethylamine and N-(2-methoxy-phenyl)-2-methyl-benzenesulfonamide LC-MS: rt=1.04 min, 453 (M+1, ES+).

EXAMPLE 48

N-Benzyl-2-[(4-tert-butyl-benzenesulfonyl)-(6-methoxy-pyridin-3-yl)-amino]-N-ethyl-acetamide

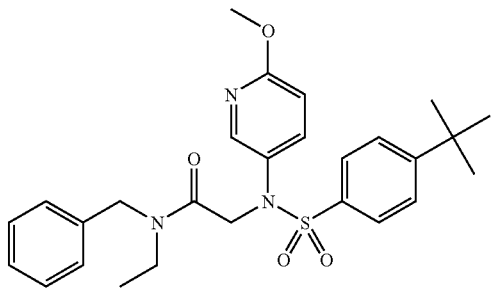

prepared by reaction of 2-bromoacetyl bromide with N-benzyl-N-ethylamine and 4-tert-butyl-N-(6-methoxy-pyridin-3-yl)-benzenesulfonamide LC-MS: rt=1.08 min, 496 (M+1, ES+).

EXAMPLE 49

N-Benzyl-2-[(4-tert-butyl-benzenesulfonyl)-(2-methoxy-phenyl)-amino]-N-ethyl-acetamide

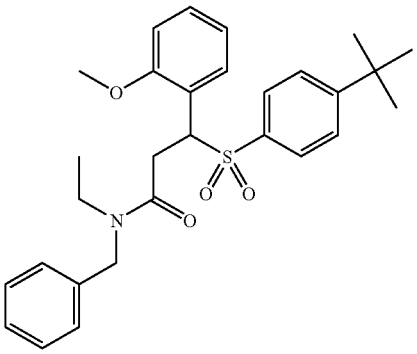

prepared by reaction of 2-bromoacetyl bromide with N-benzyl-N-ethylamine and 4-tert-butyl-N-(2-methoxy-phenyl)-benzenesulfonamide LC-MS: rt=1.10 min, 495 (M+1, ES+).

EXAMPLE 50

N-Benzyl-N-ethyl-2-[(6-methoxy-pyridin-3-yl)-(naphthalene-2-sulfonyl)-amino]-acetamide

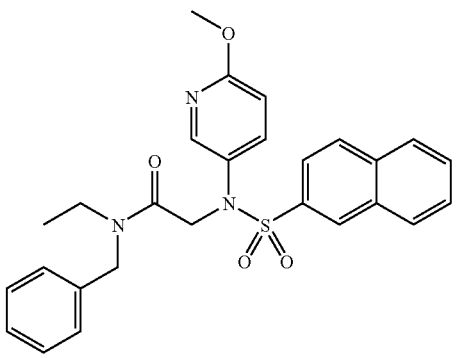

prepared by reaction of 2-bromoacetyl bromide with N-benzyl-N-ethylamine and naphthalene-2-sulfonic acid (6-methoxy-pyridin-3-yl)-amide LC-MS: rt=1.05 min, 490 (M+1, ES+).

EXAMPLE 51

N-Benzyl-N-ethyl-2-[(2-methoxy-phenyl)-(naphthalene-2-sulfonyl)-amino]-acetamide

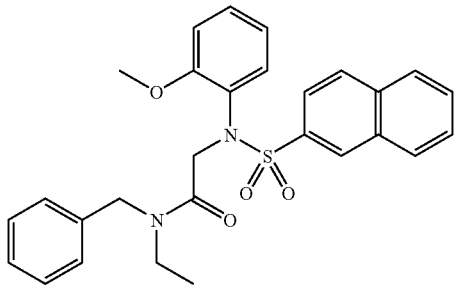

prepared by reaction of 2-bromoacetyl bromide with N-benzyl-N-ethylamine and naphthalene-2-sulfonic acid (2-methoxy-phenyl)-amide LC-MS: rt=1.06 min, 489 (M+1, ES+).

EXAMPLE 52

2-[(4-tert-Butyl-benzenesulfonyl)-p-tolyl-amino]-N-ethyl-N-(2-hydroxy-ethyl)-acetamide

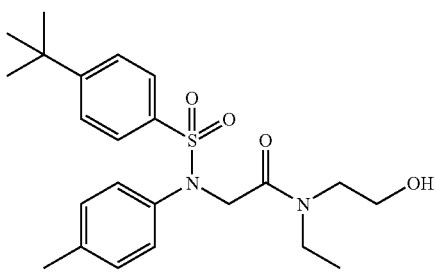

prepared by reaction of 2-bromoacetyl bromide with N-ethyl-N-(2-hydroxy-ethyl)-amine and 4-tert-butyl-N-p-tolyl-benzenesulfonamide; in contrast to the general procedure the intermediate 2-bromo-N-ethyl-N-(2-hydroxy-ethyl)-acetamide was isolated before being used in the coupling with the potassium N-tolylsulfonamide.

LC-MS: rt=0.97 min, 433 (M+1, ES+).

D Synthesis of Sulfonylamino-acetic Acid Derivatives via Isolated 2-bromo-N,N-diethylacetamide (Two Step Procedure)

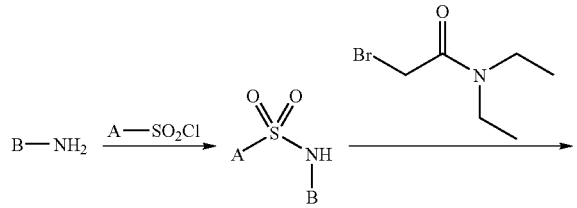

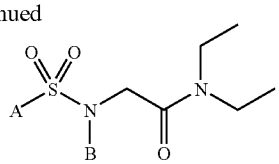

D.1 Synthesis of 2-bromo-N,N-diethylacetamide

A solution of 2-bromoacetyl bromide (20.2 g, 100 mmol) in THF (300 mL) was cooled to 0° C. and treated with diethylamine (7.31 g, 100 mmol). After dropwise addition of ethyldiisopropylamine (15.5 g, 120 mmol) the reaction mixture was allowed to reach RT and was stirred for 90 min. Water (250 mL) and ethyl acetate (300 mL) were added, the layers were separated and the aqueous layer was extracted twice with ethyl acetate (100 mL). The solvents were removed in vacuo and the residue was purified by distillation (bp 120-121° C./24 mbar) to give 5.24 g (27%) of the title compound as pale yellow oil.

D.2 Synthesis of Sulfonylamino-acetic Acid Derivatives (General Procedure)

A solution of the respective sulfonyl chloride (0.20 mmol) in DCM (1.0 mL) was added to a solution of p-toluidine (0.20 mmol) and ethyldiisopropylamine (0.24 mmol) in DCM (1.0 mL) at RT. After stirring for 16 h water was added, the layers were separated and the aqueous layer was extracted twice with DCM (2.0 mL). The combined organic extracts were concentrated in vacuo and dissolved in dry THF (1.0 mL). A solution of potassium tert-butoxide (0.20 mmol) in THF (0.50 mL) was added. The reaction mixture was treated with a solution of 2-bromo-N,N-diethylacetamide (0.20 mmol) in THF (0.50 mL) and stirred for 16 h at RT. The solvent was removed in vacuo and the residue was purified by preparative HPLC chromatography to give the following sulfonamides:

EXAMPLE 53

N,N-Diethyl-2-[(4-isopropyl-benzenesulfonyl)-p-tolyl-amino]-acetamide

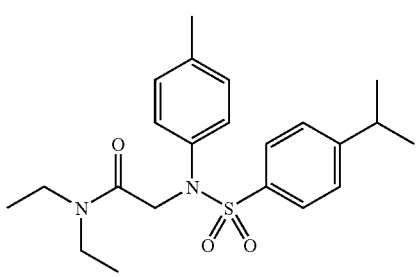

prepared by reaction of 2-bromo-N,N-diethylacetamide with p-toluidine and 4-isopropyl-benzenesulfonyl chloride LC-MS: rt=1.04 min, 403 (M+1, ES+).

EXAMPLE 54

N,N-Diethyl-2-[(2-methoxy-4-methyl-benzenesulfonyl)-p-tolyl-amino]-acetamide

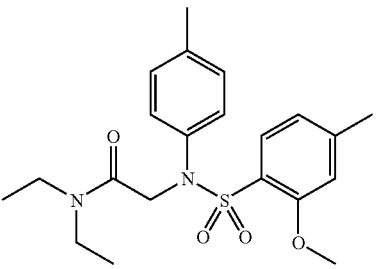

prepared by reaction of 2-bromo-N,N-diethylacetamide with p-toluidine and 2-methoxy-4-methyl-benzenesulfonyl chloride
LC-MS: rt=0.96 min, 405 (M+1, ES+).

EXAMPLE 55

2-[(3-Chloro-4-methyl-benzenesulfonyl)-p-tolyl-amino]-N,N-diethyl-acetamide

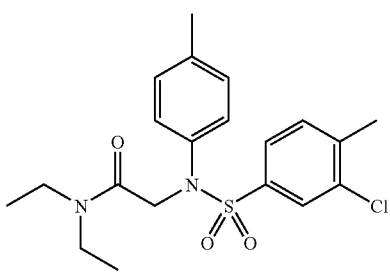

prepared by reaction of 2-bromo-N,N-diethylacetamide with p-toluidine and 3-chloro-4-methyl-benzenesulfonyl chloride
LC-MS: rt=1.03 min, 409 (M+1, ES+).

EXAMPLE 56

N,N-Diethyl-2-[p-tolyl-(3-trifluoromethyl-benzenesulfonyl)-amino]-acetamide

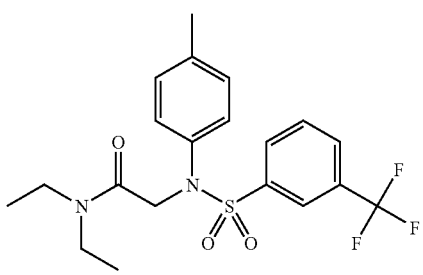

prepared by reaction of 2-bromo-N,N-diethylacetamide with p-toluidine and 3-trifluoromethyl-benzenesulfonyl chloride
LC-MS: rt=1.03 min, 429 (M+1, ES+).

EXAMPLE 57

2-[(6-Bromo-5-chloro-pyridine-3-sulfonyl)-p-tolyl-amino]-N,N-diethyl-acetamide

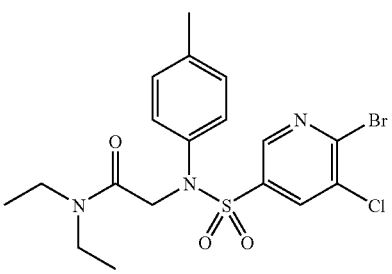

prepared by reaction of 2-bromo-N,N-diethylacetamide with p-toluidine and 6-bromo-5-chloro-pyridine-3-sulfonyl chloride
LC-MS: rt=1.04 min, 474 (M+1, ES+).

EXAMPLE 58

N,N-Diethyl-2-[((E)-2-phenyl-ethenesulfonyl)-p-tolyl-amino]-acetamide

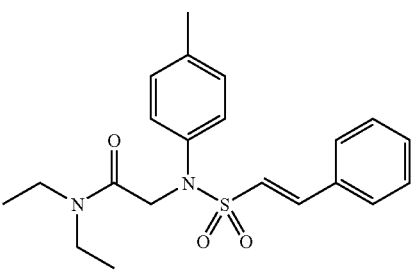

prepared by reaction of 2-bromo-N,N-diethylacetamide with p-toluidine and (E)-2-phenyl-ethenesulfonyl chloride
LC-MS: rt=1.01 min, 387 (M+1, ES+).

EXAMPLE 59

N,N-Diethyl-2-[(5-isopropyl-pyridine-2-sulfonyl)-p-tolyl-amino]-acetamide

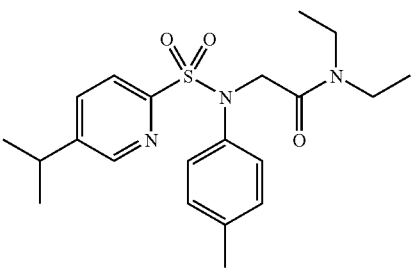

prepared by reaction of 2-bromo-N,N-diethylacetamide with p-toluidine and 5-isopropyl-pyridine-2-sulfonyl chloride; in contrast to the general procedure the intermediate 5-isopropyl-pyridine-2-sulfonic acid p-tolylamide was isolated and crystallized from methanol/water 10/1

LC-MS: rt=1.00 min, 404 (M+1, ES+).

E Synthesis of Sulfonylamino-acetic Acid Derivatives via an Amide Coupling

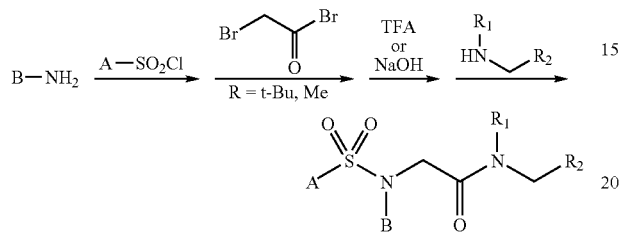

E.1 Synthesis of Sulfonylamino-acetic Acids via tert-butyl Acetates (General Procedure)

A solution of the respective sulfonamide A-S(O)$_2$NH—B (1.6 mmol) in DMSO (5.0 mL) was added to solid potassium tert-butoxide (1.6 mmol) which was dissolved by ultrasound. Tert-butyl bromoacetate (1.69 mmol, 0.25 mL) was added and the reaction mixture was stirred at RT for 12 h. Water (20 mL) and ethyl acetate (15 mL) were added, the layers were separated and the aqueous layer was extracted with ethyl acetate (15 mL). The solvents were removed in vacuo and the residue was either purified by preparative HPLC chromatography or used without further purification. A solution of the obtained tert-butyl acetate in DCM (5.0 mL) was treated with TFA (1.6 mL) and stirred for 12 h at 35° C. Water (10 mL) and ethyl acetate (20 mL) were added, the layers were separated and the aqueous layer was extracted twice with ethyl acetate (2×20 mL). The solvents were removed in vacuo and the residue was purified by preparative HPLC chromatography to give the following acetic acid derivatives:

[(4-tert-Butyl-benzenesulfonyl)-p-tolyl-amino]-acetic acid

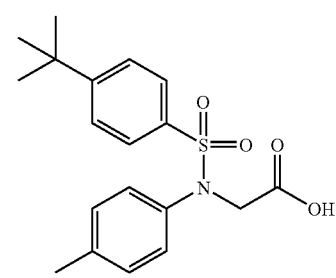

prepared by reaction of 4-tert-butyl-N-p-tolyl-benzenesulfonamide with tert-butyl bromoacetate LC-MS: rt=0.99 min, 362 (M+1, ES+).

[(4-tert-Butyl-benzenesulfonyl)-quinolin-6-yl-amino]-acetic acid

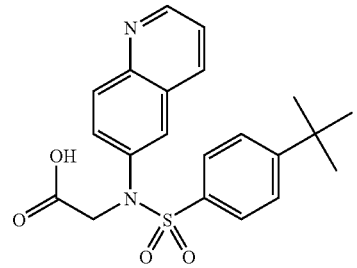

prepared by reaction of 4-tert-butyl-N-quinolin-6-yl-benzenesulfonamide with tert-butyl bromoacetate LC-MS: rt=0.84 min, 399 (M+1, ES+).

[(4-tert-Butyl-benzenesulfonyl)-(3-dimethylamino-phenyl)-amino]-acetic acid

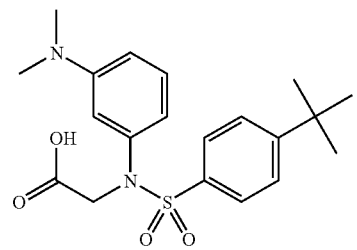

prepared by reaction of 4-tert-butyl-N-(3-dimethylamino-phenyl)-benzene-sulfonamide with tert-butyl bromoacetate LC-MS: rt=0.90 min, 391 (M+1, ES+).

[(4-tert-Butyl-benzenesulfonyl)-isoquinolin-5-yl-amino]-acetic acid

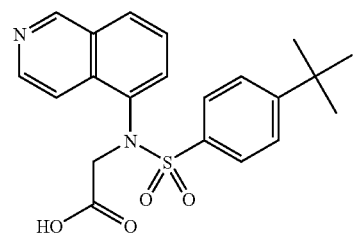

prepared by reaction of 4-tert-butyl-N-isoquinolin-5-yl-benzenesulfonamide with tert-butyl bromoacetate LC-MS: rt=0.80 min, 399 (M+1, ES+).

[(4-tert-Butyl-benzenesulfonyl)-(2-carbamoyl-phenyl)-amino]-acetic acid

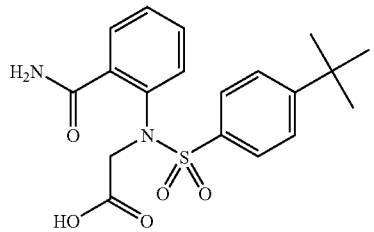

prepared by reaction of 2-(4-tert-butyl-benzenesulfonylamino)-benzamide with tert-butyl bromoacetate
LC-MS: rt=0.88 min, 391 (M+1, ES+).

[(4-tert-Butyl-benzenesulfonyl)-(1H-indazol-6-yl)-amino]-acetic acid

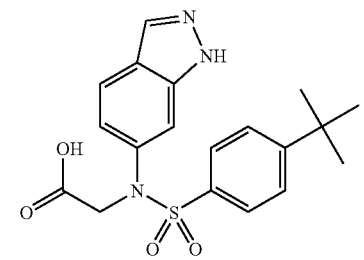

prepared by reaction of 4-tert-butyl-N-(1H-indazol-6-yl)-benzenesulfonamide with tert-butyl bromoacetate
LC-MS: rt=0.91 min, 388 (M+1, ES+).

[(5-Isopropyl-pyridine-2-sulfonyl)-m-tolyl-amino]-acetic acid

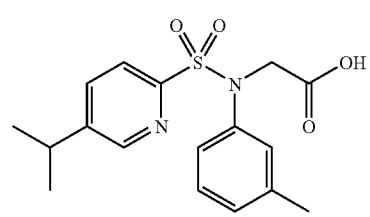

prepared by reaction of 5-isopropyl-pyridine-2-sulfonic acid m-tolylamide with tert-butyl bromoacetate
LC-MS: rt=0.94 min, 349 (M+1, ES+).

[(5-Isopropyl-pyridine-2-sulfonyl)-(2-methoxy-phenyl)-amino]-acetic acid

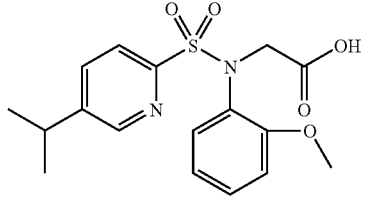

prepared by reaction of 5-isopropyl-pyridine-2-sulfonic acid (2-methoxy-phenyl)-amide with tert-butyl bromoacetate
LC-MS: rt=0.89 min, 365 (M+1, ES+).

[(5-Isopropyl-pyridine-2-sulfonyl)-(6-methoxy-pyridin-3-yl)-amino]-acetic acid

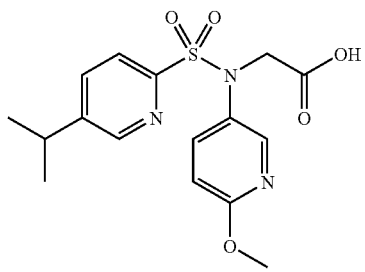

prepared by reaction of 5-isopropyl-pyridine-2-sulfonic acid (6-methoxy-pyridin-3-yl)-amide with tert-butyl bromoacetate
LC-MS: rt=0.87 min, 366 (M+1, ES+).

[(5-Isopropyl-pyridine-2-sulfonyl)-p-tolyl-amino]-acetic acid

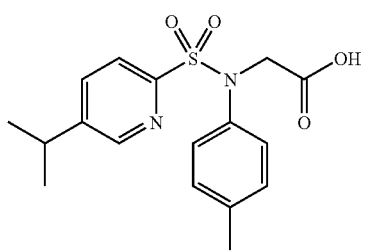

prepared by reaction of 5-isopropyl-pyridine-2-sulfonic acid p-tolylamide with tert-butyl bromoacetate
LC-MS: rt=0.93 min, 349 (M+1, ES+).

[(2-Methoxy-phenyl)-(toluene-2-sulfonyl)-amino]-acetic acid

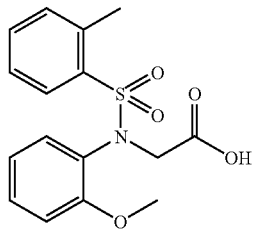

prepared by reaction of N-(2-methoxy-phenyl)-2-methyl-benzenesulfonamide with tert-butyl bromoacetate
LC-MS: rt=0.89 min, 336 (M+1, ES+).

[(6-Methoxy-pyridin-3-yl)-(toluene-2-sulfonyl)-amino]-acetic acid

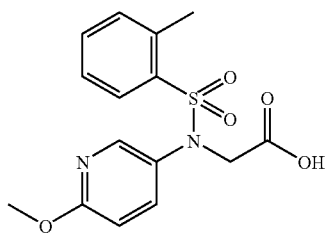

prepared by reaction of N-(6-methoxy-pyridin-3-yl)-2-methyl-benzenesulfonamide with tert-butyl bromoacetate
LC-MS: rt=0.85 min, 337 (M+1, ES+).

[(Toluene-2-sulfonyl)-p-tolyl-amino]-acetic acid

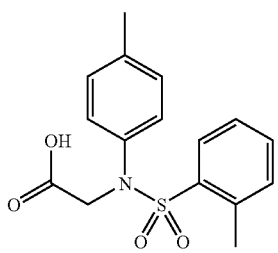

prepared by reaction of 2-methyl-N-p-tolyl-benzenesulfonamide with tert-butyl bromoacetate
LC-MS: rt=0.91 min, 320 (M+1, ES+).

[(5-Methyl-pyridine-2-sulfonyl)-p-tolyl-amino]-acetic acid

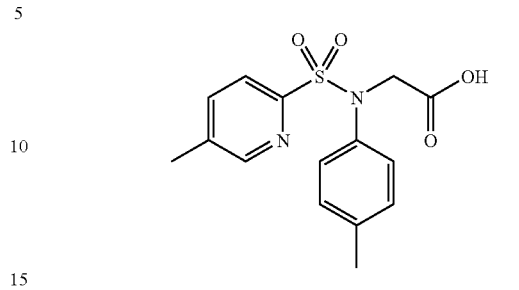

prepared by reaction of 5-methyl-pyridine-2-sulfonic acid p-tolylamide with tert-butyl bromoacetate
LC-MS: rt=0.85 min, 321 (M+1, ES+).

{p-Tolyl-[2-(2,2,2-trifluoro-acetyl)-1,2,3,4-tetrahydro-isoquinoline-7-sulfonyl]-amino}-acetic acid

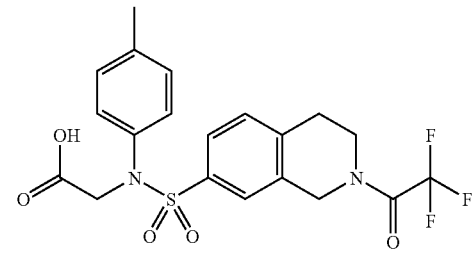

prepared by reaction of 2-(2,2,2-trifluoro-acetyl)-1,2,3,4-tetrahydro-isoquinoline-7-sulfonic acid p-tolylamide with tert-butyl bromoacetate
LC-MS: rt=0.95 min, 457 (M+1, ES+).

E.2 Synthesis of Sulfonylamino-acetic Acids via Methyl Acetates (General Procedure)

A solution of the respective sulfonamide A-S(O)$_2$NH—B (10.0 mmol) in DMSO (10.0 mL) was treated with solid potassium tert-butoxide (10.0 mmol). Methyl bromo-acetate (11.0 mmol, 1.0 mL) was added at RT and the reaction mixture was heated to 60° C. for 4 h. Water (40 mL) and ethyl acetate (40 mL) were added, the layers were separated and the aqueous layer was extracted twice with ethyl acetate (2×30 mL). The combined organic layers were washed with water (4×50 mL) and brine (50 mL) and the solvents were removed in vacuo.

A solution of NaOH (100 mmol) in water (50 mL) was added to a solution of the crude methyl acetate in methanol (500 mL) and stirred either at 60° C. for 1 h or at RT for 16 h. Hydrochloric acid (2.0 mol/L) was added to pH 7 and methanol was removed in vacuo. The aqueous layer was extracted with ethyl acetate (4×100 mL) and the combined organic layers were washed with brine (50 mL). The solvents were removed in vacuo and the residue was purified by preparative HPLC chromatography to give the following acetic acid derivatives:

[(4-tert-Butyl-benzenesulfonyl)-(6-methyl-pyridin-3-yl)-amino]-acetic acid

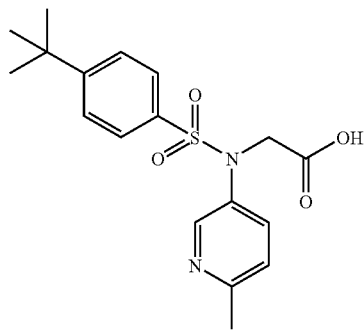

prepared by reaction of 4-tert-butyl-N-(6-methyl-pyridin-3-yl)-benzenesulfonamide with methyl bromoacetate
LC-MS: rt=0.80 min, 363 (M+1, ES+).

[(6-Amino-pyridin-3-yl)-(4-tert-butyl-benzenesulfonyl)-amino]-acetic acid

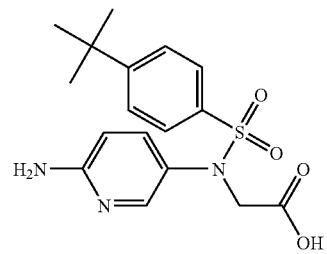

prepared by reaction of N-[5-(4-tert-butyl-benzenesulfonylamino)-pyridin-2-yl]-acetamide with methyl bromoacetate
LC-MS: rt=0.74 min, 364 (M+1, ES+).

[(3-Methyl-pyridine-2-sulfonyl)-p-tolyl-amino]-acetic acid

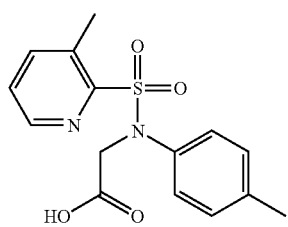

prepared by reaction of 3-methyl-pyridine-2-sulfonic acid p-tolylamide with methyl bromoacetate
LC-MS: rt=0.85 min, 321 (M+1, ES+).

[(3-Methyl-pyridine-2-sulfonyl)-m-tolyl-amino]-acetic acid

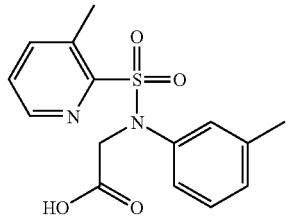

prepared by reaction of 3-methyl-pyridine-2-sulfonic acid m-tolylamide with methyl bromoacetate
LC-MS: rt=0.85 min, 321 (M+1, ES+).

[(2-Methoxy-phenyl)-(3-methyl-pyridine-2-sulfonyl)-amino]-acetic acid

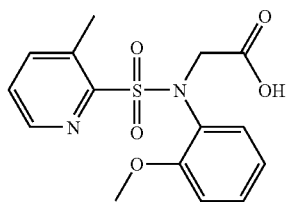

prepared by reaction of 3-methyl-pyridine-2-sulfonic acid (2-methoxy-phenyl)-amide with methyl bromoacetate
LC-MS: rt=0.80 min, 337 (M+1, ES+).

[(6-Methoxy-pyridin-3-yl)-(3-methyl-pyridine-2-sulfonyl)-amino]-acetic acid

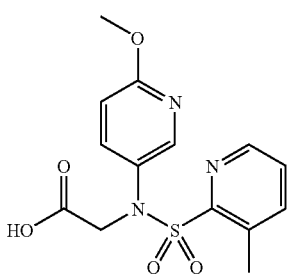

prepared by reaction of 3-methyl-pyridine-2-sulfonic acid (6-methoxy-pyridin-3-yl)-amide with methyl bromoacetate
LC-MS: rt=0.80 min, 338 (M+1, ES+).

E.3 Synthesis of Sulfonylamino-acetic Acids (TBTU Coupling, General Procedure)

A solution of the respective acetic acid derivative (0.10 mmol) in DMF (1.0 mL) was treated with the respective amine (0.10 mmol). DIPEA (0.30 mmol) and TBTU (0.13 mmol) were added. The reaction mixture was stirred at RT for 16 h and purified by preparative HPLC chromatography to give the following sulfonamides:

EXAMPLE 60

N-Benzyl-2-[(4-tert-butyl-benzenesulfonyl)-p-tolyl-amino]-N-(2-hydroxy-ethyl)-acetamide

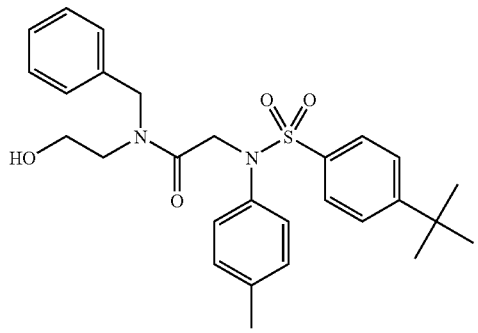

prepared by reaction of [(4-tert-butyl-benzenesulfonyl)-p-tolyl-amino]-acetic acid with 2-benzylamino-ethanol
LC-MS: rt=1.04 min, 495 (M+1, ES+).

EXAMPLE 61

2-[(4-tert-Butyl-benzenesulfonyl)-p-tolyl-amino]-N-(2-hydroxy-ethyl)-N-isopropyl-acetamide

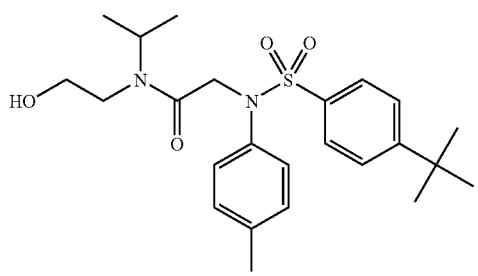

prepared by reaction of [(4-tert-butyl-benzenesulfonyl)-p-tolyl-amino]-acetic acid with 2-isopropylamino-ethanol
LC-MS: rt=1.00 min, 447 (M+1, ES+).

EXAMPLE 62

2-[(4-tert-Butyl-benzenesulfonyl)-p-tolyl-amino]-N,N-bis-(2-hydroxy-ethyl)-acetamide

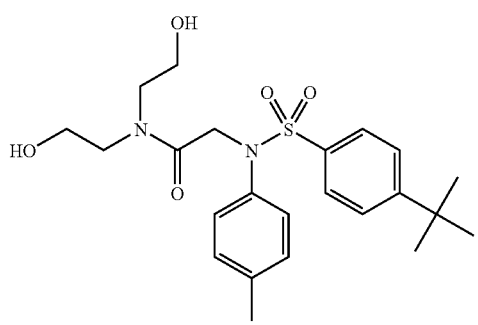

prepared by reaction of [(4-tert-butyl-benzenesulfonyl)-p-tolyl-amino]-acetic acid with 2-(2-hydroxy-ethylamino)-ethanol
LC-MS: rt=0.90 min, 449 (M+1, ES+).

EXAMPLE 63

2-[(4-tert-Butyl-benzenesulfonyl)-p-tolyl-amino]-N-(2-cyano-ethyl)-N-ethyl-acetamide

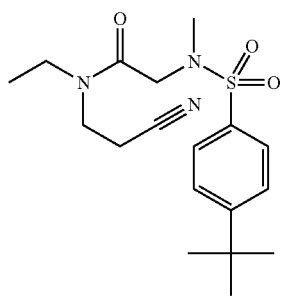

prepared by reaction of [(4-tert-butyl-benzenesulfonyl)-p-tolyl-amino]-acetic acid with 3-ethylamino-propionitrile
LC-MS: rt=1.04 min, 442 (M+1, ES+).

EXAMPLE 64

N-Benzyl-2-[(4-tert-butyl-benzenesulfonyl)-p-tolyl-amino]-N-(4-hydroxy-butyl)-acetamide

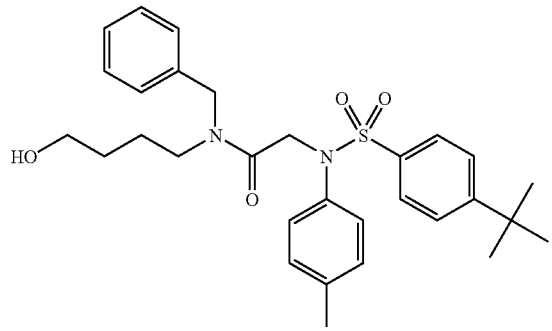

prepared by reaction of [(4-tert-butyl-benzenesulfonyl)-p-tolyl-amino]-acetic acid with 4-benzylamino-butan-1-ol
LC-MS: rt=1.05 min, 523 (M+1, ES+).

EXAMPLE 65

N-Benzyl-2-[(4-tert-butyl-benzenesulfonyl)-p-tolyl-amino]-N-(2-cyano-ethyl)-acetamide

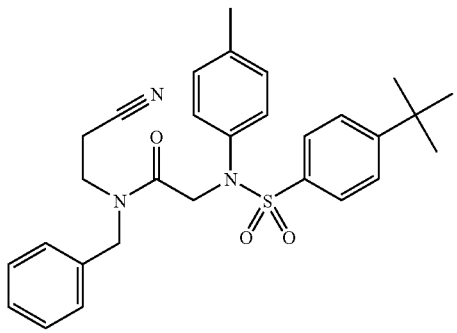

prepared by reaction of [(4-tert-butyl-benzenesulfonyl)-p-tolyl-amino]-acetic acid with 3-benzylamino-propionitrile
LC-MS: rt=1.09 min, 504 (M+1, ES+).

EXAMPLE 66

2-[(4-tert-Butyl-benzenesulfonyl)-p-tolyl-amino]-N-ethyl-N-pyridin-2-ylmethyl-acetamide

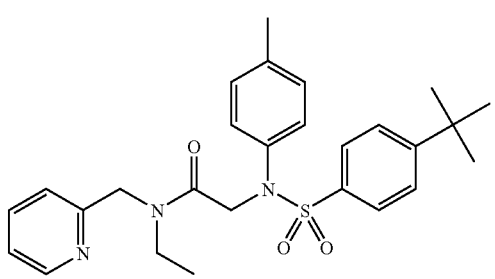

prepared by reaction of [(4-tert-butyl-benzenesulfonyl)-p-tolyl-amino]-acetic acid with ethyl-pyridin-2-ylmethyl-amine
LC-MS: rt=0.92 min, 480 (M+1, ES+).

EXAMPLE 67

2-[(4-tert-Butyl-benzenesulfonyl)-p-tolyl-amino]-N-ethyl-N-pyridin-3-ylmethyl-acetamide

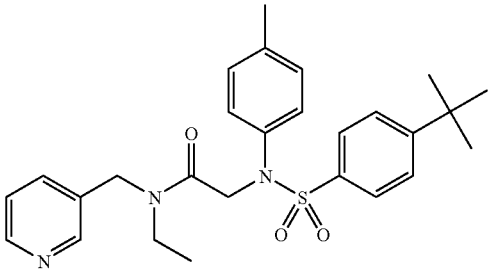

prepared by reaction of [(4-tert-butyl-benzenesulfonyl)-p-tolyl-amino]-acetic acid with ethyl-pyridin-3-ylmethyl-amine
LC-MS: rt=0.88 min, 480 (M+1, ES+).

EXAMPLE 68

2-[(4-tert-Butyl-benzenesulfonyl)-p-tolyl-amino]-N-(4-cyano-benzyl)-N-ethyl-acetamide

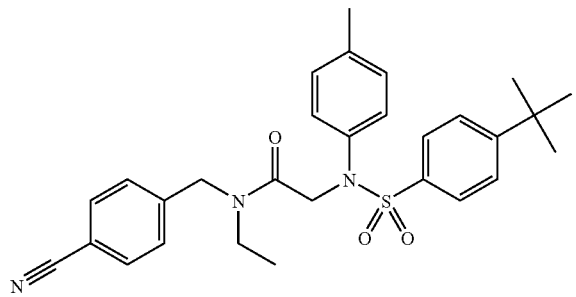

prepared by reaction of [(4-tert-butyl-benzenesulfonyl)-p-tolyl-amino]-acetic acid with 4-ethylaminomethyl-benzonitrile
LC-MS: rt=1.10 min, 504 (M+1, ES+).

EXAMPLE 69

2-[(4-tert-Butyl-benzenesulfonyl)-p-tolyl-amino]-N-ethyl-N-(1-methyl-1H-pyrrol-2-ylmethyl)-acetamide

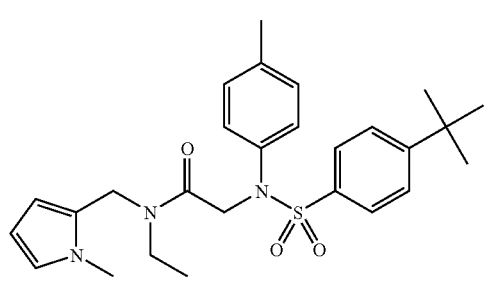

prepared by reaction of [(4-tert-butyl-benzenesulfonyl)-p-tolyl-amino]-acetic acid with ethyl-(1-methyl-1H-pyrrol-2-ylmethyl)-amine
LC-MS: rt=1.11 min, 482 (M+1, ES+).

EXAMPLE 70

2-[(4-tert-Butyl-benzenesulfonyl)-p-tolyl-amino]-N-ethyl-N-(1H-imidazol-2-ylmethyl)-acetamide

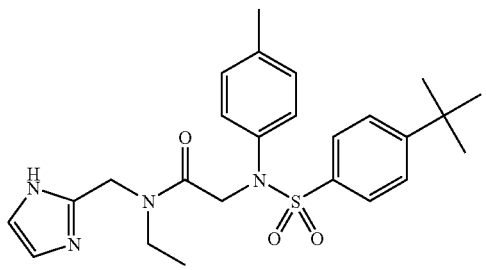

prepared by reaction of [(4-tert-butyl-benzenesulfonyl)-p-tolyl-amino]-acetic acid with ethyl-(1H-imidazol-2-ylmethyl)-amine LC-MS: rt=0.85 min, 469 (M+1, ES+).

EXAMPLE 71

2-[(4-tert-Butyl-benzenesulfonyl)-p-tolyl-amino]-N-ethyl-N-(6-methyl-pyridin-2-ylmethyl)-acetamide

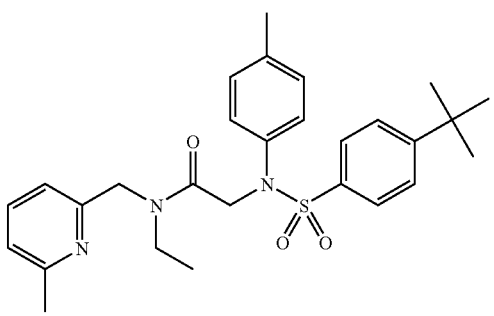

prepared by reaction of [(4-tert-butyl-benzenesulfonyl)-p-tolyl-amino]-acetic acid with ethyl-(6-methyl-pyridin-2-yl-methyl)-amine LC-MS: rt=0.90 min, 494 (M+1, ES+).

EXAMPLE 72

2-[(4-tert-Butyl-benzenesulfonyl)-p-tolyl-amino]-N-ethyl-N-(3H-imidazol-4-ylmethyl)-acetamide

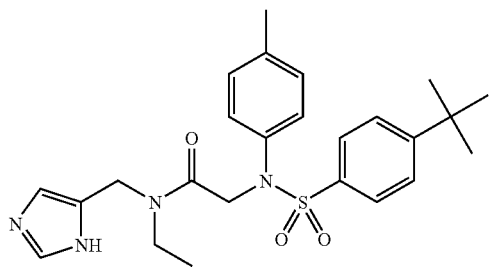

prepared by reaction of [(4-tert-butyl-benzenesulfonyl)-p-tolyl-amino]-acetic acid with ethyl-(3H-imidazol-4-ylm-ethyl)-amine LC-MS: rt=0.85 min, 469 (M+1, ES+).

EXAMPLE 73

2-[(4-tert-Butyl-benzenesulfonyl)-p-tolyl-amino]-N-ethyl-N-thiazol-2-ylmethyl-acetamide

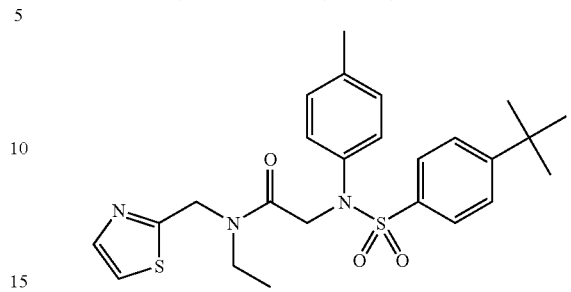

prepared by reaction of [(4-tert-butyl-benzenesulfonyl)-p-tolyl-amino]-acetic acid with ethyl-thiazol-2-ylmethyl-amine LC-MS: rt=1.06 min, 486 (M+1, ES+).

EXAMPLE 74

2-[(4-tert-Butyl-benzenesulfonyl)-p-tolyl-amino]-N-ethyl-N-(1H-indol-3-ylmethyl)-acetamide

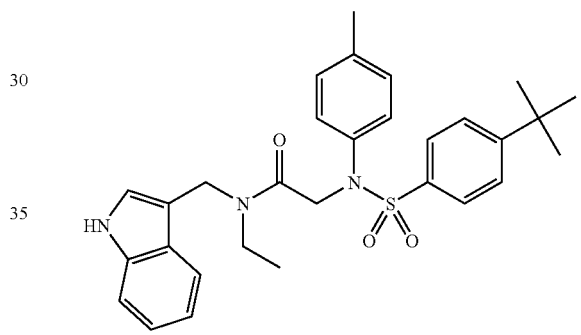

prepared by reaction of [(4-tert-butyl-benzenesulfonyl)-p-tolyl-amino]-acetic acid with ethyl-(1H-indol-3-ylmethyl)-amine LC-MS: rt=1.09 min, 518 (M+1, ES+).

EXAMPLE 75

2-[(4-tert-Butyl-benzenesulfonyl)-quinolin-6-yl-amino]-N,N-diethyl-acetamide

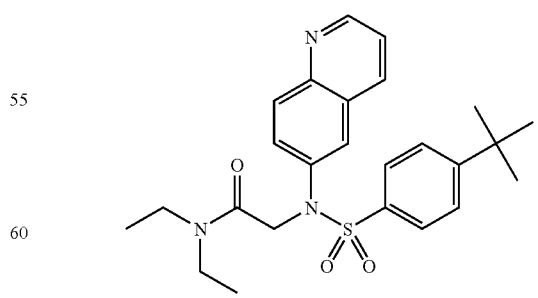

prepared by reaction of [(4-tert-butyl-benzenesulfonyl)-quinolin-6-yl-amino]-acetic acid with diethylamine LC-MS: rt=0.92 min, 454 (M+1, ES+).

EXAMPLE 76

N-Benzyl-2-[(4-tert-butyl-benzenesulfonyl)-quinolin-6-yl-amino]-N-(2-hydroxy-ethyl)-acetamide

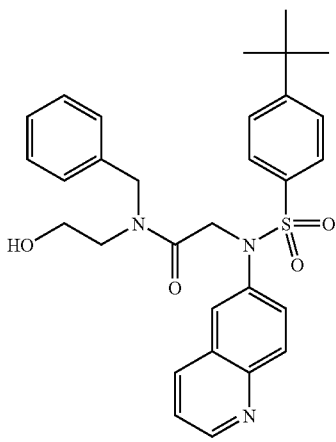

prepared by reaction of [(4-tert-butyl-benzenesulfonyl)-quinolin-6-yl-amino]-acetic acid with 2-benzylamino-ethanol LC-MS: rt=0.90 min, 532 (M+1, ES+).

EXAMPLE 77

2-[(4-tert-Butyl-benzenesulfonyl)-quinolin-6-yl-amino]-N-ethyl-N-pyridin-3-ylmethyl-acetamide

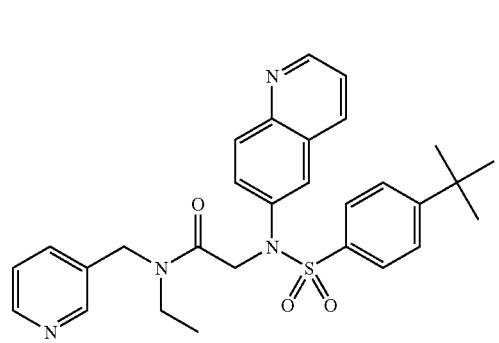

prepared by reaction of [(4-tert-butyl-benzenesulfonyl)-quinolin-6-yl-amino]-acetic acid with ethyl-pyridin-3-ylmethyl-amine LC-MS: rt=0.78 min, 517 (M+1, ES+).

EXAMPLE 78

2-[(4-tert-Butyl-benzenesulfonyl)-quinolin-6-yl-amino]-N-ethyl-N-thiazol-2-ylmethyl-acetamide

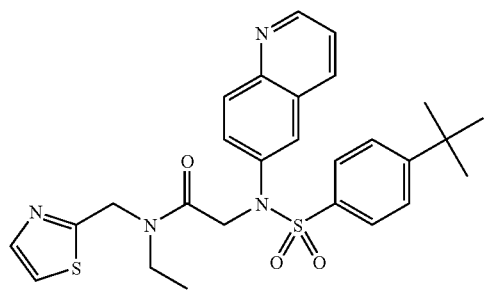

prepared by reaction of [(4-tert-butyl-benzenesulfonyl)-quinolin-6-yl-amino]-acetic acid with ethyl-thiazol-2-ylmethyl-amine LC-MS: rt=0.91 min, 523 (M+1, ES+).

EXAMPLE 79

2-[(4-tert-Butyl-benzenesulfonyl)-quinolin-6-yl-amino]-N-ethyl-N-(2-hydroxy-ethyl)-acetamide

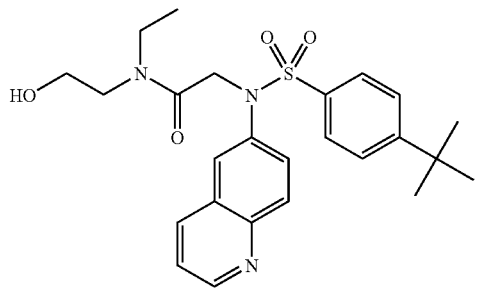

prepared by reaction of [(4-tert-butyl-benzenesulfonyl)-quinolin-6-yl-amino]-acetic acid with 2-ethylamino-ethanol LC-MS: rt=0.81 min, 470 (M+1, ES+).

EXAMPLE 80

N-Benzyl-2-[(4-tert-butyl-benzenesulfonyl)-quinolin-6-yl-amino]-N-ethyl-acetamide

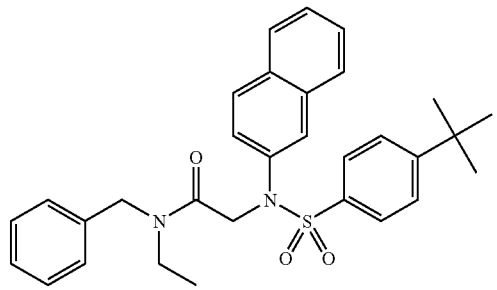

prepared by reaction of [(4-tert-butyl-benzenesulfonyl)-quinolin-6-yl-amino]-acetic acid with benzyl-ethyl-amine
LC-MS: rt=1.00 min, 516 (M+1, ES+).

EXAMPLE 81

2-[(4-tert-Butyl-benzenesulfonyl)-quinolin-6-yl-amino]-N-ethyl-N-(6-methyl-pyridin-2-ylmethyl)-acetamide

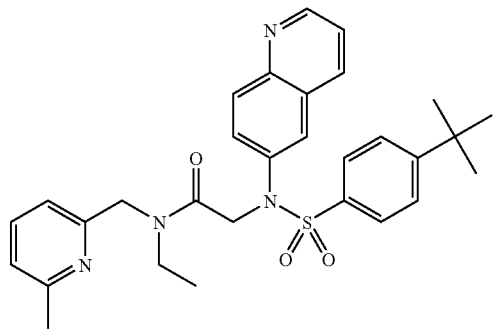

prepared by reaction of [(4-tert-butyl-benzenesulfonyl)-quinolin-6-yl-amino]-acetic acid with ethyl-(6-methyl-pyridin-2-ylmethyl)-amine
LC-MS: rt=0.79 min, 531 (M+1, ES+).

EXAMPLE 82

2-[(4-tert-Butyl-benzenesulfonyl)-(3-dimethylamino-phenyl)-amino]-N,N-diethyl-acetamide

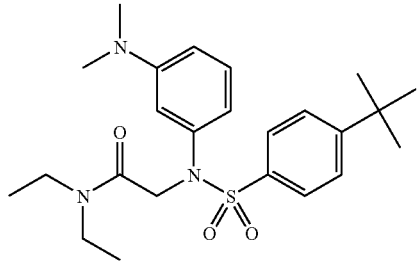

prepared by reaction of [(4-tert-butyl-benzenesulfonyl)-(3-dimethylamino-phenyl)-amino]-acetic acid with diethylamine
LC-MS: rt=0.96 min, 446 (M+1, ES+).

EXAMPLE 83

2-[(4-tert-Butyl-benzenesulfonyl)-(3-dimethylamino-phenyl)-amino]-N-ethyl-N-pyridin-2-ylmethyl-acetamide

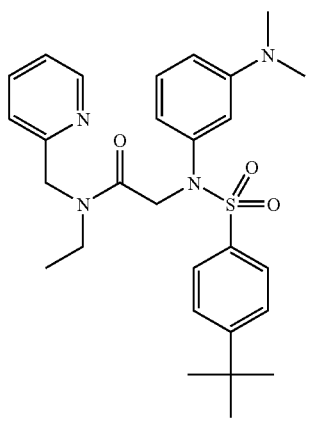

prepared by reaction of [(4-tert-butyl-benzenesulfonyl)-(3-dimethylamino-phenyl)-amino]-acetic acid with ethyl-pyridin-2-ylmethyl-amine
LC-MS: rt=0.86 min, 509 (M+1, ES+).

EXAMPLE 84

N-Benzyl-2-[(4-tert-butyl-benzenesulfonyl)-(3-dimethylamino-phenyl)-amino]-N-(2-hydroxy-ethyl)-acetamide

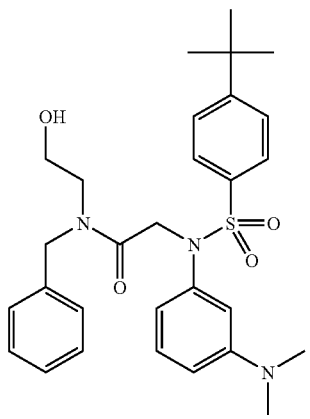

prepared by reaction of [(4-tert-butyl-benzenesulfonyl)-(3-dimethylamino-phenyl)-amino]-acetic acid with 2-benzylamino-ethanol
LC-MS: rt=0.95 min, 524 (M+1, ES+).

EXAMPLE 85

2-[(4-tert-Butyl-benzenesulfonyl)-(3-dimethylamino-phenyl)-amino]-N-ethyl-N-pyridin-3-ylmethyl-acetamide

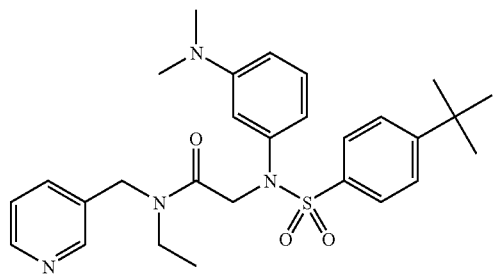

prepared by reaction of [(4-tert-butyl-benzenesulfonyl)-(3-dimethylamino-phenyl)-amino]-acetic acid with ethyl-pyridin-3-ylmethyl-amine LC-MS: rt=0.82 min, 509 (M+1, ES+).

EXAMPLE 86

2-[(4-tert-Butyl-benzenesulfonyl)-(3-dimethylamino-phenyl)-amino]-N-ethyl-N-thiazol-2-ylmethyl-acetamide

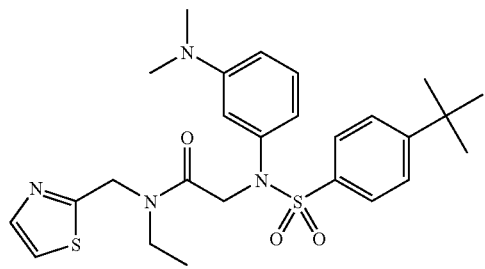

prepared by reaction of [(4-tert-butyl-benzenesulfonyl)-(3-dimethylamino-phenyl)-amino]-acetic acid with ethyl-thiazol-2-ylmethyl-amine LC-MS: rt=0.96 min, 515 (M+1, ES+).

EXAMPLE 87

2-[(4-tert-Butyl-benzenesulfonyl)-(3-dimethylamino-phenyl)-amino]-N-ethyl-N-(6-methyl-pyridin-2-ylmethyl)-acetamide

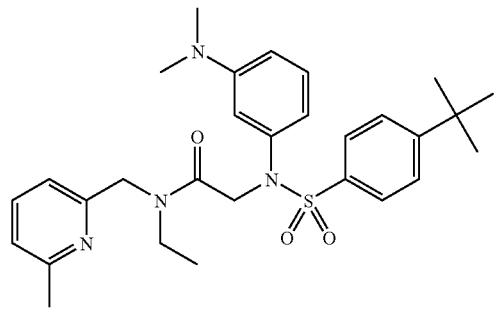

prepared by reaction of [(4-tert-butyl-benzenesulfonyl)-(3-dimethylamino-phenyl)-amino]-acetic acid with ethyl-(6-methyl-pyridin-2-ylmethyl)-amine LC-MS: rt=0.85 min, 523 (M+1, ES+).

EXAMPLE 88

2-[(4-tert-Butyl-benzenesulfonyl)-(3-dimethylamino-phenyl)-amino]-N-ethyl-N-(2-hydroxy-ethyl)-acetamide

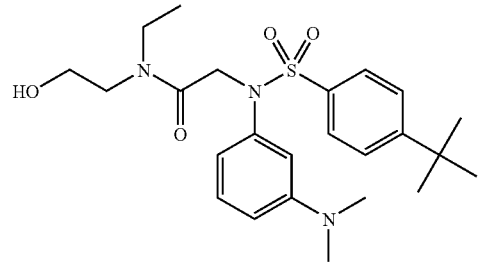

prepared by reaction of [(4-tert-butyl-benzenesulfonyl)-(3-dimethylamino-phenyl)-amino]-acetic acid with 2-ethylamino-ethanol LC-MS: rt=0.85 min, 462 (M+1, ES+).

EXAMPLE 89

2-[(4-tert-Butyl-benzenesulfonyl)-(3-dimethylamino-phenyl)-amino]-N-ethyl-N-(1H-imidazol-2-ylm-ethyl)-acetamide

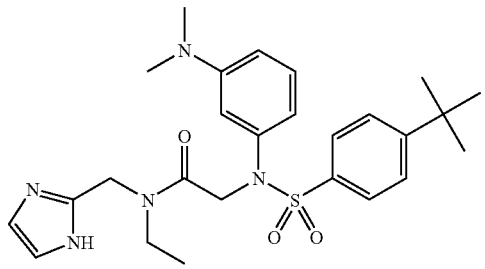

prepared by reaction of [(4-tert-butyl-benzenesulfonyl)-(3-dimethylamino-phenyl)-amino]-acetic acid with ethyl-(1H-imidazol-2-ylmethyl)-amine
LC-MS: rt=0.80 min, 498 (M+1, ES+).

EXAMPLE 90

N-Benzyl-2-[(4-tert-butyl-benzenesulfonyl)-(3-dimethylamino-phenyl)-amino]-N-ethyl-acetamide

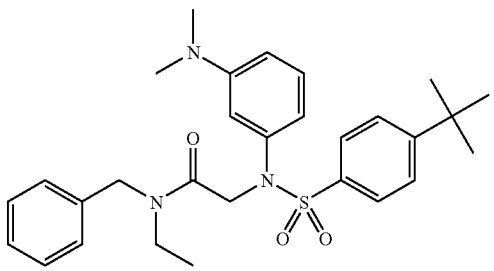

prepared by reaction of [(4-tert-butyl-benzenesulfonyl)-(3-dimethylamino-phenyl)-amino]-acetic acid with benzyl-ethyl-amine
LC-MS: rt=1.05 min, 508 (M+1, ES+).

EXAMPLE 91

2-[(4-tert-Butyl-benzenesulfonyl)-isoquinolin-5-yl-amino]-N,N-diethyl-acetamide

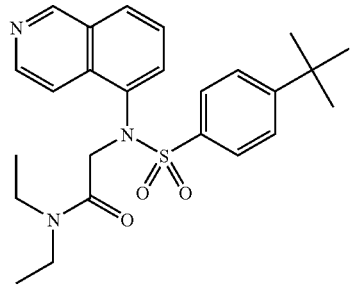

prepared by reaction of [(4-tert-butyl-benzenesulfonyl)-isoquinolin-5-yl-amino]-acetic acid with diethylamine
LC-MS: rt=0.86 min, 454 (M+1, ES+).

EXAMPLE 92

2-[(4-tert-Butyl-benzenesulfonyl)-p-tolyl-amino]-N-(4-dimethylamino-benzyl)-N-ethyl-acetamide

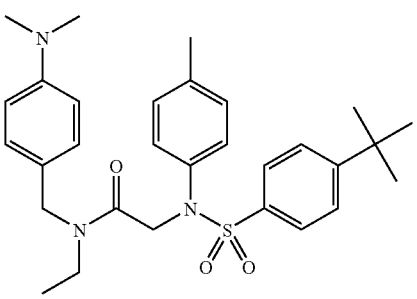

prepared by reaction of [(4-tert-butyl-benzenesulfonyl)-p-tolyl-amino]-acetic acid with (4-ethylaminomethyl-phenyl)-dimethyl-amine
LC-MS: rt=0.93 min, 522 (M+1, ES+).

EXAMPLE 93

2-[(4-tert-Butyl-benzenesulfonyl)-p-tolyl-amino]-N-ethyl-N-(3-hydroxy-benzyl)-acetamide

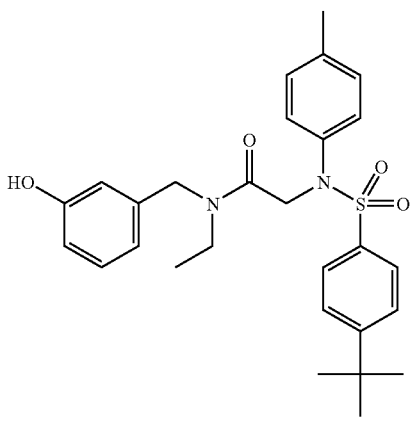

prepared by reaction of [(4-tert-butyl-benzenesulfonyl)-p-tolyl-amino]-acetic acid with 3-ethylaminomethyl-phenol
LC-MS: rt=1.05 min, 495 (M+1, ES+).

EXAMPLE 94

2-[(4-tert-Butyl-benzenesulfonyl)-p-tolyl-amino]-N-ethyl-N-quinolin-3-ylmethyl-acetamide

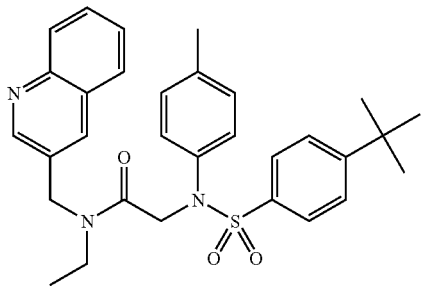

prepared by reaction of [(4-tert-butyl-benzenesulfonyl)-p-tolyl-amino]-acetic acid with ethyl-quinolin-3-ylmethyl-amine LC-MS: rt=0.96 min, 530 (M+1, ES+).

EXAMPLE 95

2-[(4-tert-Butyl-benzenesulfonyl)-p-tolyl-amino]-N-ethyl-N-quinolin-4-ylmethyl-acetamide

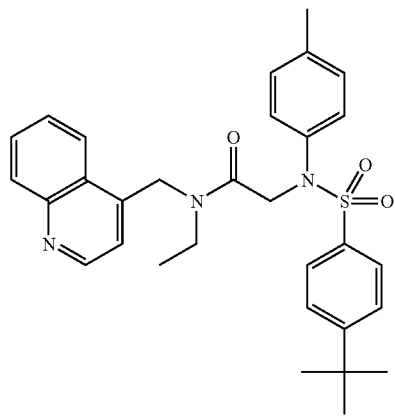

prepared by reaction of [(4-tert-butyl-benzenesulfonyl)-p-tolyl-amino]-acetic acid with ethyl-quinolin-4-ylmethyl-amine LC-MS: rt=0.93 min, 530 (M+1, ES+).

EXAMPLE 96

2-[(4-tert-Butyl-benzenesulfonyl)-diethylcarbamoyl-methyl-amino]-benzamide

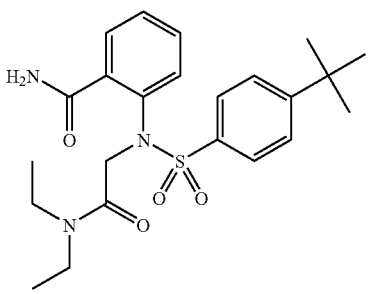

prepared by reaction of [(4-tert-butyl-benzenesulfonyl)-(2-carbamoyl-phenyl)-amino]-acetic acid with diethylamine LC-MS: rt=0.96 min, 446 (M+1, ES+).

EXAMPLE 97

2-{(4-tert-Butyl-benzenesulfonyl)-[(ethyl-thiazol-2-ylmethyl-carbamoyl)-methyl]-amino}-benzamide

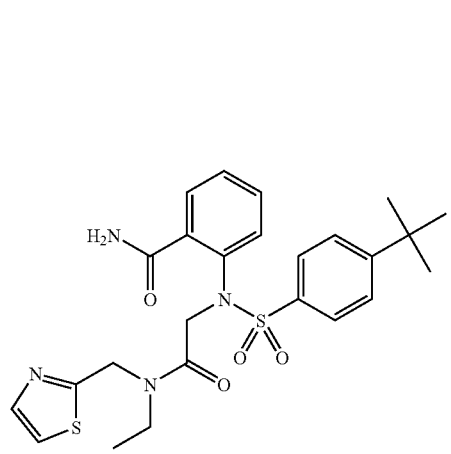

prepared by reaction of [(4-tert-butyl-benzenesulfonyl)-(2-carbamoyl-phenyl)-amino]-acetic acid with ethyl-thiazol-2-ylmethyl-amine LC-MS: rt=0.94 min, 515 (M+1, ES+).

EXAMPLE 98

2-((4-tert-Butyl-benzenesulfonyl)-{[ethyl-(6-methyl-pyridin-2-ylmethyl)-carbamoyl]-methyl}-amino)-benzamide

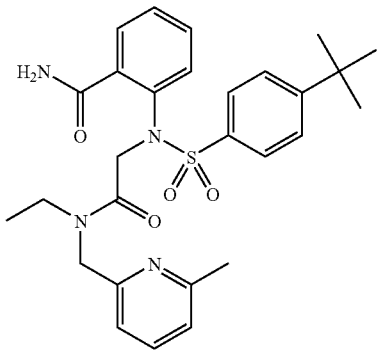

prepared by reaction of [(4-tert-butyl-benzenesulfonyl)-(2-carbamoyl-phenyl)-amino]-acetic acid with ethyl-(6-methyl-pyridin-2-ylmethyl)-amine
LC-MS: rt=0.80 min, 523 (M+1, ES+).

EXAMPLE 99

2-[[(Benzyl-ethyl-carbamoyl)-methyl]-(4-tert-butyl-benzenesulfonyl)-amino]-benzamide

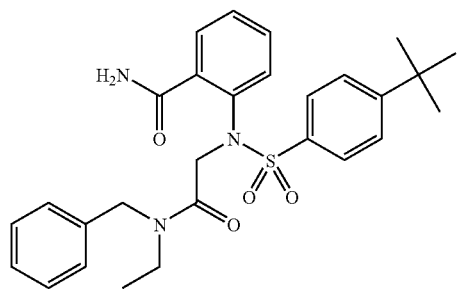

prepared by reaction of [(4-tert-butyl-benzenesulfonyl)-(2-carbamoyl-phenyl)-amino]-acetic acid with benzyl-ethyl-amine
LC-MS: rt=1.02 min, 508 (M+1, ES+).

EXAMPLE 100

2-[(4-tert-Butyl-benzenesulfonyl)-(1H-indazol-6-yl)-amino]-N,N-diethyl-acetamide

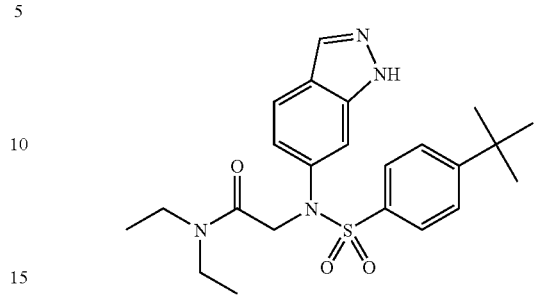

prepared by reaction of [(4-tert-butyl-benzenesulfonyl)-(1H-indazol-6-yl)-amino]-acetic acid with diethylamine
LC-MS: rt=0.98 min, 443 (M+1, ES+).

EXAMPLE 101

N-Benzyl-2-[(4-tert-butyl-benzenesulfonyl)-(1H-indazol-6-yl)-amino]-N-(2-hydroxy-ethyl)-acetamide

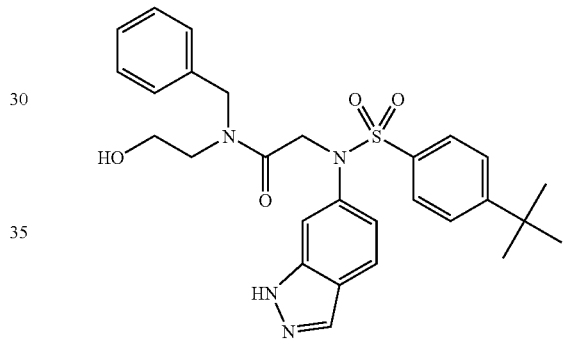

prepared by reaction of [(4-tert-butyl-benzenesulfonyl)-(1H-indazol-6-yl)-amino]-acetic acid with 2-benzylamino-ethanol
LC-MS: rt=0.97 min, 521 (M+1, ES+).

EXAMPLE 102

2-[(4-tert-Butyl-benzenesulfonyl)-(1H-indazol-6-yl)-amino]-N-ethyl-N-thiazol-2-ylmethyl-acetamide

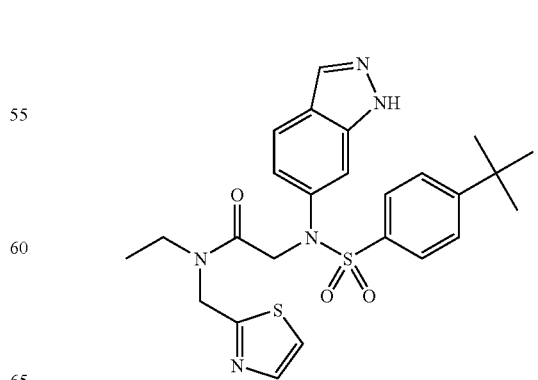

prepared by reaction of [(4-tert-butyl-benzenesulfonyl)-(1H-indazol-6-yl)-amino]-acetic acid with ethyl-thiazol-2-ylmethyl-amine
  LC-MS: rt=0.97 min, 512 (M+1, ES+).

EXAMPLE 103

2-[(4-tert-Butyl-benzenesulfonyl)-(1H-indazol-6-yl)-amino]-N-ethyl-N-(6-methyl-pyridin-2-ylmethyl)-acetamide

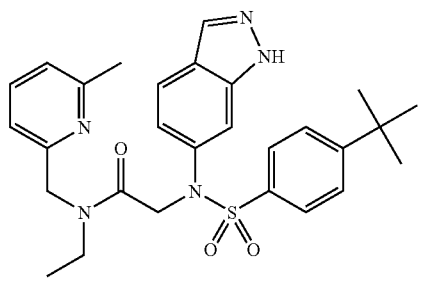

prepared by reaction of [(4-tert-butyl-benzenesulfonyl)-(1H-indazol-6-yl)-amino]-acetic acid with ethyl-(6-methyl-pyridin-2-ylmethyl)-amine
  LC-MS: rt=0.75 min, 520 (M+1, ES+).

EXAMPLE 104

2-[(4-tert-Butyl-benzenesulfonyl)-(1H-indazol-6-yl)-amino]-N-ethyl-N-(2-hydroxy-ethyl)-acetamide

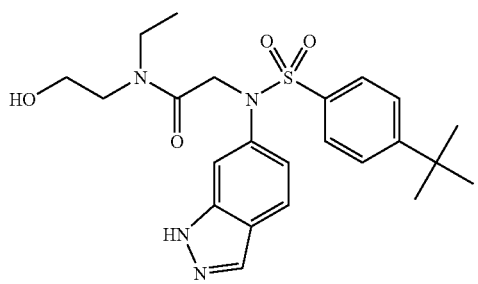

prepared by reaction of [(4-tert-butyl-benzenesulfonyl)-(1H-indazol-6-yl)-amino]-acetic acid with 2-ethylamino-ethanol
  LC-MS: rt=0.82 min, 459 (M+1, ES+).

EXAMPLE 105

2-[(4-tert-Butyl-benzenesulfonyl)-(1H-indazol-6-yl)-amino]-N-ethyl-N-pyridin-2-ylmethyl-acetamide

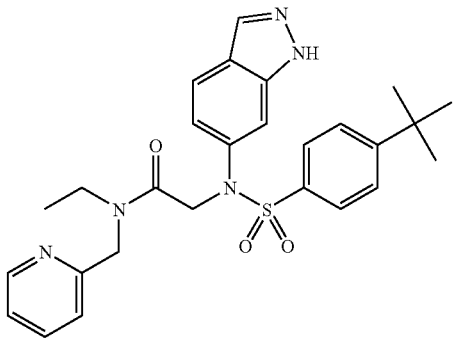

prepared by reaction of [(4-tert-butyl-benzenesulfonyl)-(1H-indazol-6-yl)-amino]-acetic acid with ethyl-pyridin-2-ylmethyl-amine
  LC-MS: rt=0.78 min, 506 (M+1, ES+).

EXAMPLE 106

2-[(4-tert-Butyl-benzenesulfonyl)-(1H-indazol-6-yl)-amino]-N-ethyl-N-pyridin-3-ylmethyl-acetamide

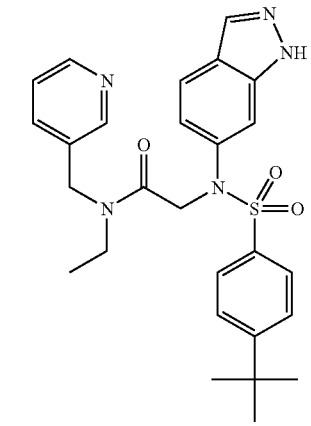

prepared by reaction of [(4-tert-butyl-benzenesulfonyl)-(1H-indazol-6-yl)-amino]-acetic acid with ethyl-pyridin-3-ylmethyl-amine
  LC-MS: rt=0.81 min, 506 (M+1, ES+).

EXAMPLE 107

2-[(4-tert-Butyl-benzenesulfonyl)-p-tolyl-amino]-N-(2-hydroxy-ethyl)-N-pyridin-2-ylmethyl-acetamide

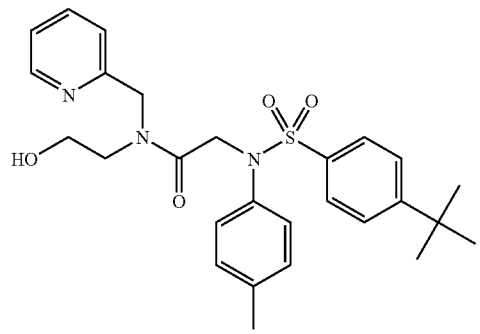

prepared by reaction of [(4-tert-butyl-benzenesulfonyl)-p-tolyl-amino]-acetic acid with 2-[(pyridin-2-ylmethyl)-amino]-ethanol LC-MS: rt=0.86 min, 496 (M+1, ES+).

EXAMPLE 108

2-[(4-tert-Butyl-benzenesulfonyl)-p-tolyl-amino]-N-(3-hydroxy-propyl)-N-pyridin-2-ylmethyl-acetamide

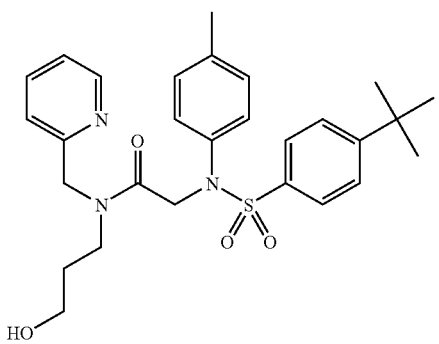

prepared by reaction of [(4-tert-butyl-benzenesulfonyl)-p-tolyl-amino]-acetic acid with 3-[(pyridin-2-ylmethyl)-amino]-propan-1-ol LC-MS: rt=0.87 min, 510 (M+1, ES+).

EXAMPLE 109

2-[(4-tert-Butyl-benzenesulfonyl)-p-tolyl-amino]-N-(3-hydroxy-propyl)-N-quinolin-2-ylmethyl-acetamide

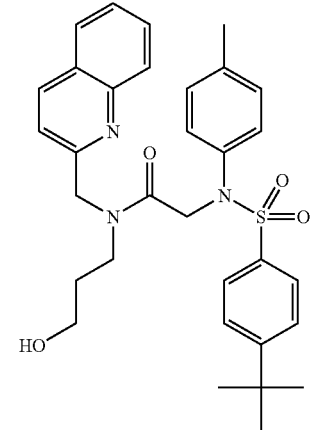

prepared by reaction of [(4-tert-butyl-benzenesulfonyl)-p-tolyl-amino]-acetic acid with 3-[(quinolin-2-ylmethyl)-amino]-propan-1-ol LC-MS: rt=0.95 min, 560 (M+1, ES+).

EXAMPLE 110

2-[(4-tert-Butyl-benzenesulfonyl)-p-tolyl-amino]-N-ethyl-N-quinolin-2-ylmethyl-acetamide

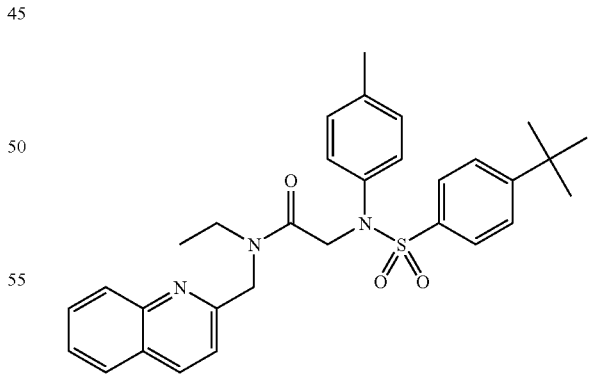

prepared by reaction of [(4-tert-butyl-benzenesulfonyl)-p-tolyl-amino]-acetic acid with ethyl-quinolin-2-ylmethyl-amine LC-MS: rt=1.01 min, 530 (M+1, ES+).

EXAMPLE 111

2-[(4-tert-Butyl-benzenesulfonyl)-(3-dimethylamino-phenyl)-amino]-N-(2-hydroxy-ethyl)-N-pyridin-2-ylmethyl-acetamide

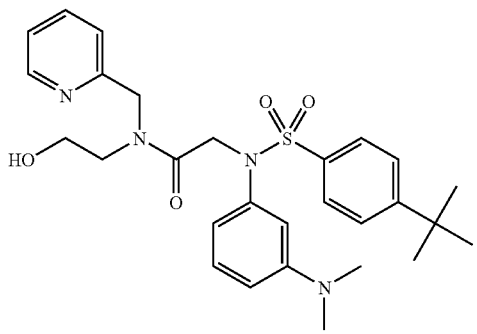

prepared by reaction of [(4-tert-butyl-benzenesulfonyl)-(3-dimethylamino-phenyl)-amino]-acetic acid with 2-[(pyridin-2-ylmethyl)-amino]-ethanol
LC-MS: rt=0.80 min, 525 (M+1, ES+).

EXAMPLE 112

2-[(4-tert-Butyl-benzenesulfonyl)-(3-dimethylamino-phenyl)-amino]-N-(3-hydroxy-propyl)-N-pyridin-2-ylmethyl-acetamide

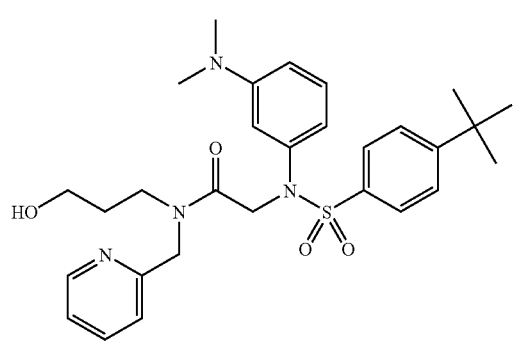

prepared by reaction of [(4-tert-butyl-benzenesulfonyl)-(3-dimethylamino-phenyl)-amino]-acetic acid with 3-[(pyridin-2-ylmethyl)-amino]-propan-1-ol
LC-MS: rt=0.80 min, 539 (M+1, ES+).

EXAMPLE 113

2-[(4-tert-Butyl-benzenesulfonyl)-(3-dimethylamino-phenyl)-amino]-N-(2-hydroxy-ethyl)-N-quinolin-2-ylmethyl-acetamide

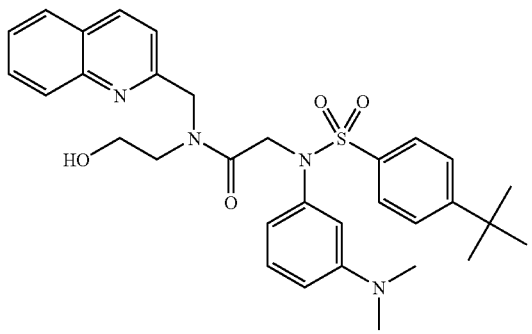

prepared by reaction of [(4-tert-butyl-benzenesulfonyl)-(3-dimethylamino-phenyl)-amino]-acetic acid with 2-[(quinolin-2-ylmethyl)-amino]-ethanol
LC-MS: rt=0.89 min, 575 (M+1, ES+).

EXAMPLE 114

2-[(4-tert-Butyl-benzenesulfonyl)-(3-dimethylamino-phenyl)-amino]-N-(3-hydroxy-propyl)-N-quinolin-2-ylmethyl-acetamide

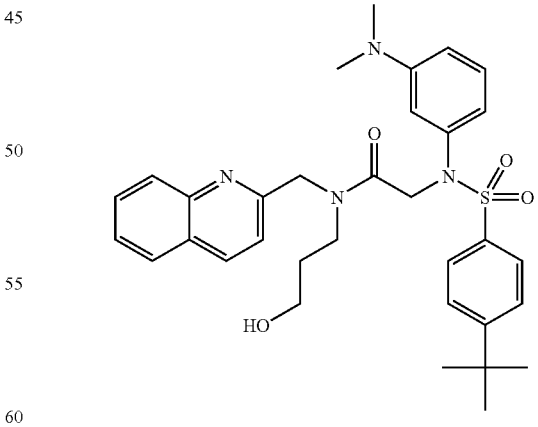

prepared by reaction of [(4-tert-butyl-benzenesulfonyl)-(3-dimethylamino-phenyl)-amino]-acetic acid with 3-[(quinolin-2-ylmethyl)-amino]-propan-1-ol
LC-MS: rt=0.89 min, 589 (M+1, ES+).

EXAMPLE 115

2-[(4-tert-Butyl-benzenesulfonyl)-(3-dimethylamino-phenyl)-amino]-N-ethyl-N-quinolin-2-ylmethyl-acetamide

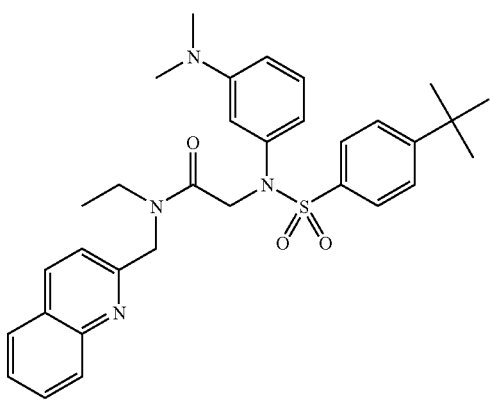

prepared by reaction of [(4-tert-butyl-benzenesulfonyl)-(3-dimethylamino-phenyl)-amino]-acetic acid with ethyl-quinolin-2-ylmethyl-amine
LC-MS: rt=0.96 min, 559 (M+1, ES+).

EXAMPLE 116

2-[(4-tert-Butyl-benzenesulfonyl)-quinolin-6-yl-amino]-N-(2-hydroxy-ethyl)-N-pyridin-2-ylmethyl-acetamide

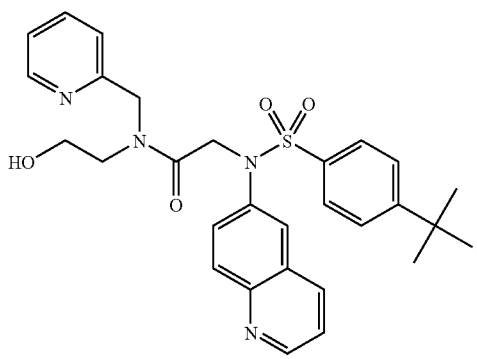

prepared by reaction of [(4-tert-butyl-benzenesulfonyl)-quinolin-6-yl-amino]-acetic acid with 2-[(pyridin-2-ylmethyl)-amino]-ethanol
LC-MS: rt=0.75 min, 533 (M+1, ES+).

EXAMPLE 117

2-[(4-tert-Butyl-benzenesulfonyl)-quinolin-6-yl-amino]-N-(3-hydroxy-propyl)-N-pyridin-2-ylmethyl-acetamide

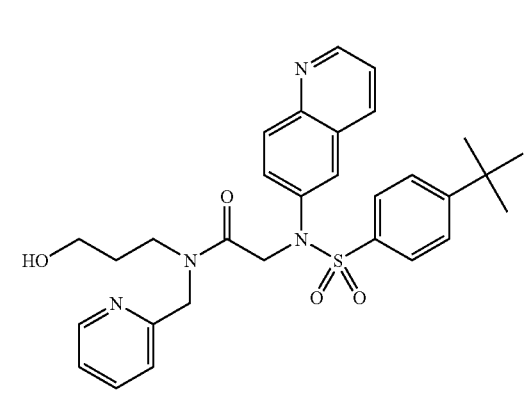

prepared by reaction of [(4-tert-butyl-benzenesulfonyl)-quinolin-6-yl-amino]-acetic acid with 3-[(pyridin-2-ylmethyl)-amino]-propan-1-ol
LC-MS: rt=0.76 min, 547 (M+1, ES+).

EXAMPLE 118

2-[(4-tert-Butyl-benzenesulfonyl)-p-tolyl-amino]-N-ethyl-N-(6-ethylamino-pyridin-2-ylmethyl)-acetamide prepared by reaction of [(4-tert-butyl-benzenesulfonyl)-p-tolyl-amino]-acetic acid with ethyl-(6-ethylaminomethyl-pyridin-2-yl)-amine
LC-MS: rt=0.94 min, 523 (M+1, ES+).

EXAMPLE 119

2-[(4-tert-Butyl-benzenesulfonyl)-p-tolyl-amino]-N-ethyl-N-(6-ethylamino-methyl-pyridin-2-ylmethyl)-acetamide

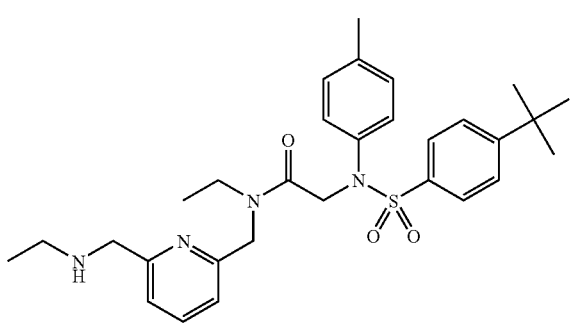

prepared by reaction of [(4-tert-butyl-benzenesulfonyl)-p-tolyl-amino]-acetic acid with ethyl-(6-ethylaminomethyl-pyridin-2-ylmethyl)-amine LC-MS: rt=0.91 min, 537 (M+1, ES+).

EXAMPLE 120

2-[(4-tert-Butyl-benzenesulfonyl)-p-tolyl-amino]-N-(6-dimethylamino-pyridin-2-ylmethyl)-N-ethyl-acetamide

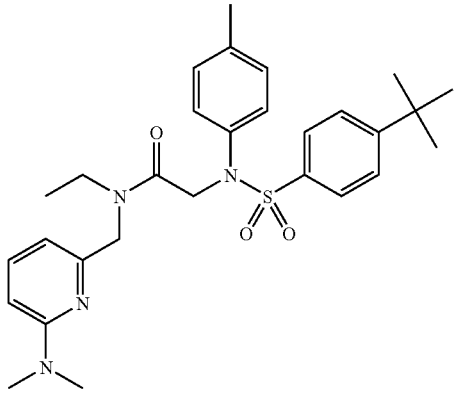

prepared by reaction of [(4-tert-butyl-benzenesulfonyl)-p-tolyl-amino]-acetic acid with (6-ethylaminomethyl-pyridin-2-yl)-dimethyl-amine LC-MS: rt=0.92 min, 523 (M+1, ES+).

EXAMPLE 121

2-[(4-tert-Butyl-benzenesulfonyl)-p-tolyl-amino]-N-ethyl-N-[6-(ethyl-methyl-amino)-pyridin-2-ylmethyl]-acetamide

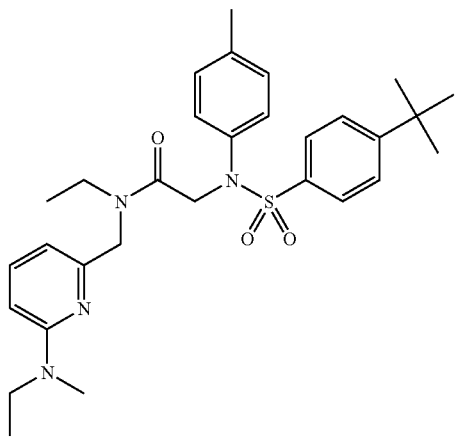

prepared by reaction of [(4-tert-butyl-benzenesulfonyl)-p-tolyl-amino]-acetic acid with ethyl-(6-ethylaminomethyl-pyridin-2-yl)-methyl-amine LC-MS: rt=0.94 min, 537 (M+1, ES+).

EXAMPLE 122

2-[(4-tert-Butyl-benzenesulfonyl)-(3-dimethylamino-phenyl)-amino]-N-(6-dimethylamino-pyridin-2-ylmethyl)-N-ethyl-acetamide

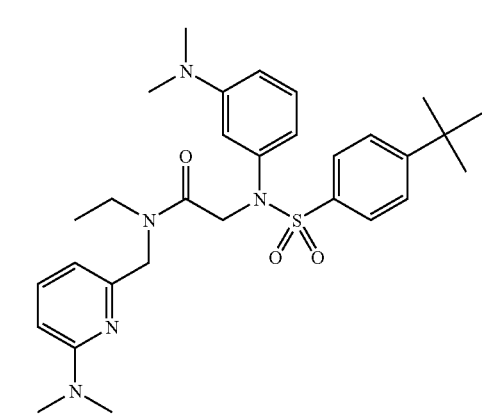

prepared by reaction of [(4-tert-butyl-benzenesulfonyl)-(3-dimethylamino-phenyl)-amino]-acetic acid with (6-ethylaminomethyl-pyridin-2-yl)-dimethyl-amine LC-MS: rt=0.89 min, 552 (M+1, ES+).

EXAMPLE 123

2-[(4-tert-Butyl-benzenesulfonyl)-p-tolyl-amino]-N-cyclopropyl-N-(3-methoxy-benzyl)-acetamide

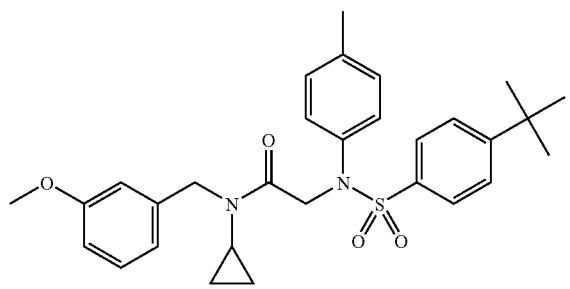

prepared by reaction of [(4-tert-butyl-benzenesulfonyl)-p-tolyl-amino]-acetic acid with cyclopropyl-(3-methoxy-benzyl)-amine LC-MS: rt=1.14 min, 521 (M+1, ES+).

EXAMPLE 124

2-[(4-tert-Butyl-benzenesulfonyl)-p-tolyl-amino]-N-cyclopropyl-N-(2,5-dichloro-benzyl)-acetamide

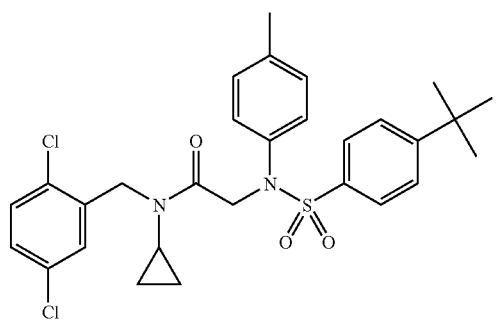

prepared by reaction of [(4-tert-butyl-benzenesulfonyl)-p-tolyl-amino]-acetic acid with cyclopropyl-(2,5-dichloro-benzyl)-amine LC-MS: rt=1.16 min, 559 (M+1, ES+).

EXAMPLE 125

2-[(4-tert-Butyl-benzenesulfonyl)-p-tolyl-amino]-N-cyclopropyl-N-(3,4-dimethoxy-benzyl)-acetamide

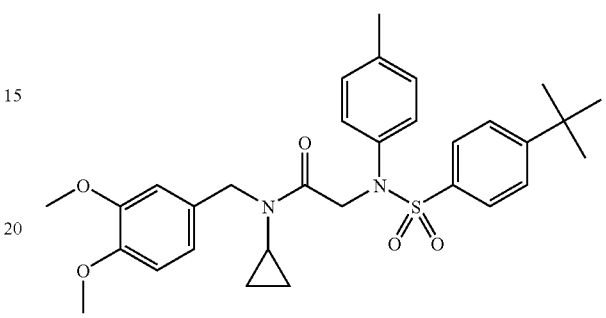

prepared by reaction of [(4-tert-butyl-benzenesulfonyl)-p-tolyl-amino]-acetic acid with cyclopropyl-(3,4-dimethoxy-benzyl)-amine LC-MS: rt=1.12 min, 551 (M+1, ES+).

EXAMPLE 126

2-[(4-tert-Butyl-benzenesulfonyl)-p-tolyl-amino]-N-cyclopropyl-N-(3-methyl-benzyl)-acetamide

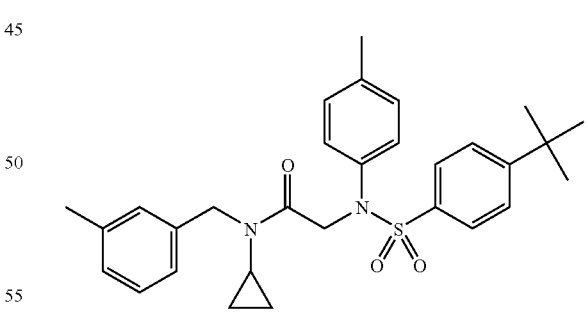

prepared by reaction of [(4-tert-butyl-benzenesulfonyl)-p-tolyl-amino]-acetic acid with cyclopropyl-(3-methyl-benzyl)-amine LC-MS: rt=1.12 min, 505 (M+1, ES+).

EXAMPLE 127

2-[(4-tert-Butyl-benzenesulfonyl)-p-tolyl-amino]-N-cyclopropyl-N-(3,5-dimethoxy-benzyl)-acetamide

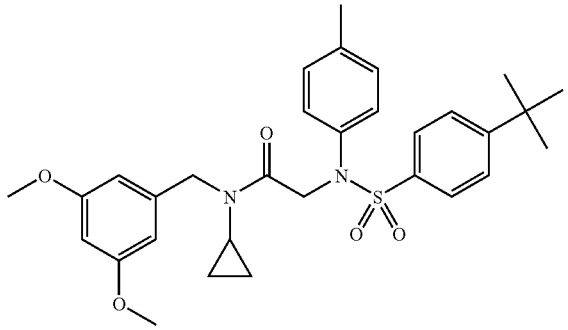

prepared by reaction of [(4-tert-butyl-benzenesulfonyl)-p-tolyl-amino]-acetic acid with cyclopropyl-(3,5-dimethoxy-benzyl)-amine LC-MS: rt=1.15 min, 551 (M+1, ES+).

EXAMPLE 128

2-[(4-tert-Butyl-benzenesulfonyl)-p-tolyl-amino]-N-methyl-N-pyridin-3-ylmethyl-acetamide

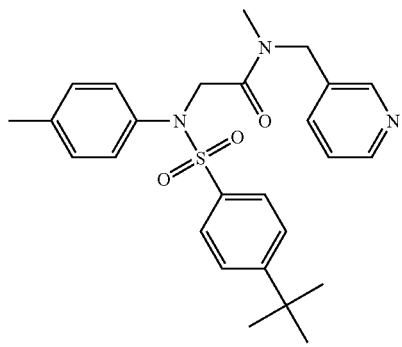

prepared by reaction of [(4-tert-butyl-benzenesulfonyl)-p-tolyl-amino]-acetic acid with methyl-pyridin-3-ylmethyl-amine LC-MS: rt=0.86 min, 466 (M+1, ES+).

EXAMPLE 129

2-[(4-tert-Butyl-benzenesulfonyl)-quinolin-6-yl-amino]-N-cyclopropyl-N-(3-methoxy-benzyl)-acetamide

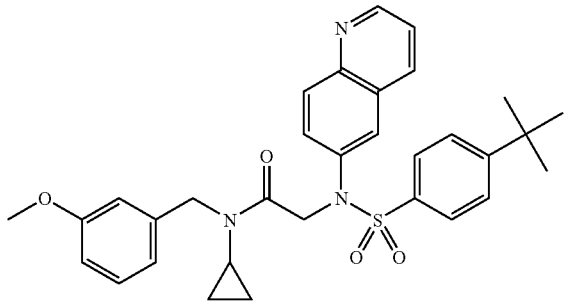

prepared by reaction of [(4-tert-butyl-benzenesulfonyl)-quinolin-6-yl-amino]-acetic acid with cyclopropyl-(3-methoxy-benzyl)-amine LC-MS: rt=1.02 min, 558 (M+1, ES+).

EXAMPLE 130

2-[(4-tert-Butyl-benzenesulfonyl)-quinolin-6-yl-amino]-N-cyclopropyl-N-(3,4-dimethoxy-benzyl)-acetamide

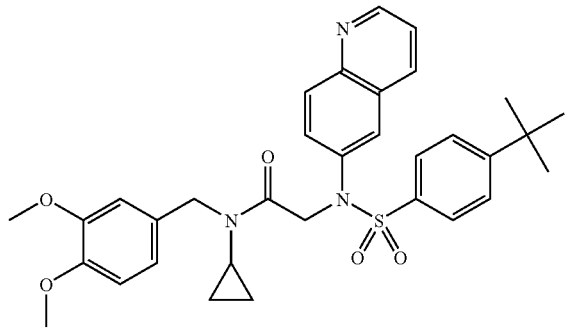

prepared by reaction of [(4-tert-butyl-benzenesulfonyl)-quinolin-6-yl-amino]-acetic acid with cyclopropyl-(3,4-dimethoxy-benzyl)-amine LC-MS: rt=0.99 min, 588 (M+1, ES+).

EXAMPLE 131

2-[(4-tert-Butyl-benzenesulfonyl)-quinolin-6-yl-amino]-N-cyclopropyl-N-(3-methyl-benzyl)-acetamide

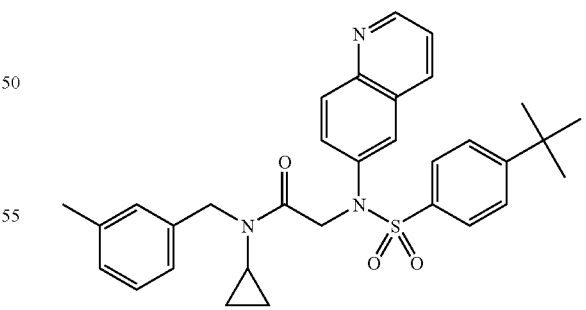

prepared by reaction of [(4-tert-butyl-benzenesulfonyl)-quinolin-6-yl-amino]-acetic acid with cyclopropyl-(3-methyl-benzyl)-amine LC-MS: rt=1.05 min, 542 (M+1, ES+).

EXAMPLE 132

2-[(4-tert-Butyl-benzenesulfonyl)-quinolin-6-yl-amino]-N-cyclopropyl-N-(3,5-dimethoxy-benzyl)-acetamide

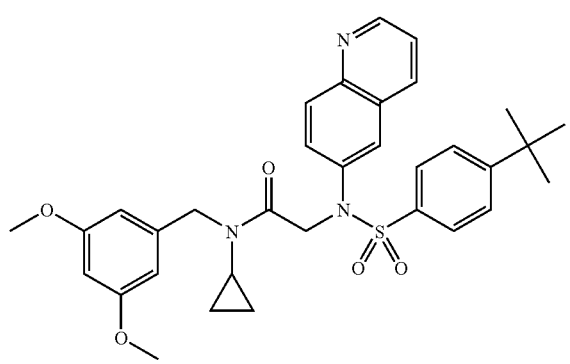

prepared by reaction of [(4-tert-butyl-benzenesulfonyl)-quinolin-6-yl-amino]-acetic acid with cyclopropyl-(3,5-dimethoxy-benzyl)-amine LC-MS: rt=1.02 min, 588 (M+1, ES+).

EXAMPLE 133

2-((4-tert-Butyl-benzenesulfonyl)-{[cyclopropyl-(3-methoxy-benzyl)-carbamoyl]-methyl}-amino)-benzamide

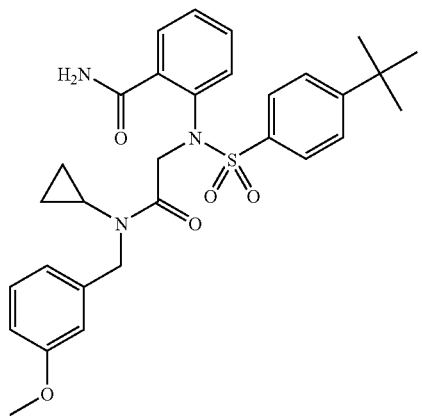

prepared by reaction of [(4-tert-butyl-benzenesulfonyl)-(2-carbamoyl-phenyl)-amino]-acetic acid with cyclopropyl-(3-methoxy-benzyl)-amine LC-MS: rt=1.05 min, 550 (M+1, ES+).

EXAMPLE 134

2-((4-tert-Butyl-benzenesulfonyl)-{[cyclopropyl-(3-methyl-benzyl)-carbamoyl]-methyl}-amino)-benzamide

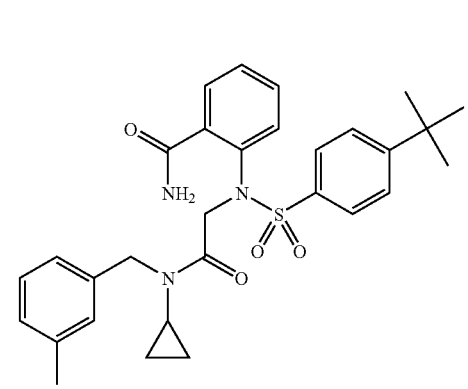

prepared by reaction of [(4-tert-butyl-benzenesulfonyl)-(2-carbamoyl-phenyl)-amino]-acetic acid with cyclopropyl-(3-methyl-benzyl)-amine LC-MS: rt=1.07 min, 534 (M+1, ES+).

EXAMPLE 135

2-[(4-tert-Butyl-benzenesulfonyl)-(3-dimethylamino-phenyl)-amino]-N-cyclopropyl-N-(3-methoxy-benzyl)-acetamide

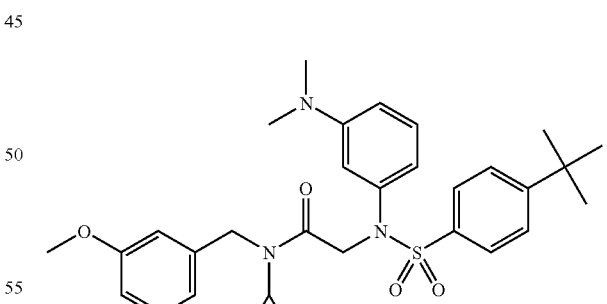

prepared by reaction of [(4-tert-butyl-benzenesulfonyl)-(3-dimethylamino-phenyl)-amino]-acetic acid with cyclopropyl-(3-methoxy-benzyl)-amine LC-MS: rt=1.08 min, 550 (M+1, ES+).

EXAMPLE 136

2-[(4-tert-Butyl-benzenesulfonyl)-(3-dimethylamino-phenyl)-amino]-N-cyclopropyl-N-(3,4-dimethoxy-benzyl)-acetamide

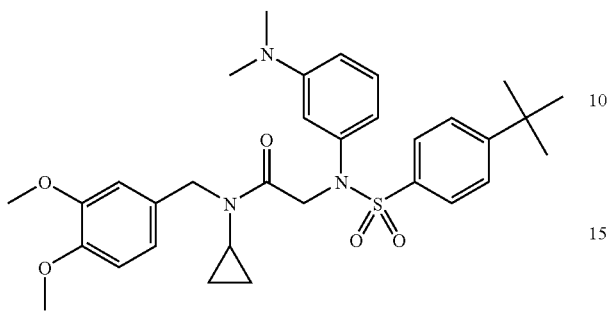

prepared by reaction of [(4-tert-butyl-benzenesulfonyl)-(3-dimethylamino-phenyl)-amino]-acetic acid with cyclopropyl-(3,4-dimethoxy-benzyl)-amine LC-MS: rt=1.05 min, 580 (M+1, ES+).

EXAMPLE 137

2-[(4-tert-Butyl-benzenesulfonyl)-(3-dimethylamino-phenyl)-amino]-N-cyclopropyl-N-(3-methyl-benzyl)-acetamide

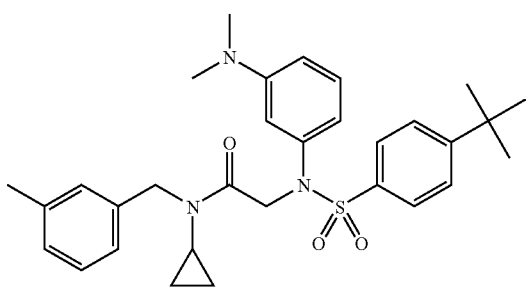

prepared by reaction of [(4-tert-butyl-benzenesulfonyl)-(3-dimethylamino-phenyl)-amino]-acetic acid with cyclopropyl-(3-methyl-benzyl)-amine LC-MS: rt=1.10 min, 534 (M+1, ES+).

EXAMPLE 138

2-[(4-tert-Butyl-benzenesulfonyl)-(3-dimethylamino-phenyl)-amino]-N-cyclopropyl-N-(3,5-dimethoxy-benzyl)-acetamide

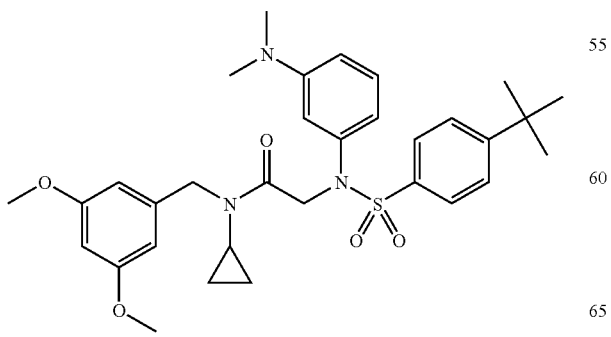

prepared by reaction of [(4-tert-butyl-benzenesulfonyl)-(3-dimethylamino-phenyl)-amino]-acetic acid with cyclopropyl-(3,5-dimethoxy-benzyl)-amine LC-MS: rt=1.08 min, 580 (M+1, ES+).

EXAMPLE 139

2-[(4-tert-Butyl-benzenesulfonyl)-(3-dimethylamino-phenyl)-amino]-N-methyl-N-pyridin-3-ylmethyl-acetamide

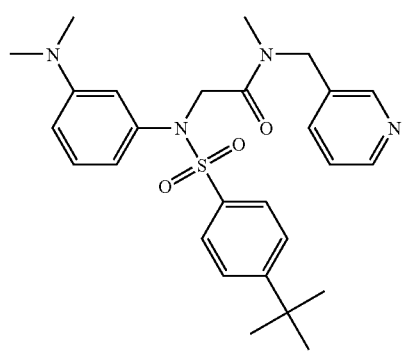

prepared by reaction of [(4-tert-butyl-benzenesulfonyl)-(3-dimethylamino-phenyl)-amino]-acetic acid with methyl-pyridin-3-ylmethyl-amine LC-MS: rt=0.81 min, 495 (M+1, ES+).

EXAMPLE 140

N-Ethyl-2-[(5-isopropyl-pyridine-2-sulfonyl)-p-tolyl-amino]-N-pyridin-2-ylmethyl-acetamide

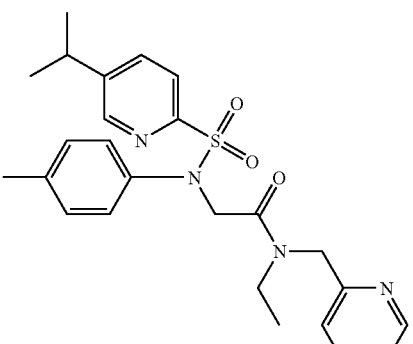

prepared by reaction of [(5-isopropyl-pyridine-2-sulfonyl)-p-tolyl-amino]-acetic acid with ethyl-pyridin-2-ylmethyl-amine LC-MS: rt=0.84 min, 467 (M+1, ES+).

EXAMPLE 141

N-Ethyl-2-[(5-isopropyl-pyridine-2-sulfonyl)-p-tolyl-amino]-N-(6-methyl-pyridin-2-ylmethyl)-acetamide

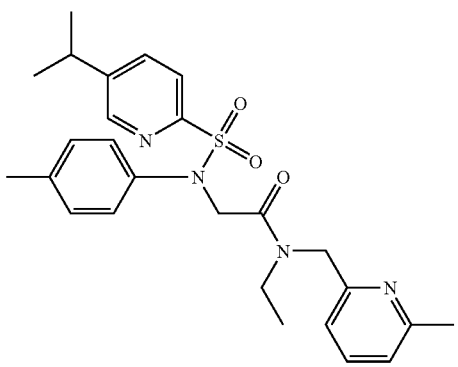

prepared by reaction of [(5-isopropyl-pyridine-2-sulfonyl)-p-tolyl-amino]-acetic acid with ethyl-(6-methyl-pyridin-2-yl-methyl)-amine LC-MS: rt=0.83 min, 481 (M+1, ES+).

EXAMPLE 142

N-(2-Hydroxy-ethyl)-2-[(5-isopropyl-pyridine-2-sulfonyl)-p-tolyl-amino]-N-pyridin-2-ylmethyl-acetamide

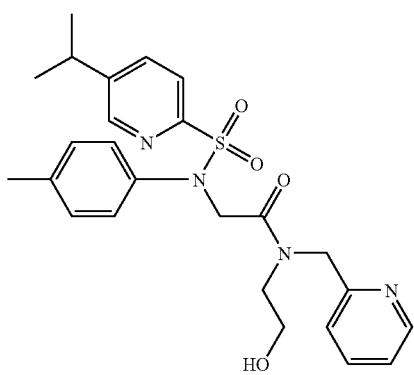

prepared by reaction of [(5-isopropyl-pyridine-2-sulfonyl)-p-tolyl-amino]-acetic acid with 2-[(pyridin-2-ylmethyl)-amino]-ethanol LC-MS: rt=0.79 min, 483 (M+1, ES+).

EXAMPLE 143

N-Ethyl-2-[(5-isopropyl-pyridine-2-sulfonyl)-p-tolyl-amino]-N-thiazol-2-ylmethyl-acetamide

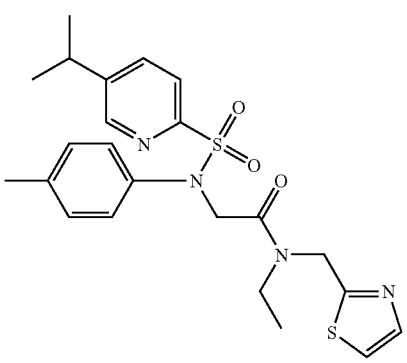

prepared by reaction of [(5-isopropyl-pyridine-2-sulfonyl)-p-tolyl-amino]-acetic acid with ethyl-thiazol-2-ylmethyl-amine LC-MS: rt=0.99 min, 473 (M+1, ES+).

EXAMPLE 144

N-Ethyl-2-[(2-methoxy-phenyl)-(toluene-2-sulfonyl)-amino]-N-thiazol-2-ylmethyl-acetamide

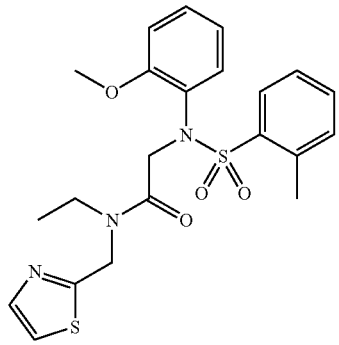

prepared by reaction of [(2-methoxy-phenyl)-(toluene-2-sulfonyl)-amino]-acetic acid with ethyl-thiazol-2-ylmethyl-amine LC-MS: rt=0.96 min, 460 (M+1, ES+).

EXAMPLE 145

N-Ethyl-2-[(2-methoxy-phenyl)-(toluene-2-sulfonyl)-amino]-N-(6-methyl-pyridin-2-ylmethyl)-acetamide

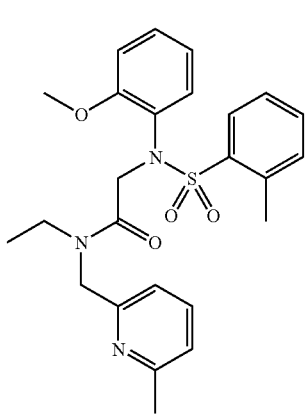

prepared by reaction of [(2-methoxy-phenyl)-(toluene-2-sulfonyl)-amino]-acetic acid with ethyl-(6-methyl-pyridin-2-ylmethyl)-amine LC-MS: rt=0.80 min, 468 (M+1, ES+).

EXAMPLE 146

N-Benzyl-N-(2-hydroxy-ethyl)-2-[(2-methoxy-phenyl)-(toluene-2-sulfonyl)-amino]-acetamide

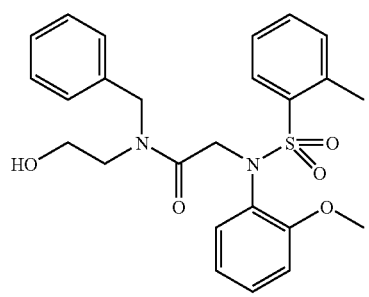

prepared by reaction of [(2-methoxy-phenyl)-(toluene-2-sulfonyl)-amino]-acetic acid with 2-benzylamino-ethanol LC-MS: rt=0.96 min, 469 (M+1, ES+).

EXAMPLE 147

N-Ethyl-2-[(2-methoxy-phenyl)-(toluene-2-sulfonyl)-amino]-N-pyridin-3-ylmethyl-acetamide

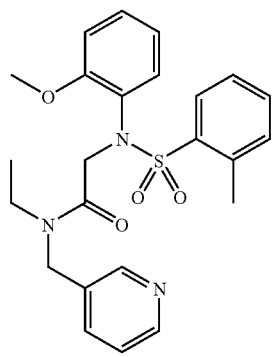

prepared by reaction of [(2-methoxy-phenyl)-(toluene-2-sulfonyl)-amino]-acetic acid with ethyl-pyridin-3-ylmethyl-amine LC-MS: rt=0.78 min, 454 (M+1, ES+).

EXAMPLE 148

N-Ethyl-2-[(2-methoxy-phenyl)-(toluene-2-sulfonyl)-amino]-N-pyridin-2-ylmethyl-acetamide prepared by reaction of [(2-methoxy-phenyl)-(toluene-2-sulfonyl)-amino]-acetic acid with ethyl-pyridin-2-ylmethyl-amine LC-MS: rt=0.82 min, 454 (M+1, ES+).

EXAMPLE 149

N-(2-Cyano-ethyl)-N-ethyl-2-[(2-methoxy-phenyl)-(toluene-2-sulfonyl)-amino]-acetamide

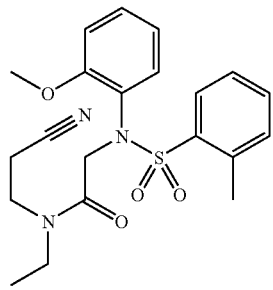

prepared by reaction of [(2-methoxy-phenyl)-(toluene-2-sulfonyl)-amino]-acetic acid with 3-ethylamino-propionitrile LC-MS: rt=0.94 min, 416 (M+1, ES+).

EXAMPLE 150

N-(4-Cyano-benzyl)-N-ethyl-2-[(2-methoxy-phenyl)-(toluene-2-sulfonyl)-amino]-acetamide

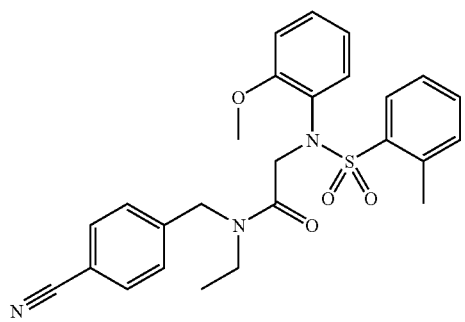

prepared by reaction of [(2-methoxy-phenyl)-(toluene-2-sulfonyl)-amino]-acetic acid with 4-ethylaminomethyl-benzonitrile LC-MS: rt=1.03 min, 478 (M+1, ES+).

EXAMPLE 151

N-Ethyl-2-[(2-methoxy-phenyl)-(toluene-2-sulfonyl)-amino]-N-(1-methyl-1H-pyrrol-2-ylmethyl)-acetamide

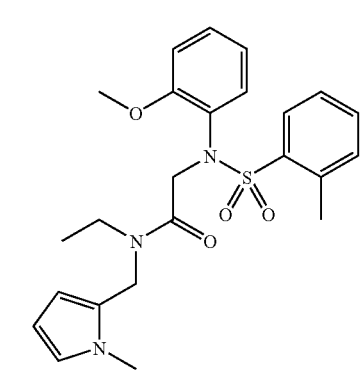

prepared by reaction of [(2-methoxy-phenyl)-(toluene-2-sulfonyl)-amino]-acetic acid with ethyl-(1-methyl-1H-pyrrol-2-ylmethyl)-amine LC-MS: rt=1.03 min, 456 (M+1, ES+).

EXAMPLE 152

N-Benzyl-N-cyanomethyl-2-[(2-methoxy-phenyl)-(toluene-2-sulfonyl)-amino]-acetamide

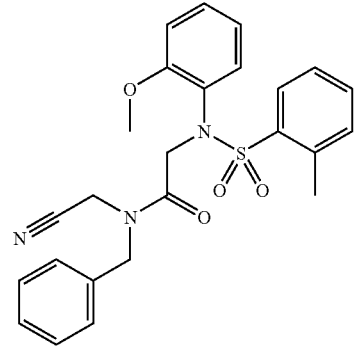

prepared by reaction of [(2-methoxy-phenyl)-(toluene-2-sulfonyl)-amino]-acetic acid with benzylamino-acetonitrile LC-MS: rt=1.02 min, 464 (M+1, ES+).

EXAMPLE 153

N-Benzyl-N-(2-cyano-ethyl)-2-[(2-methoxy-phenyl)-(toluene-2-sulfonyl)-amino]-acetamide

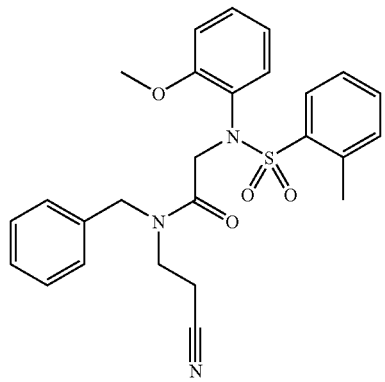

prepared by reaction of [(2-methoxy-phenyl)-(toluene-2-sulfonyl)-amino]-acetic acid with 3-benzylamino-propionitrile LC-MS: rt=1.02 min, 478 (M+1, ES+).

EXAMPLE 154

N-Ethyl-N-(4-hydroxy-benzyl)-2-[(2-methoxy-phenyl)-(toluene-2-sulfonyl)-amino]-acetamide

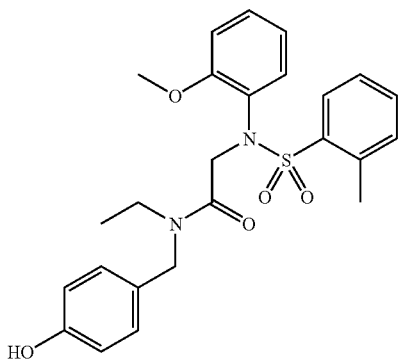

prepared by reaction of [(2-methoxy-phenyl)-(toluene-2-sulfonyl)-amino]-acetic acid with 4-ethylaminomethyl-phenol LC-MS: rt=0.85 min, 469 (M+1, ES+).

EXAMPLE 155

N-Ethyl-2-[(2-methoxy-phenyl)-(toluene-2-sulfonyl)-amino]-N-quinolin-3-ylmethyl-acetamide

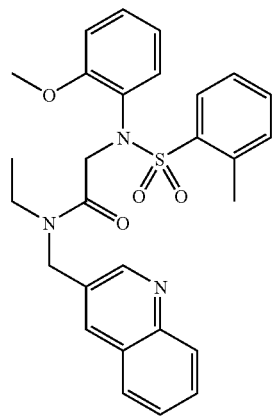

prepared by reaction of [(2-methoxy-phenyl)-(toluene-2-sulfonyl)-amino]-acetic acid with ethyl-quinolin-3-ylmethyl-amine LC-MS: rt=0.87 min, 504 (M+1, ES+).

EXAMPLE 156

N-Ethyl-2-[(2-methoxy-phenyl)-(toluene-2-sulfonyl)-amino]-N-quinolin-4-ylmethyl-acetamide

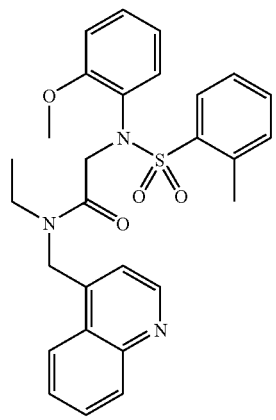

prepared by reaction of [(2-methoxy-phenyl)-(toluene-2-sulfonyl)-amino]-acetic acid with ethyl-quinolin-4-ylmethyl-amine LC-MS: rt=0.84 min, 504 (M+1, ES+).

EXAMPLE 157

N-(4-Dimethylamino-benzyl)-N-ethyl-2-[(2-methoxy-phenyl)-(toluene-2-sulfonyl)-amino]-acetamide

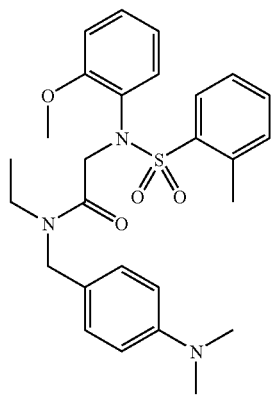

prepared by reaction of [(2-methoxy-phenyl)-(toluene-2-sulfonyl)-amino]-acetic acid with (4-ethylaminomethyl-phenyl)-dimethyl-amine LC-MS: rt=0.83 min, 496 (M+1, ES+).

EXAMPLE 158

N-Ethyl-N-(3-hydroxy-benzyl)-2-[(2-methoxy-phenyl)-(toluene-2-sulfonyl)-amino]-acetamide

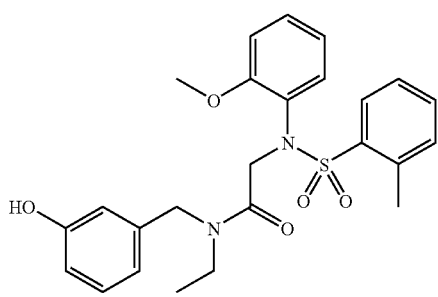

prepared by reaction of [(2-methoxy-phenyl)-(toluene-2-sulfonyl)-amino]-acetic acid with 3-ethylaminomethyl-phenol LC-MS: rt=0.97 min, 469 (M+1, ES+).

EXAMPLE 159

N-Ethyl-2-[(6-methoxy-pyridin-3-yl)-(toluene-2-sulfonyl)-amino]-N-thiazol-2-ylmethyl-acetamide

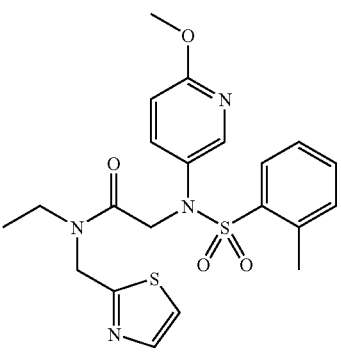

prepared by reaction of [(6-methoxy-pyridin-3-yl)-(toluene-2-sulfonyl)-amino]-acetic acid with ethyl-thiazol-2-ylmethyl-amine LC-MS: rt=0.93 min, 461 (M+1, ES+).

EXAMPLE 160

N-Ethyl-2-[(6-methoxy-pyridin-3-yl)-(toluene-2-sulfonyl)-amino]-N-(6-methyl-pyridin-2-ylmethyl)-acetamide

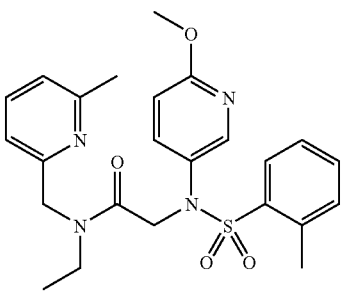

prepared by reaction of [(6-methoxy-pyridin-3-yl)-(toluene-2-sulfonyl)-amino]-acetic acid with ethyl-(6-methyl-pyridin-2-ylmethyl)-amine LC-MS: rt=0.77 min, 469 (M+1, ES+).

EXAMPLE 161

N-Benzyl-N-(2-hydroxy-ethyl)-2-[(6-methoxy-pyridin-3-yl)-(toluene-2-sulfonyl)-amino]-acetamide

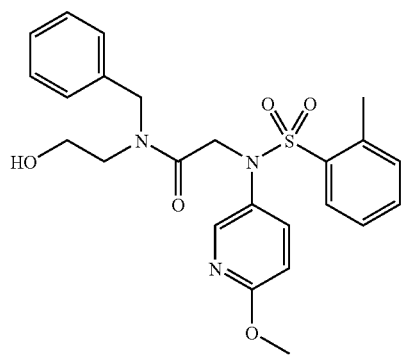

prepared by reaction of [(6-methoxy-pyridin-3-yl)-(toluene-2-sulfonyl)-amino]-acetic acid with 2-benzylamino-ethanol LC-MS: rt=0.93 min, 470 (M+1, ES+).

EXAMPLE 162

N-Ethyl-2-[(6-methoxy-pyridin-3-yl)-(toluene-2-sulfonyl)-amino]-N-pyridin-3-ylmethyl-acetamide

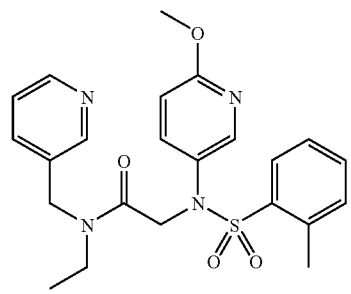

prepared by reaction of [(6-methoxy-pyridin-3-yl)-(toluene-2-sulfonyl)-amino]-acetic acid with ethyl-pyridin-3-ylmethyl-amine LC-MS: rt=0.75 min, 455 (M+1, ES+).

EXAMPLE 163

N-Ethyl-2-[(6-methoxy-pyridin-3-yl)-(toluene-2-sulfonyl)-amino]-N-pyridin-2-ylmethyl-acetamide

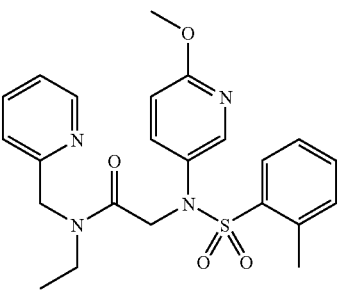

prepared by reaction of [(6-methoxy-pyridin-3-yl)-(toluene-2-sulfonyl)-amino]-acetic acid with ethyl-pyridin-2-ylmethyl-amine LC-MS: rt=0.78 min, 455 (M+1, ES+).

EXAMPLE 164

N-(2-Cyano-ethyl)-N-ethyl-2-[(6-methoxy-pyridin-3-yl)-(toluene-2-sulfonyl)-amino]-acetamide

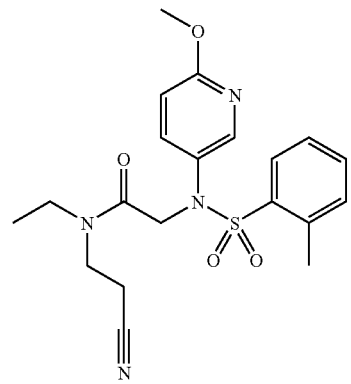

prepared by reaction of [(6-methoxy-pyridin-3-yl)-(toluene-2-sulfonyl)-amino]-acetic acid with 3-ethylamino-propionitrile LC-MS: rt=0.91 min, 417 (M+1, ES+).

EXAMPLE 165

N-(4-Cyano-benzyl)-N-ethyl-2-[(6-methoxy-pyridin-3-yl)-(toluene-2-sulfonyl)-amino]-acetamide

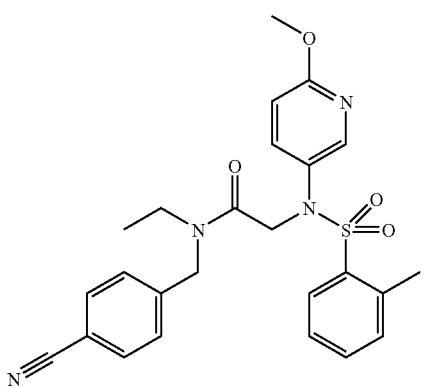

prepared by reaction of [(6-methoxy-pyridin-3-yl)-(toluene-2-sulfonyl)-amino]-acetic acid with 4-ethylaminomethyl-benzonitrile LC-MS: rt=1.00 min, 479 (M+1, ES+).

EXAMPLE 166

N-Ethyl-2-[(6-methoxy-pyridin-3-yl)-(toluene-2-sulfonyl)-amino]-N-(1-methyl-1H-pyrrol-2-ylmethyl)-acetamide

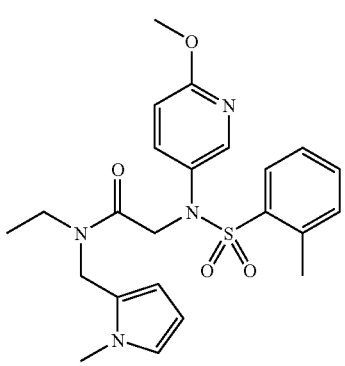

prepared by reaction of [(6-methoxy-pyridin-3-yl)-(toluene-2-sulfonyl)-amino]-acetic acid with ethyl-(1-methyl-1H-pyrrol-2-ylmethyl)-amine LC-MS: rt=1.00 min, 457 (M+1, ES+).

EXAMPLE 167

N-Benzyl-N-(2-hydroxy-ethyl)-2-[(toluene-2-sulfonyl)-p-tolyl-amino]-acetamide

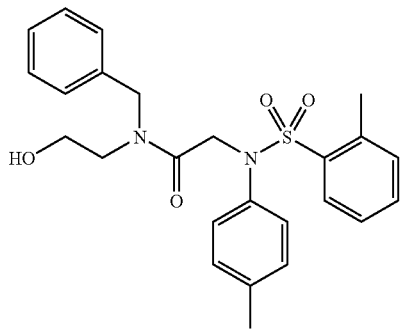

prepared by reaction of [(toluene-2-sulfonyl)-p-tolyl-amino]-acetic acid with 2-benzylamino-ethanol LC-MS: rt=0.98 min, 453 (M+1, ES+).

EXAMPLE 168

N-Ethyl-N-pyridin-3-ylmethyl-2-[(toluene-2-sulfonyl)-p-tolyl-amino]-acetamide

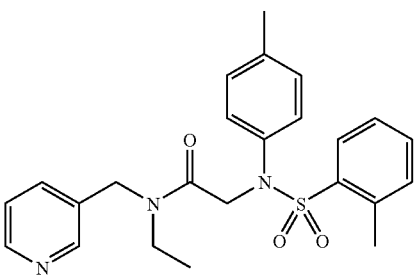

prepared by reaction of [(toluene-2-sulfonyl)-p-tolyl-amino]-acetic acid with ethyl-pyridin-3-ylmethyl-amine LC-MS: rt=0.80 min, 438 (M+1, ES+).

EXAMPLE 169

N-Ethyl-N-thiazol-2-ylmethyl-2-[(toluene-2-sulfonyl)-p-tolyl-amino]-acetamide

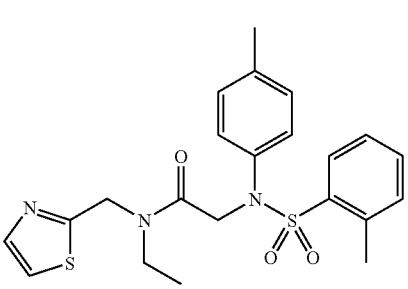

prepared by reaction of [(toluene-2-sulfonyl)-p-tolyl-amino]-acetic acid with ethyl-thiazol-2-ylmethyl-amine LC-MS: rt=0.98 min, 444 (M+1, ES+).

EXAMPLE 170

N-Ethyl-N-(6-methyl-pyridin-2-ylmethyl)-2-[(toluene-2-sulfonyl)-p-tolyl-amino]-acetamide

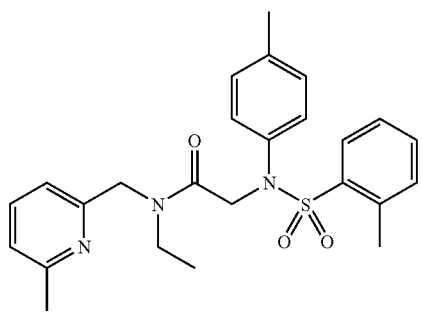

prepared by reaction of [(toluene-2-sulfonyl)-p-tolyl-amino]-acetic acid with ethyl-(6-methyl-pyridin-2-ylmethyl)-amine LC-MS: rt=0.82 min, 452 (M+1, ES+).

EXAMPLE 171

N-(2-Hydroxy-ethyl)-N-pyridin-2-ylmethyl-2-[(toluene-2-sulfonyl)-p-tolyl-amino]-acetamide

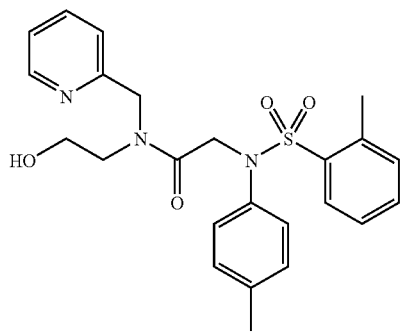

prepared by reaction of [(toluene-2-sulfonyl)-p-tolyl-amino]-acetic acid with 2-[(pyridin-2-ylmethyl)-amino]-ethanol LC-MS: rt=0.78 min, 454 (M+1, ES+).

EXAMPLE 172

N-Ethyl-N-quinolin-2-ylmethyl-2-[(toluene-2-sulfonyl)-p-tolyl-amino]-acetamide

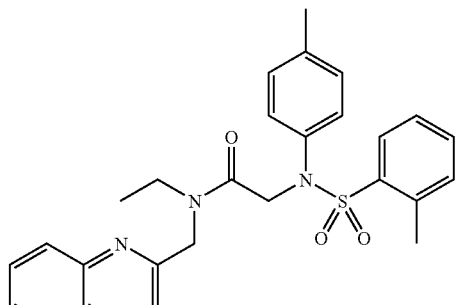

prepared by reaction of [(toluene-2-sulfonyl)-p-tolyl-amino]-acetic acid with ethyl-quinolin-2-ylmethyl-amine LC-MS: rt=0.94 min, 488 (M+1, ES+).

EXAMPLE 173

2-[(6-Amino-pyridin-3-yl)-(4-tert-butyl-benzenesulfonyl)-amino]-N-ethyl-N-pyridin-2-ylmethyl-acetamide

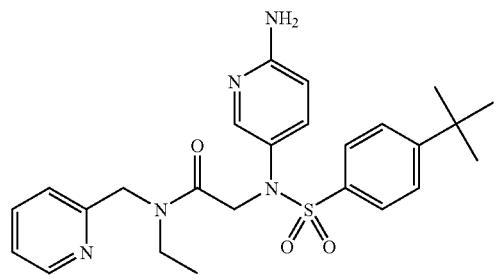

prepared by reaction of [(6-amino-pyridin-3-yl)-(4-tert-butyl-benzenesulfonyl)-amino]-acetic acid with ethyl-pyridin-2-ylmethyl-amine LC-MS: rt=0.73 min, 482 (M+1, ES+).

EXAMPLE 174

2-[(6-Amino-pyridin-3-yl)-(4-tert-butyl-benzene-sulfonyl)-amino]-N-ethyl-N-(6-methyl-pyridin-2-ylmethyl)-acetamide

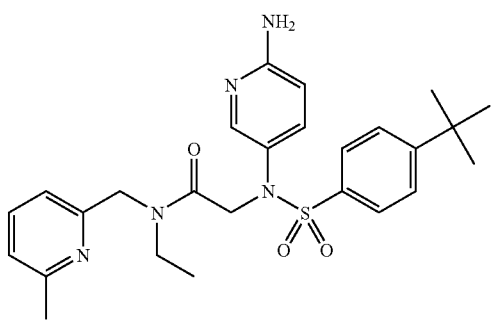

prepared by reaction of [(6-amino-pyridin-3-yl)-(4-tert-butyl-benzenesulfonyl)-amino]-acetic acid with ethyl-(6-methyl-pyridin-2-ylmethyl)-amine LC-MS: rt=0.71 min, 496 (M+1, ES+).

EXAMPLE 175

2-[(6-Amino-pyridin-3-yl)-(4-tert-butyl-benzene-sulfonyl)-amino]-N-benzyl-N-ethyl-acetamide

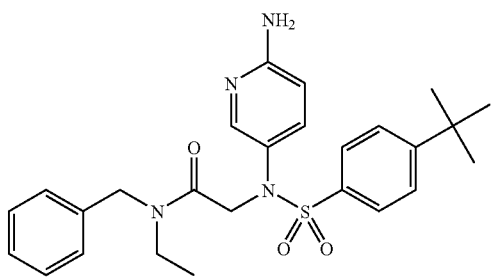

prepared by reaction of [(6-amino-pyridin-3-yl)-(4-tert-butyl-benzenesulfonyl)-amino]-acetic acid with benzyl-ethyl-amine LC-MS: rt=0.88 min, 481 (M+1, ES+).

EXAMPLE 176

N,N-Diethyl-2-[(3-methyl-pyridine-2-sulfonyl)-p-tolyl-amino]-acetamide

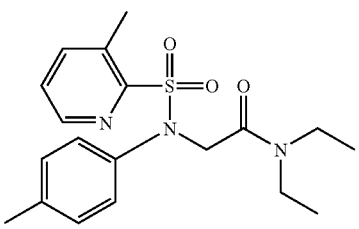

prepared by reaction of [(3-methyl-pyridine-2-sulfonyl)-p-tolyl-amino]-acetic acid with diethylamine LC-MS: rt=0.94 min, 376 (M+1, ES+).

EXAMPLE 177

N-Ethyl-2-[(3-methyl-pyridine-2-sulfonyl)-p-tolyl-amino]-N-pyridin-2-ylmethyl-acetamide

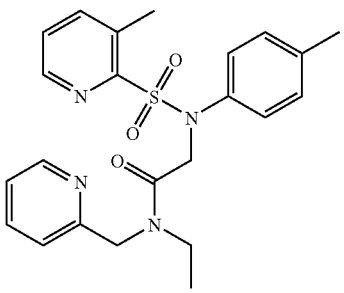

prepared by reaction of [(3-methyl-pyridine-2-sulfonyl)-p-tolyl-amino]-acetic acid with ethyl-pyridin-2-ylmethyl-amine LC-MS: rt=0.78 min, 439 (M+1, ES+).

EXAMPLE 178

N-Ethyl-2-[(3-methyl-pyridine-2-sulfonyl)-p-tolyl-amino]-N-(6-methyl-pyridin-2-ylmethyl)-acetamide

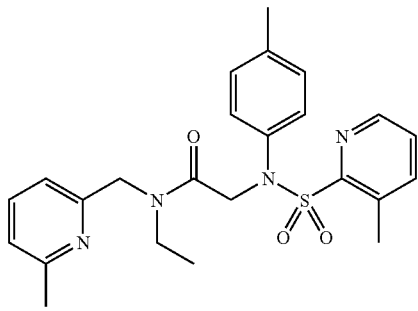

prepared by reaction of [(3-methyl-pyridine-2-sulfonyl)-p-tolyl-amino]-acetic acid with ethyl-(6-methyl-pyridin-2-yl-methyl)-amine LC-MS: rt=0.78 min, 453 (M+1, ES+).

EXAMPLE 179

N,N-Diethyl-2-[(3-methyl-pyridine-2-sulfonyl)-m-tolyl-amino]-acetamide

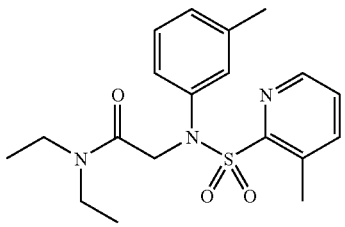

prepared by reaction of [(3-methyl-pyridine-2-sulfonyl)-m-tolyl-amino]-acetic acid with diethylamine LC-MS: rt=0.94 min, 376 (M+1, ES+).

EXAMPLE 180

N-Ethyl-2-[(3-methyl-pyridine-2-sulfonyl)-m-tolyl-amino]-N-pyridin-2-ylmethyl-acetamide

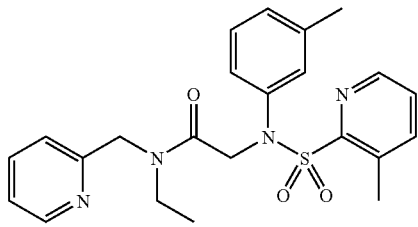

prepared by reaction of [(3-methyl-pyridine-2-sulfonyl)-m-tolyl-amino]-acetic acid with ethyl-pyridin-2-ylmethyl-amine LC-MS: rt=0.78 min, 439 (M+1, ES+).

EXAMPLE 181

N-Ethyl-2-[(3-methyl-pyridine-2-sulfonyl)-m-tolyl-amino]-N-(6-methyl-pyridin-2-ylmethyl)-acetamide

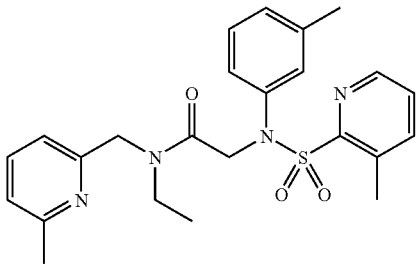

prepared by reaction of [(3-methyl-pyridine-2-sulfonyl)-m-tolyl-amino]-acetic acid with ethyl-(6-methyl-pyridin-2-yl-methyl)-amine LC-MS: rt=0.78 min, 453 (M+1, ES+).

EXAMPLE 182

N-(2-Hydroxy-ethyl)-2-[(3-methyl-pyridine-2-sulfonyl)-m-tolyl-amino]-N-pyridin-2-ylmethyl-acetamide

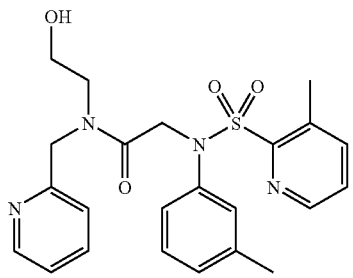

prepared by reaction of [(3-methyl-pyridine-2-sulfonyl)-m-tolyl-amino]-acetic acid with 2-[(pyridin-2-ylmethyl)-amino]-ethanol LC-MS: rt=0.72 min, 455 (M+1, ES+).

EXAMPLE 183

N,N-Diethyl-2-[(2-methoxy-phenyl)-(3-methyl-pyridine-2-sulfonyl)-amino]-acetamide

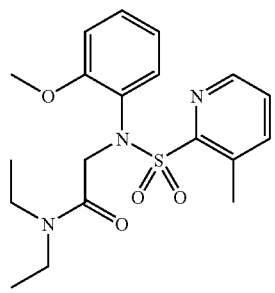

prepared by reaction of [(2-methoxy-phenyl)-(3-methyl-pyridine-2-sulfonyl)-amino]-acetic acid with diethylamine
LC-MS: rt=0.87 min, 392 (M+1, ES+).

EXAMPLE 184

N-Ethyl-2-[(2-methoxy-phenyl)-(3-methyl-pyridine-2-sulfonyl)-amino]-N-(6-methyl-pyridin-2-ylmethyl)-acetamide

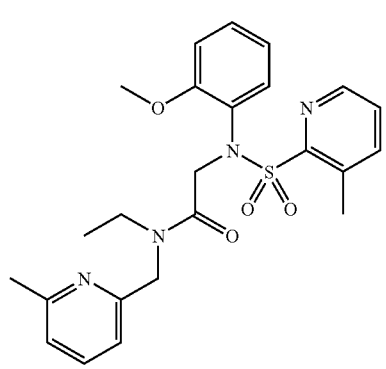

prepared by reaction of [(2-methoxy-phenyl)-(3-methyl-pyridine-2-sulfonyl)-amino]-acetic acid with ethyl-(6-methyl-pyridin-2-ylmethyl)-amine
LC-MS: rt=0.72 min, 469 (M+1, ES+).

EXAMPLE 185

N-Benzyl-N-ethyl-2-[(2-methoxy-phenyl)-(3-methyl-pyridine-2-sulfonyl)-amino]-acetamide

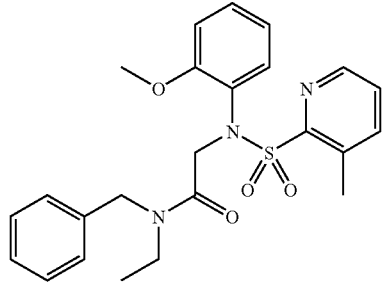

prepared by reaction of [(2-methoxy-phenyl)-(3-methyl-pyridine-2-sulfonyl)-amino]-acetic acid with benzyl-ethyl-amine
LC-MS: rt=0.98 min, 454 (M+1, ES+).

EXAMPLE 186

N-Ethyl-2-[(2-methoxy-phenyl)-(3-methyl-pyridine-2-sulfonyl)-amino]-N-pyridin-2-ylmethyl-acetamide

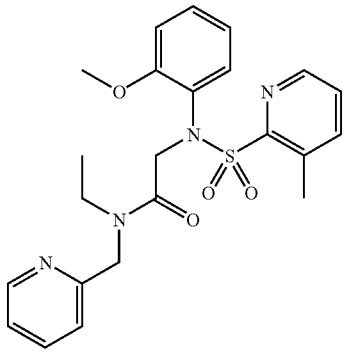

prepared by reaction of [(2-methoxy-phenyl)-(3-methyl-pyridine-2-sulfonyl)-amino]-acetic acid with ethyl-pyridin-2-ylmethyl-amine
LC-MS: rt=0.70 min, 455 (M+1, ES+).

EXAMPLE 187

N,N-Diethyl-2-[(1,2,3,4-tetrahydro-isoquinoline-7-sulfonyl)-p-tolyl-amino]-acetamide

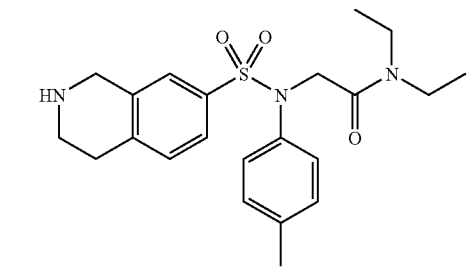

prepared by reaction of [(1,2,3,4-tetrahydro-isoquinoline-7-sulfonyl)-p-tolyl-amino]-acetic acid with diethylamine; due to the presence of formic acid in the eluent of the HPLC chromatography the product contained considerable amounts of N,N-diethyl-2-[(2-formyl-1,2,3,4-tetrahydro-isoquinoline-7-sulfonyl)-p-tolyl-amino]-acetamide (LC-MS: rt=0.91 min, 444 (M+1, ES+))
LC-MS: rt=0.74 min, 416 (M+1, ES+).

EXAMPLE 188

N-Ethyl-N-pyridin-2-ylmethyl-2-[(1,2,3,4-tetrahydro-isoquinoline-7-sulfonyl)-p-tolyl-amino]-acetamide

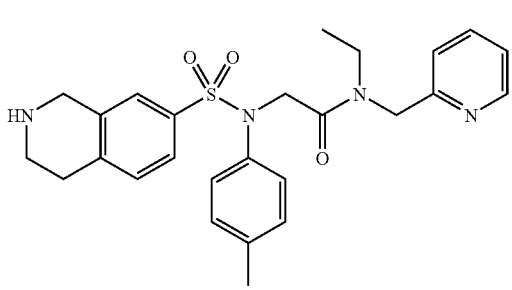

prepared by reaction of [(1,2,3,4-tetrahydro-isoquinoline-7-sulfonyl)-p-tolyl-amino]-acetic acid with ethyl-pyridin-2-ylmethyl-amine; due to the presence of formic acid in the eluent of the HPLC chromatography the product contained considerable amounts of N-ethyl-2-[(2-formyl-1,2,3,4-tetrahydro-isoquinoline-7-sulfonyl)-p-tolyl-amino]-N-pyridin-2-ylmethyl-acetamide (LC-MS: rt=0.77 min, 507 (M+1, ES+))

LC-MS: rt=0.64 min, 479 (M+1, ES+).

E.4 Synthesis of Sulfonylamino-acetic Acids (EDC Coupling)

A solution of the respective acetic acid derivative (0.10 mmol) in DMF (1.0 mL) was treated with solutions of DMAP (0.30 mmol) and of EDC hydrochloride (0.15 mmol) in DMF. A solution of the respective amine (0.12 mmol) in DMF was added. The reaction mixture was stirred at RT for 12 h and purified by preparative HPLC chromatography to give the following sulfonamides:

EXAMPLE 189

N-Ethyl-2-[(5-isopropyl-pyridine-2-sulfonyl)-m-tolyl-amino]-N-(6-methyl-pyridin-2-ylmethyl)-acetamide

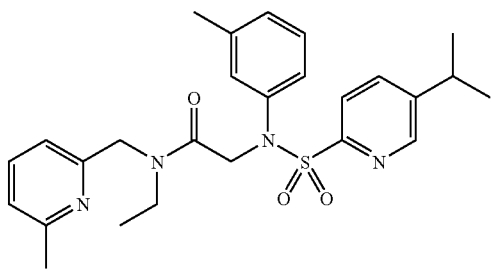

prepared by reaction of [(5-isopropyl-pyridine-2-sulfonyl)-m-tolyl-amino]-acetic acid with ethyl-(6-methyl-pyridin-2-ylmethyl)-amine LC-MS: rt=0.83 min, 481 (M+1, ES+).

EXAMPLE 190

N,N-Diethyl-2-[(5-isopropyl-pyridine-2-sulfonyl)-(2-methoxy-phenyl)-amino]-acetamide

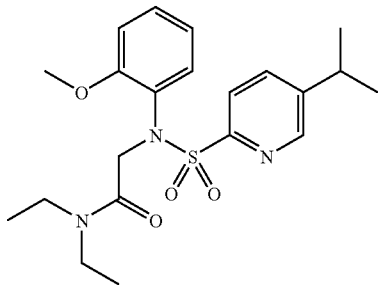

prepared by reaction of [(5-isopropyl-pyridine-2-sulfonyl)-(2-methoxy-phenyl)-amino]-acetic acid with diethylamine
LC-MS: rt=0.96 min, 420 (M+1, ES+).

EXAMPLE 191

N-Ethyl-2-[(5-isopropyl-pyridine-2-sulfonyl)-(2-methoxy-phenyl)-amino]-N-(6-methyl-pyridin-2-ylmethyl)-acetamide

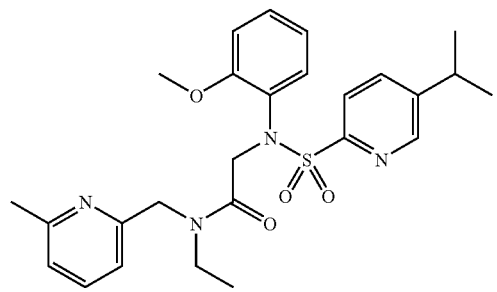

prepared by reaction of [(5-isopropyl-pyridine-2-sulfonyl)-(2-methoxy-phenyl)-amino]-acetic acid with ethyl-(6-methyl-pyridin-2-ylmethyl)-amine
LC-MS: rt=0.80 min, 497 (M+1, ES+).

EXAMPLE 192

N-Benzyl-N-ethyl-2-[(5-isopropyl-pyridine-2-sulfonyl)-(2-methoxy-phenyl)-amino]-acetamide

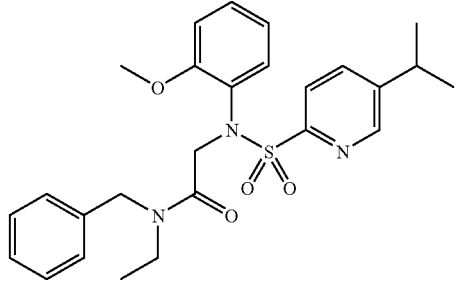

prepared by reaction of [(5-isopropyl-pyridine-2-sulfonyl)-(2-methoxy-phenyl)-amino]-acetic acid with benzyl-ethyl-amine LC-MS: rt=1.05 min, 482 (M+1, ES+).

EXAMPLE 193

N-Ethyl-2-[(5-isopropyl-pyridine-2-sulfonyl)-(6-methoxy-pyridin-3-yl)-amino]-N-pyridin-2-ylmethyl-acetamide

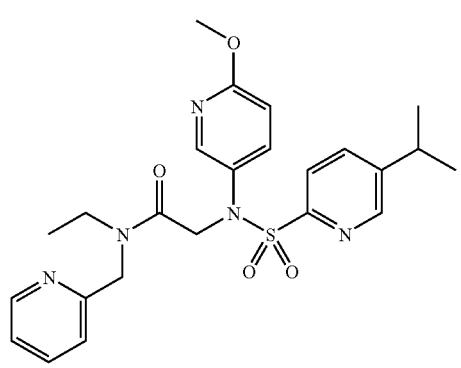

prepared by reaction of [(5-isopropyl-pyridine-2-sulfonyl)-(6-methoxy-pyridin-3-yl)-amino]-acetic acid with ethyl-pyridin-2-ylmethyl-amine LC-MS: rt=0.80 min, 484 (M+1, ES+).

EXAMPLE 194

N-Ethyl-2-[(5-isopropyl-pyridine-2-sulfonyl)-(6-methoxy-pyridin-3-yl)-amino]-N-(6-methyl-pyridin-2-ylmethyl)-acetamide

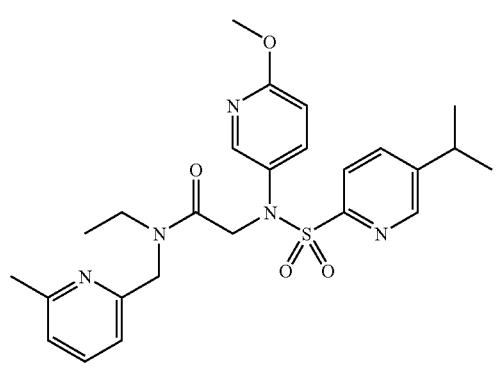

prepared by reaction of [(5-isopropyl-pyridine-2-sulfonyl)-(6-methoxy-pyridin-3-yl)-amino]-acetic acid with ethyl-(6-methyl-pyridin-2-ylmethyl)-amine LC-MS: rt=0.79 min, 498 (M+1, ES+).

EXAMPLE 195

N-(2-Hydroxy-ethyl)-2-[(5-isopropyl-pyridine-2-sulfonyl)-(6-methoxy-pyridin-3-yl)-amino]-N-pyridin-2-ylmethyl-acetamide

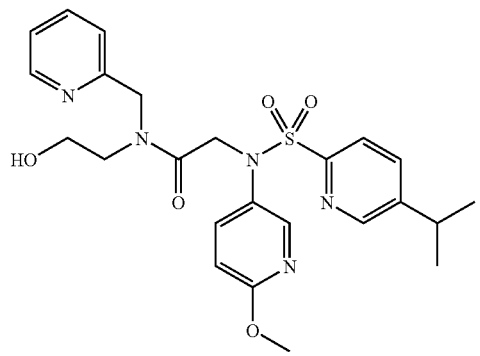

prepared by reaction of [(5-isopropyl-pyridine-2-sulfonyl)-(6-methoxy-pyridin-3-yl)-amino]-acetic acid with 2-[(pyridin-2-ylmethyl)-amino]-ethanol LC-MS: rt=0.75 min, 500 (M+1, ES+).

EXAMPLE 196

N-Benzyl-N-ethyl-2-[(5-isopropyl-pyridine-2-sulfonyl)-(6-methoxy-pyridin-3-yl)-amino]-acetamide

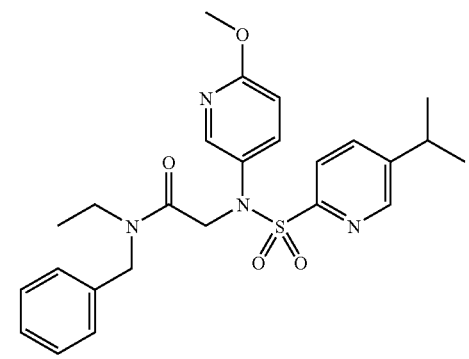

prepared by reaction of [(5-isopropyl-pyridine-2-sulfonyl)-(6-methoxy-pyridin-3-yl)-amino]-acetic acid with benzyl-ethyl-amine LC-MS: rt=1.03 min, 483 (M+1, ES+).

EXAMPLE 197

N-Ethyl-2-[(5-methyl-pyridine-2-sulfonyl)-p-tolyl-amino]-N-(6-methyl-pyridin-2-ylmethyl)-acetamide

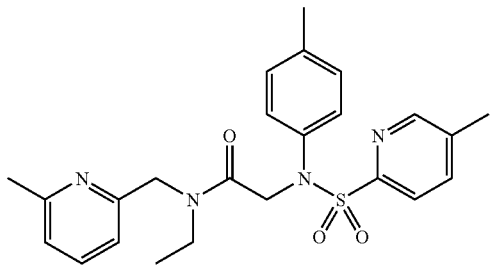

prepared by reaction of [(5-methyl-pyridine-2-sulfonyl)-p-tolyl-amino]-acetic acid with ethyl-(6-methyl-pyridin-2-ylmethyl)-amine
LC-MS: rt=0.77 min, 453 (M+1, ES+).

EXAMPLE 198

N-Ethyl-2-[(5-methyl-pyridine-2-sulfonyl)-p-tolyl-amino]-N-pyridin-3-ylmethyl-acetamide

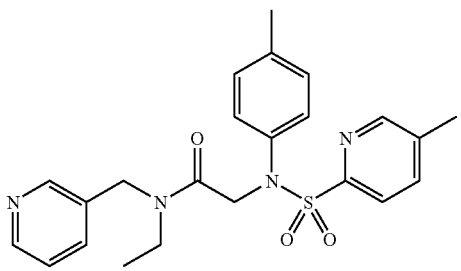

prepared by reaction of [(5-methyl-pyridine-2-sulfonyl)-p-tolyl-amino]-acetic acid with ethyl-pyridin-3-ylmethyl-amine
LC-MS: rt=0.75 min, 439 (M+1, ES+).

EXAMPLE 199

2-[(4-tert-Butyl-benzenesulfonyl)-(6-methyl-pyridin-3-yl)-amino]-N,N-diethyl-acetamide

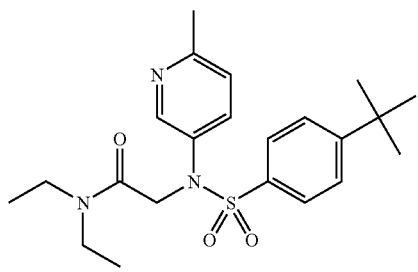

prepared by reaction of [(4-tert-butyl-benzenesulfonyl)-(6-methyl-pyridin-3-yl)-amino]-acetic acid with diethylamine
LC-MS: rt=0.87 min, 418 (M+1, ES+).

EXAMPLE 200

2-[(4-tert-Butyl-benzenesulfonyl)-(6-methyl-pyridin-3-yl)-amino]-N-ethyl-N-pyridin-2-ylmethyl-acetamide

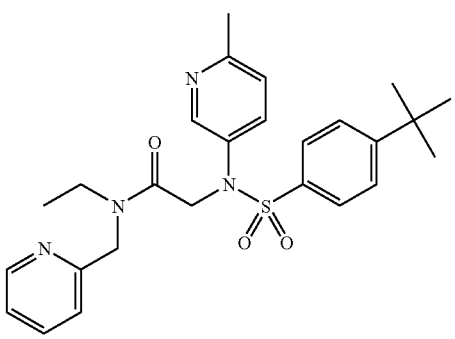

prepared by reaction of [(4-tert-butyl-benzenesulfonyl)-(6-methyl-pyridin-3-yl)-amino]-acetic acid with ethyl-pyridin-2-ylmethyl-amine
LC-MS: rt=0.78 min, 481 (M+1, ES+).

EXAMPLE 201

2-[(4-tert-Butyl-benzenesulfonyl)-(6-methyl-pyridin-3-yl)-amino]-N-ethyl-N-(6-methyl-pyridin-2-ylmethyl)-acetamide

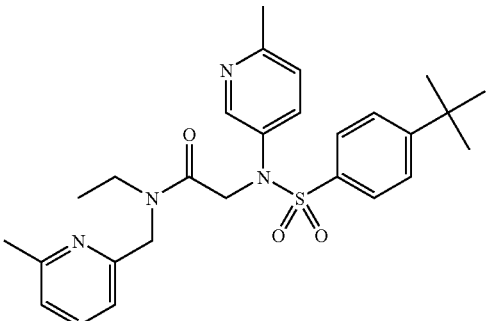

prepared by reaction of [(4-tert-butyl-benzenesulfonyl)-(6-methyl-pyridin-3-yl)-amino]-acetic acid with ethyl-(6-methyl-pyridin-2-ylmethyl)-amine
LC-MS: rt=0.77 min, 495 (M+1, ES+).

EXAMPLE 202

2-[(4-tert-Butyl-benzenesulfonyl)-(6-methyl-pyridin-3-yl)-amino]-N-(2-hydroxy-ethyl)-N-pyridin-2-ylmethyl-acetamide

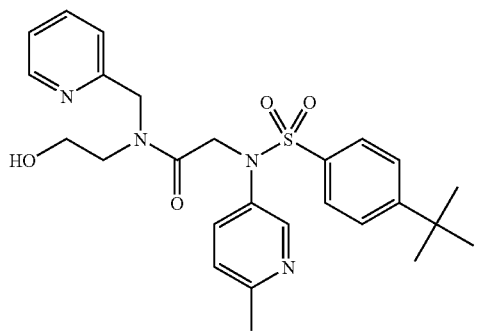

prepared by reaction of [(4-tert-butyl-benzenesulfonyl)-(6-methyl-pyridin-3-yl)-amino]-acetic acid with 2-[(pyridin-2-ylmethyl)-amino]-ethanol LC-MS: rt=0.72 min, 497 (M+1, ES+).

EXAMPLE 203

N-Benzyl-2-[(4-tert-butyl-benzenesulfonyl)-(6-methyl-pyridin-3-yl)-amino]-N-ethyl-acetamide

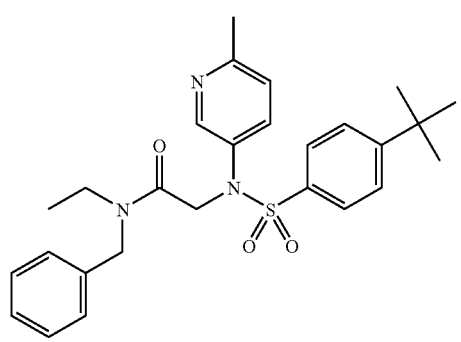

prepared by reaction of [(4-tert-butyl-benzenesulfonyl)-(6-methyl-pyridin-3-yl)-amino]-acetic acid with benzyl-ethyl-amine LC-MS: rt=0.95 min, 480 (M+1, ES+).

EXAMPLE 204

N-Ethyl-2-[(6-methoxy-pyridin-3-yl)-(3-methyl-pyridine-2-sulfonyl)-amino]-N-pyridin-2-ylmethyl-acetamide

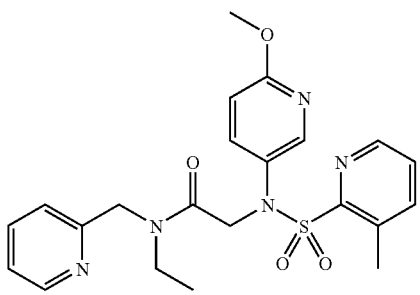

prepared by reaction of [(6-methoxy-pyridin-3-yl)-(3-methyl-pyridine-2-sulfonyl)-amino]-acetic acid with ethyl-pyridin-2-ylmethyl-amine LC-MS: rt=0.70 min, 456 (M+1, ES+).

EXAMPLE 205

N-Ethyl-2-[(6-methoxy-pyridin-3-yl)-(3-methyl-pyridine-2-sulfonyl)-amino]-N-(6-methyl-pyridin-2-ylmethyl)-acetamide

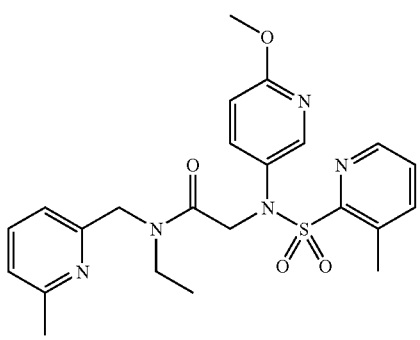

prepared by reaction of [(6-methoxy-pyridin-3-yl)-(3-methyl-pyridine-2-sulfonyl)-amino]-acetic acid with ethyl-(6-methyl-pyridin-2-ylmethyl)-amine LC-MS: rt=0.72 min, 470 (M+1, ES+).

EXAMPLE 206

N-(2-Hydroxy-ethyl)-2-[(6-methoxy-pyridin-3-yl)-(3-methyl-pyridine-2-sulfonyl)-amino]-N-pyridin-2-ylmethyl-acetamide

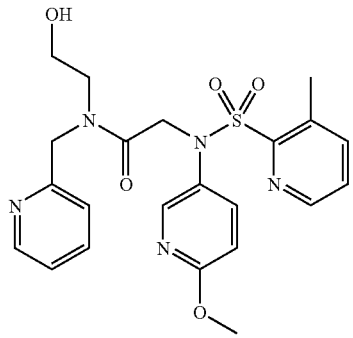

prepared by reaction of [(6-methoxy-pyridin-3-yl)-(3-methyl-pyridine-2-sulfonyl)-amino]-acetic acid with 2-[(pyridin-2-ylmethyl)-amino]-ethanol LC-MS: rt=0.67 min, 472 (M+1, ES+).

EXAMPLE 207

N-Benzyl-N-ethyl-2-[(6-methoxy-pyridin-3-yl)-(3-methyl-pyridine-2-sulfonyl)-amino]-acetamide

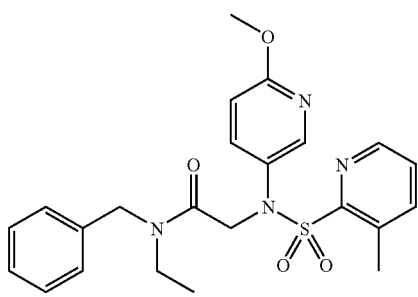

prepared by reaction of [(6-methoxy-pyridin-3-yl)-(3-methyl-pyridine-2-sulfonyl)-amino]-acetic acid with benzyl-ethyl-amine LC-MS: rt=0.98 min, 455 (M+1, ES+).

F Synthesis of N-Ethyl-2-[(2-methyl-1,2,3,4-tetrahydro-isoquinoline-7-sulfonyl)-p-tolyl-amino]-N-pyridin-2-ylmethyl-acetamide

EXAMPLE 208

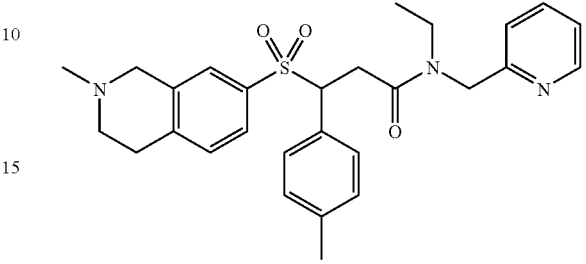

To a solution of N-ethyl-N-pyridin-2-ylmethyl-2-[(1,2,3,4-tetrahydro-isoquinoline-7-sulfonyl)-p-tolyl-amino]-acetamide (0.46 mmol) in methanol (15 mL) was added a solution of formaldehyde in water (37%, 0.92 mL), sodium cyanoborohydride (675 mg) and acetic acid (3.07 mL). After 2 h a saturated $NaHCO_3$-solution (25 mL), water (25 mL) and ethyl acetate (50 mL) were added, the layers were separated and the aqueous layer was extracted with ethyl acetate (50 mL). The combined organic layers were concentrated in vacuo and the residue was purified by preparative HPLC chromatography to give 66.7 mg (0.14 mmol, 29%) of the desired product.

LC-MS: rt=0.65 min, 493 (M+1, ES+).

G Synthesis of 2-{(3-Dimethylamino-phenyl)-[4-(1-hydroxy-1-methyl-ethyl)-benzenesulfonyl]-amino}-N-ethyl-N-pyridin-2-ylmethyl-acetamide

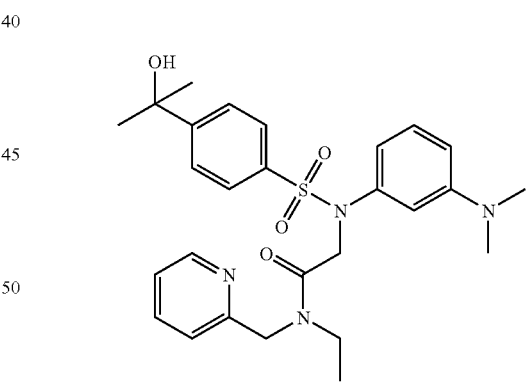

(3-Dimethylamino-phenylamino)-acetic acid methyl ester

To a solution of N,N-dimethyl-m-phenylenediamine (120 mmol) in THF (500 mL) was added methyl bromoacetate (132 mmol) and DIPEA (264 mmol). The reaction mixture was refluxed for 16 h. Water (200 mL) and ethyl acetate (300 mL) were added, the layers were separated and the aqueous layer was extracted with ethyl acetate (2×200 mL). The combined organic layers were washed with water (4×100 mL) and brine (100 mL) and dried over $Na_2SO_4$. The solvents were removed in vacuo and the residue was purified by flash-chromatography (ethyl acetate/heptane 1:4) to give 17.5 g (84.0 mmol, 70%) of an oily product which crystallized slowly.

LC-MS: rt=0.51 min, 209 (M+1, ES+).

(3-Dimethylamino-phenylamino)-acetic acid

To a solution of (3-dimethylamino-phenylamino)-acetic acid methyl ester (84 mmol) in methanol (300 mL) was added a solution of sodium hydroxide in water (2.0 mol/L, 150 mL) at 0° C. The reaction mixture was stirred at RT for 16 h and methanol was removed in vacuo. Water (200 mL) and ethyl acetate (300 mL) were added, the layers were separated and the aqueous layer was acidified to pH 2 by addition of hydrochloric acid (2.0 mol/L). The aqueous layer was extracted with ethyl acetate (3×200 mL) and concentrated in vacuo. Methanol (100 mL) was added and the obtained suspension was filtered. The filtrate was concentrated in vacuo and the obtained solid was crystallized from methanol/ethyl acetate to give 15.0 g (56.2 mmol, 67%) of (3-dimethylamino-phenylamino)-acetic acid dihydrochloride as pink crystals.

LC-MS: rt=0.40 min, 195 (M+1, ES+).

2-(3-Dimethylamino-phenylamino)-N-ethyl-N-pyridin-2-ylmethyl-acetamide

A suspension of ethyl-pyridin-2-ylmethyl-amine (41.1 mmol) and DIPEA (112 mmol) in DMF (200 mL) was cooled to −20° C. and added to a cold (−20° C.) solution of (3-dimethylamino-phenylamino)-acetic acid (37.4 mmol) and TBTU (48.6 mmol) in DMF (300 mL). The reaction mixture was stirred for 10 min at −20° C. Water (500 mL) and ethyl acetate (500 mL) were added, the layers were separated and the organic layer washed with water (4×200 mL). The combined aqueous layers were extracted with ethyl acetate (300 mL). The combined organic layers were washed with NaOH solution (1.0 mol/L, 100 mL) and brine (100 mL) and dried over $Na_2SO_4$. The solvents were removed in vacuo and the obtained solid was dissolved in ethanol. A solution of hydrogen chloride in ether was added at 0° C., the solvents were removed and the residue was crystallized from ethanol/ether to give 7.6 g product as white crystals.

LC-MS: rt=0.49 min, 313 (M+1, ES+).

2-[(4-Acetyl-benzenesulfonyl)-(3-dimethylamino-phenyl)-amino]-N-ethyl-N-pyridin-2-ylmethyl-acetamide A solution of 2-(3-dimethylamino-phenylamino)-N-ethyl-N-pyridin-2-ylmethyl-acetamide (2.50 mmol) and of DIPEA (5.00 mmol) in THF (10 mL) was added to a solution of 4-acetyl-benzenesulfonyl chloride (2.50 mmol) in THF (10 mL). The reaction mixture was stirred for 2 h, the solvents were removed and the residue was purified by preparative HPLC chromatography to give 451 mg (0.91 mmol, 36%) product as a brownish foam.

LC-MS: rt=0.75 min, 495 (M+1, ES+).

EXAMPLE 209

2-{(3-Dimethylamino-phenyl)-[4-(1-hydroxy-1-methyl-ethyl)-benzenesulfonyl]-amino}-N-ethyl-N-pyridin-2-ylmethyl-acetamide At −78° C. a solution of methyllithium in ether (1.60 mol/L, 0.25 mL) was added to a solution of titanium(IV) chloride in DCM (1.00 mol/L, 0.40 mL). The reaction mixture was treated with a solution of 2-[(4-acetyl-benzenesulfonyl)-(3-dimethyl-amino-phenyl)-amino]-N-ethyl-N-pyridin-2-ylmethyl-acetamide (0.10 mmol) in DCM (1.0 mL), allowed to reach RT, stirred for 1 h and purified by preparative HPLC chromatography.

LC-MS: rt=0.70 min, 511 (M+1, ES+).

The invention claimed is:

1. A method of antagonizing orexin receptors, comprising administering to a subject an effective amount of a compound of formula (I)

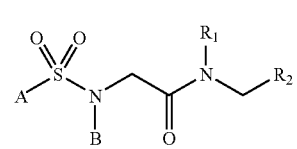

Formula (I)

wherein:
A represents 4-ethylphenyl-, 4-isopropylphenyl, 4-tert.-butylphenyl-, 2-methylphenyl-, 3-methylphenyl-, 4-cyclopropylphenyl, 3-fluorophenyl-, 2-chlorophenyl-, 3-chlorophenyl-, 4-bromophenyl-, 2-trifluoromethylphenyl-, 3-trifluoromethylphenyl-, 4-(1-hydroxy-1-methyl-ethyl)-phenyl-, 3-chloro-4-methylphenyl-, 2-methoxy-4-methylphenyl-, 3,4-difluorophenyl-, 1,2,3,4-tetrahydroisoquinolin-7-yl, 2-methyl-1,2,3,4-tetrahydroisoquinolin-7-yl, 2-formyl-1,2,3,4-tetrahydroisoquinolin-7-yl, phenylethenyl-, 1-naphthyl-, 2-naphthyl-, 3-methyl-pyridin-2-yl, 5-methyl-pyridin-2-yl, 5-isopropyl-pyridin-2-yl, 6-dimethylamino-pyridin-3-yl, 6-bromo-5-chloro-pyridin-3-yl or 8-quinolinyl-;

B represents a phenyl, a 6-membered heteroaryl or a nine- or ten-membered bicyclic heteroaryl group, which groups are unsubstituted or independently mono- or di-substituted with cyano, halogen, hydroxy, lower alkyl, hydroxy lower alkyl, amino lower alkyl, aminocarbonyl lower alkyl, sulfonylamino lower alkyl, lower alkenyl, lower alkoxy, trifluoromethyl, trifluoromethoxy, cycloalkyloxy, aryloxy, aralkyloxy, heterocyclyloxy, heterocyclyl lower alkyloxy, amino, aminocarbonyl or sulfonylamino; or a cyclohexyl, 3-piperidinyl or 4-piperidinyl group, which groups are unsubstituted or mono-substituted with hydroxy, lower alkyl, hydroxy lower alkyl, aminocarbonyl lower alkyl, sulfonylamino lower alkyl, amino, aminocarbonyl or sulfonylamino;

with the proviso that in case A represents 2-methylphenyl- or 4-bromophenyl the phenyl ring as represented by B is substituted;

$R^1$ represents lower alkyl, cycloalkyl, hydroxy lower alkyl or cyano lower alkyl;

$R^2$ represents lower alkyl, lower alkenyl, hydroxy lower alkyl, amino lower alkyl, sulfonylamino lower alkyl, cycloalkyl; an unsubstituted or mono- or disubstituted phenyl group substituted independently with cyano, halogen, hydroxy, lower alkyl, lower alkoxy, cycloalkyloxy, amino, amino lower alkyl, aminocarbonyl or sulfonylamino; an unsubstituted or mono- or di-substituted five- or six-membered heteroaryl group substituted independently with cyano, halogen, hydroxy, lower alkyl, lower alkoxy, cycloalkyloxy, amino, amino lower alkyl, aminocarbonyl or sulfonylamino; an unsubstituted or mono- or di-substituted nine- or ten-membered bicyclic heteroaryl group substituted independently with cyano, halogen, hydroxy, lower alkyl, lower alkoxy, cycloalkyloxy, amino, amino lower alkyl, aminocarbonyl or sulfonylamino, or a pure enantiomer, a mixture of enantiomers, a pure diastereoisomer, a mixture of diastereoisomers, a diastereoisomeric racemate, a mixture of diastereoisomeric racemates, or the meso-form, or a pharmaceutically acceptable salt, solvent complex, or morphological form, thereof.

2. The method of claim 1, wherein A represents a 4-ethylphenyl group.

3. The method of claim 1, wherein A represents a 4-isopropylphenyl group.

4. The method of claim 1, wherein A represents a 4-tert.-butylphenyl group.

5. The method of claim 1, wherein A represents a 2-methylphenyl group.

6. The method of claim 1, wherein A represents a 3-methylphenyl group

7. The method of claim 1, wherein A represents a 4-(1-hydroxy-1-methyl-ethyl)-phenyl group.

8. The method of claim 1, wherein A represents a 3-chloro-4-methylphenyl group.

9. The method of claim 1, wherein A represents a 2-formyl-1,2,3,4-tetrahydroisoquinolin-7-yl group.

10. The method of claim 1, wherein A represents a 2-naphthyl group.

11. The method of claim 1, wherein A represents a 3-methyl-pyridin-2-yl group.

12. The method of claim 1, wherein A represents a 5-isopropyl-pyridin-2-yl group.

13. The method of claim 1, wherein A represents a 6-dimethylamino-pyridin-3-yl group.

14. The method of claim 1, wherein said compound is selected from the group consisting of
- 2-[(4-tert-Butyl-benzenesulfonyl)-p-tolyl-amino]-N,N-diethyl-acetamide;
- 2-[(4-tert-Butyl-benzenesulfonyl)-(4-methoxy-phenyl)-amino]-N,N-diethyl-acetamide;
- 2-[(4-tert-Butyl-benzenesulfonyl)-(3-methoxy-phenyl)-amino]-N,N-diethyl-acetamide;
- 2-[(4-tert-Butyl-benzenesulfonyl)-m-tolyl-amino]-N,N-diethyl-acetamide;
- 2-[(6-Dimethylamino-pyridine-3-sulfonyl)-p-tolyl-amino]-N-ethyl-N-pyridin-2-ylmethyl-acetamide;
- N-Benzyl-2-[(4-tert-butyl-benzenesulfonyl)-p-tolyl-amino]-N-ethyl-acetamide;
- 2-[(4-tert-Butyl-benzenesulfonyl)-p-tolyl-amino]-N-ethyl-N-pyridin-4-ylmethyl-acetamide;
- N,N-Diethyl-2-[(2-methoxy-phenyl)-(toluene-2-sulfonyl)-amino]-acetamide;
- N-Benzyl-N-ethyl-2-[(6-methoxy-pyridin-3-yl)-(toluene-2-sulfonyl)-amino]-acetamide;
- N-Benzyl-N-ethyl-2-[(2-methoxy-phenyl)-(toluene-2-sulfonyl)-amino]-acetamide;
- N-Benzyl-2-[(4-tert-butyl-benzenesulfonyl)-(2-methoxy-phenyl)-amino]-N-ethyl-acetamide;
- N-Benzyl-N-ethyl-2-[(6-methoxy-pyridin-3-yl)-(naphthalene-2-sulfonyl)-amino]-acetamide;
- 2-[(4-tert-Butyl-benzenesulfonyl)-p-tolyl-amino]-N-ethyl-N-(2-hydroxy-ethyl)-acetamide;
- 2-[(3-Chloro-4-methyl-benzenesulfonyl)-p-tolyl-amino]-N,N-diethyl-acetamide;
- N-Benzyl-2-[(4-tert-butyl-benzenesulfonyl)-p-tolyl-amino]-N-(2-hydroxy-ethyl)-acetamide;
- 2-[(4-tert-Butyl-benzenesulfonyl)-p-tolyl-amino]-N-(2-cyano-ethyl)-N-ethyl-acetamide;
- 2-[(4-tert-Butyl-benzenesulfonyl)-p-tolyl-amino]-N-ethyl-N-pyridin-2-ylmethyl-acetamide;
- 2-[(4-tert-Butyl-benzenesulfonyl)-p-tolyl-amino]-N-ethyl-N-pyridin-3-ylmethyl-acetamide;
- 2-[(4-tert-Butyl-benzenesulfonyl)-p-tolyl-amino]-N-ethyl-N-(6-methyl-pyridin-2-ylmethyl)-acetamide;
- 2-[(4-tert-Butyl-benzenesulfonyl)-p-tolyl-amino]-N-ethyl-N-thiazol-2-ylmethyl-acetamide;
- 2-[(4-tert-Butyl-benzenesulfonyl)-(3-dimethylamino-phenyl)-amino]-N,N-diethyl-acetamide;
- 2-[(4-tert-Butyl-benzenesulfonyl)-(3-dimethylamino-phenyl)-amino]-N-ethyl-N-pyridin-2-ylmethyl-acetamide;
- 2-[(4-tert-Butyl-benzenesulfonyl)-(3-dimethylamino-phenyl)-amino]-N-ethyl-N-(6-methyl-pyridin-2-ylmethyl)-acetamide;
- 2-[(4-tert-Butyl-benzenesulfonyl)-p-tolyl-amino]-N-ethyl-N-(3-hydroxy-benzyl)-acetamide;
- 2-[(4-tert-Butyl-benzenesulfonyl)-(1H-indazol-6-yl)-amino]-N-ethyl-N-(6-methyl-pyridin-2-ylmethyl)-acetamide;
- 2-[(4-tert-Butyl-benzenesulfonyl)-(1H-indazol-6-yl)-amino]-N-ethyl-N-pyridin-2-ylmethyl-acetamide;
- 2-[(4-tert-Butyl-benzenesulfonyl)-p-tolyl-amino]-N-(2-hydroxy-ethyl)-N-pyridin-2-ylmethyl-acetamide;
- 2-[(4-tert-Butyl-benzenesulfonyl)-(3-dimethylamino-phenyl)-amino]-N-(2-hydroxy-ethyl)-N-pyridin-2-ylmethyl-acetamide;
- 2-[(4-tert-Butyl-benzenesulfonyl)-p-tolyl-amino]-N-cyclopropyl-N-(3-methoxy-benzyl)-acetamide;
- 2-[(4-tert-Butyl-benzenesulfonyl)-(3-dimethylamino-phenyl)-amino]-N-cyclopropyl-N-(3-methoxy-benzyl)-acetamide;
- N-Ethyl-2-[(2-methoxy-phenyl)-(toluene-2-sulfonyl)-amino]-N-thiazol-2-ylmethyl-acetamide;
- N-Benzyl-N-(2-hydroxy-ethyl)-2-[(2-methoxy-phenyl)-(toluene-2-sulfonyl)-amino]-acetamide;
- N-Ethyl-2-[(2-methoxy-phenyl)-(toluene-2-sulfonyl)-amino]-N-pyridin-2-ylmethyl-acetamide;
- N-Ethyl-N-(3-hydroxy-benzyl)-2-[(2-methoxy-phenyl)-(toluene-2-sulfonyl)-amino]-acetamide;
- N-Ethyl-2-[(6-methoxy-pyridin-3-yl)-(toluene-2-sulfonyl)-amino]-N-(6-methyl-pyridin-2-ylmethyl)-acetamide;
- N-Benzyl-N-(2-hydroxy-ethyl)-2-[(6-methoxy-pyridin-3-yl)-(toluene-2-sulfonyl)-amino]-acetamide;
- N-Ethyl-2-[(6-methoxy-pyridin-3-yl)-(toluene-2-sulfonyl)-amino]-N-pyridin-3-ylmethyl-acetamide;
- N-Ethyl-2-[(6-methoxy-pyridin-3-yl)-(toluene-2-sulfonyl)-amino]-N-pyridin-2-ylmethyl-acetamide;
- N-Ethyl-2-[(2-methoxy-phenyl)-(3-methyl-pyridine-2-sulfonyl)-amino]-N-(6-methyl-pyridin-2-ylmethyl)-acetamide;
- N-Benzyl-N-ethyl-2-[(2-methoxy-phenyl)-(3-methyl-pyridine-2-sulfonyl)-amino]-acetamide;
- 2-[(4-tert-Butyl-benzenesulfonyl)-(6-methyl-pyridin-3-yl)-amino]-N-ethyl-N-pyridin-2-ylmethyl-acetamide;
- N-Benzyl-2-[(4-tert-butyl-benzenesulfonyl)-(6-methyl-pyridin-3-yl)-amino]-N-ethyl-acetamide;
- N-Ethyl-2-[(6-methoxy-pyridin-3-yl)-(3-methyl-pyridine-2-sulfonyl)-amino]-N-(6-methyl-pyridin-2-ylmethyl)-acetamide; and
- N-Benzyl-N-ethyl-2-[(6-methoxy-pyridin-3-yl)-(3-methyl-pyridine-2-sulfonyl)-amino]-acetamide.

* * * * *